US011932882B2

(12) United States Patent
Clark et al.

(10) Patent No.: US 11,932,882 B2
(45) Date of Patent: Mar. 19, 2024

(54) REVERSE TRANSCRIPTASE VARIANTS

(71) Applicant: 10X Genomics, Inc., Pleasanton, CA (US)

(72) Inventors: Sonya A. Clark, Pleasanton, CA (US); Derek Hunter Vallejo, Pleasanton, CA (US); Carolina Cuellar, Pleasanton, CA (US); Katherine Pfeiffer, Pleasanton, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

(21) Appl. No.: 17/837,497

(22) Filed: Jun. 10, 2022

(65) Prior Publication Data

US 2022/0403350 A1    Dec. 22, 2022

Related U.S. Application Data

(63) Continuation of application No. PCT/US2020/064323, filed on Dec. 10, 2020.

(60) Provisional application No. 63/017,913, filed on Apr. 30, 2020, provisional application No. 62/946,885, filed on Dec. 11, 2019.

(51) Int. Cl.
C12N 9/12           (2006.01)

(52) U.S. Cl.
CPC .... C12N 9/1241 (2013.01); C12Y 207/07049 (2013.01)

(58) Field of Classification Search
None
See application file for complete search history.

(56) References Cited

U.S. PATENT DOCUMENTS

| | | | |
|---|---|---|---|
| 6,265,552 | B1 | 7/2001 | Schatz |
| 8,541,219 | B2 | 9/2013 | Potter |
| 8,753,845 | B2 | 6/2014 | Dhariwal |
| 9,580,698 | B1 | 2/2017 | Xu |
| 2007/0141592 | A1 | 6/2007 | Smith |
| 2010/0105112 | A1 | 4/2010 | Holtze |
| 2011/0065606 | A1 | 3/2011 | Janulaitis |
| 2013/0288925 | A1 | 10/2013 | Janulaitis |
| 2014/0155295 | A1 | 6/2014 | Hindson |
| 2014/0378345 | A1 | 12/2014 | Hindson |
| 2014/0378349 | A1 | 12/2014 | Hindson |
| 2015/0011430 | A1 | 1/2015 | Saxonov |
| 2015/0011432 | A1 | 1/2015 | Saxonov |
| 2015/0210989 | A1 | 7/2015 | Rogers |
| 2015/0376605 | A1 | 12/2015 | Jarosz |
| 2015/0376609 | A1 | 12/2015 | Hindson |
| 2015/0376700 | A1 | 12/2015 | Schnall-Levin |
| 2016/0340657 | A1 | 11/2016 | Hogrefe |
| 2018/0312822 | A1 | 11/2018 | Lee |

FOREIGN PATENT DOCUMENTS

| | | |
|---|---|---|
| WO | 2007022045 A2 | 2/2007 |
| WO | 2016040476 A1 | 3/2016 |
| WO | 2018200867 A1 | 11/2018 |

OTHER PUBLICATIONS

Accession P03355. Jul. 21, 1986 (Year: 1988).*
Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Arezi, et al., "Mutant of Moloney murine leukemia virus reverse transcriptase exhibits higher resistance to common RT-qPCR inhibitors", Anal Biochem, May 15, 2010;400(2):301-3. doi: 10.1016/j.ab.2010.01.024. Epub Jan. 25, 2010.
Arezi, et al., "Novel mutations in Moloney Murine Leukemia Virus reverse transcriptase increase thermostability through tighter binding to template-primer", Nucleic Acids Res. Feb. 2009;37(2):473-81. doi: 10.1093/nar/gkn952. Epub Dec. 4, 2008.
Baranauskas, A. et al., "Generation and characterization of new highly thermostable and processive M-MuLV reverse transcriptase variants", Protein Engineering , Design & Selection, (20121000), vol. 25, No. 10, pp. 657-668, XP055071799.
Coufal, et al., "L1 retrotransposition in human neural progenitor cells", Nature, Aug. 27, 2009;460(7259):1127-31. doi: 10.1038/nature08248. Epub Aug. 5, 2009.
Das, et al. "The Crystal Structure of the Monomeric Reverse Transcriptase from Moloney Murine Leukemia Virus", Structure. May 2004; 12(5):819-29.
Das, et al., "A Directed Approach to Improving the Solubility of Moloney Murine Leukemia Virus Reverse Transcriptase", Protein Science, 2011, 10, 1936-1941. (Year: 2001).
Fang, et al., "Fluoride-cleavable biotinylation phosphoramidite for 5'-end-labeling and affinity purification of synthetic oligonucleotides", Nucleic Acids Res. Jan. 15, 2003;31(2):708-15.
Galilee, et al., "The structure of FIV reverse transcriptase and its implications for non-nucleoside inhibitor resistance", PLOS Pathog 14(1): e1006849, Jan. 24, 2018.
Huseby, et al., "Structure and Biological Activities of Beta Toxin from *Staphylococcus aureus*", Journal of Bacteriology Nov. 2007, 189 (23) 8719-8726; DOI: 10.1128/JB.00741-07.
Konishi, et al., "Stabilization of Moloney murine leukemia virus reverse transcriptase by sitedirected mutagenesis of surface residue Val433", Biosci Biotechnol Biochem. 2014;78(1):75-8. doi: 10.1080/09168451.2014.877186. Epub Apr. 15, 2014.
Kruse, et al., "Structure of a mutant B toxin from *Staphylococcus aureus* reveals domain swapping and conformational flexibility", Acta Crystallographica, (Apr. 1, 2011), vol. 67, No. 4, pp. 438-441, XP055535423.
Morgan, et al., "Chapter 12: Human microbiome analysis", PLOS Comput Biol. 2012;8(12):e1002808. doi: 10.1371/journal.pcbi. 1002808. Epub Dec. 27, 2012.

(Continued)

*Primary Examiner* — Christian L Fronda
(74) *Attorney, Agent, or Firm* — Foley & Lardner LLP

(57) ABSTRACT

The application provides compositions including engineered reverse transcriptases with at least one altered reverse-transcriptase related activity. The engineered reverse transcriptases or reverse transcription enzymes unexpectedly exhibit one or more altered reverse transcriptase related activities such as but not limited to altered template switching efficiency, altered transcription efficiency or both.

18 Claims, 49 Drawing Sheets

Specification includes a Sequence Listing.

(56) References Cited

OTHER PUBLICATIONS

Muotri, et al., "L1 retrotransposition in neurons is modulated by MeCP2", Nature. Nov. 18, 2010;468(7322):443-6. doi: 10.1038/nature09544.

Ram, et al., "Strategy for microbiome analysis using 16S rRNA gene sequence analysis on the Illumina sequencing platform", Syst Biol Reprod Med. Jun. 2011;57(3):162-70. doi: 10.3109/19396368.2011.555598. Epub Marl. 2011.

Skirgaila, et al., "Compartmentalization of destabilized enzyme-mRNA-ribosome complexes generated by ribosome display: a novel tool for the directed evolution of enzymes", Protein Eng Des Sel. Jul. 2013;26(7):453-61. doi: 10.1093/protein/gzt017. Epub May 10, 2013.

Wulf, et al., "Non-templated addition and template switching by Moloney murine leukemia virus (MMLV)-based reverse transcriptases co-occur and compete with each other," The American Society for Biochemistry and Molecular Biology, Inc. J. Biol. Chem (2019) 294(48) 18220-18231.

* cited by examiner

| | TIME (MINS) | 1 | | 2 | | 3 | | 4 | | 5 | | 6 | AVERAGE | STD |
|---|---|---|---|---|---|---|---|---|---|---|---|---|---|---|
| | PARAMETER | GENES | UMIs | GENES | UMIs | | | | | | | | | |
| MEDIAN GENES PER CELL | SEQ ID NO:1 | 892 | 3136 | 908 | 3208 | 887 | 2978 | 894 | 3213 | 880 | 3030 | | 892.2 3113 | 10.3357433 105.674027 |
| | AD | 733 | 2446 | | | | | | | | | | 733 2446 | #DIV/0! #DIV/0! |
| | AE | 761 | 2818 | | | | | | | | | | 761 2818 | #DIV/0! #DIV/0! |
| VALID UMIs | SEQ ID NO:1 | 99.00% | | 99.00% | | 99.00% | | 99.00% | | 99.00% | | | 99.00% #DIV/0! | 0 #DIV/0! |
| | AD | 99.00% | | 99.00% | | | | | | | | | 99.00% #DIV/0! | 0 #DIV/0! |
| | AE | 99.00% | | 100.00% | | | | | | | | | 99.50% #DIV/0! | 0.00707107 #DIV/0! |
| FRACTION RIBOSOMAL UMI | SEQ ID NO:1 | 42.10% | | 40.80% | | 41.50% | | 43.30% | | 43.50% | | | 42.24% #DIV/0! | 1.16% #DIV/0! |
| | AD | 39.70% | | | | | | | | | | | 39.70% #DIV/0! | #DIV/0! #DIV/0! |
| | AE | 45.90% | | | | | | | | | | | 45.90% #DIV/0! | #DIV/0! #DIV/0! |
| FRACTION MITOCHONDRIAL UMI | SEQ ID NO:1 | 6.50% | | 6.30% | | 6.30% | | 6.30% | | 6.40% | | | 6.36% #DIV/0! | 0.09% #DIV/0! |
| | AD | 9.10% | | | | | | | | | | | 9.10% #DIV/0! | #DIV/0! #DIV/0! |
| | AE | 6.00% | | | | | | | | | | | 6.00% #DIV/0! | #DIV/0! #DIV/0! |

FIG. 13E

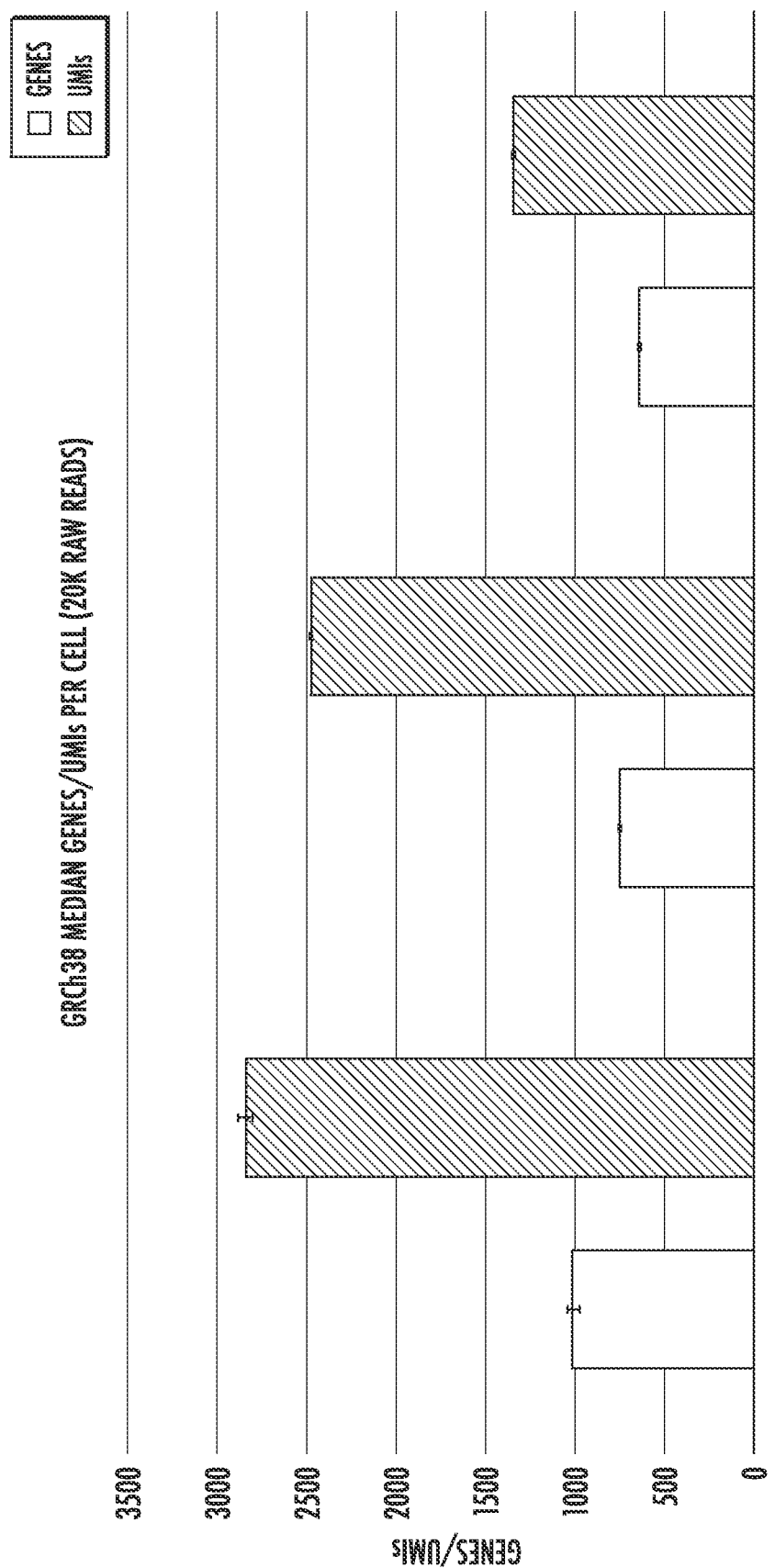

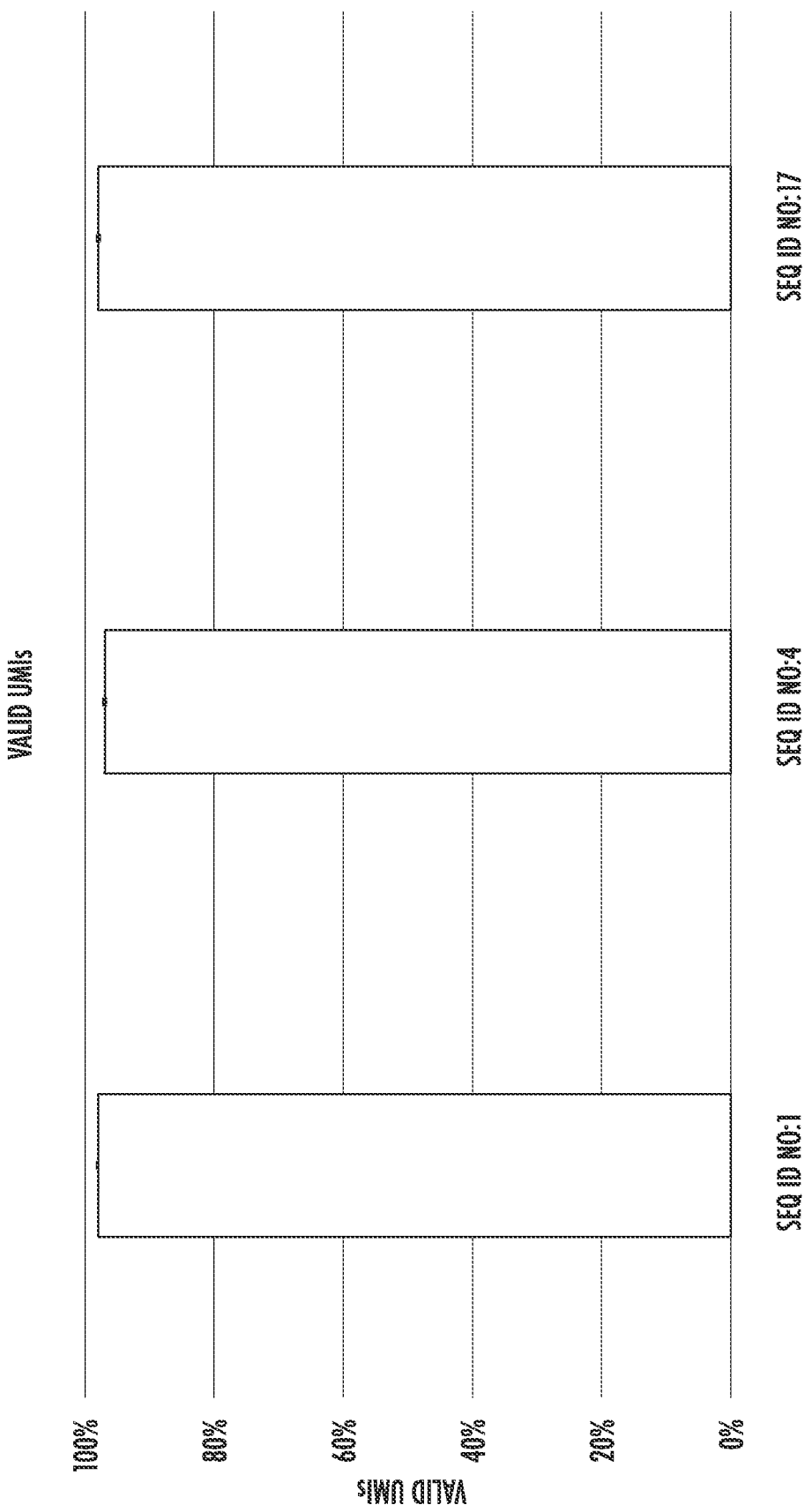

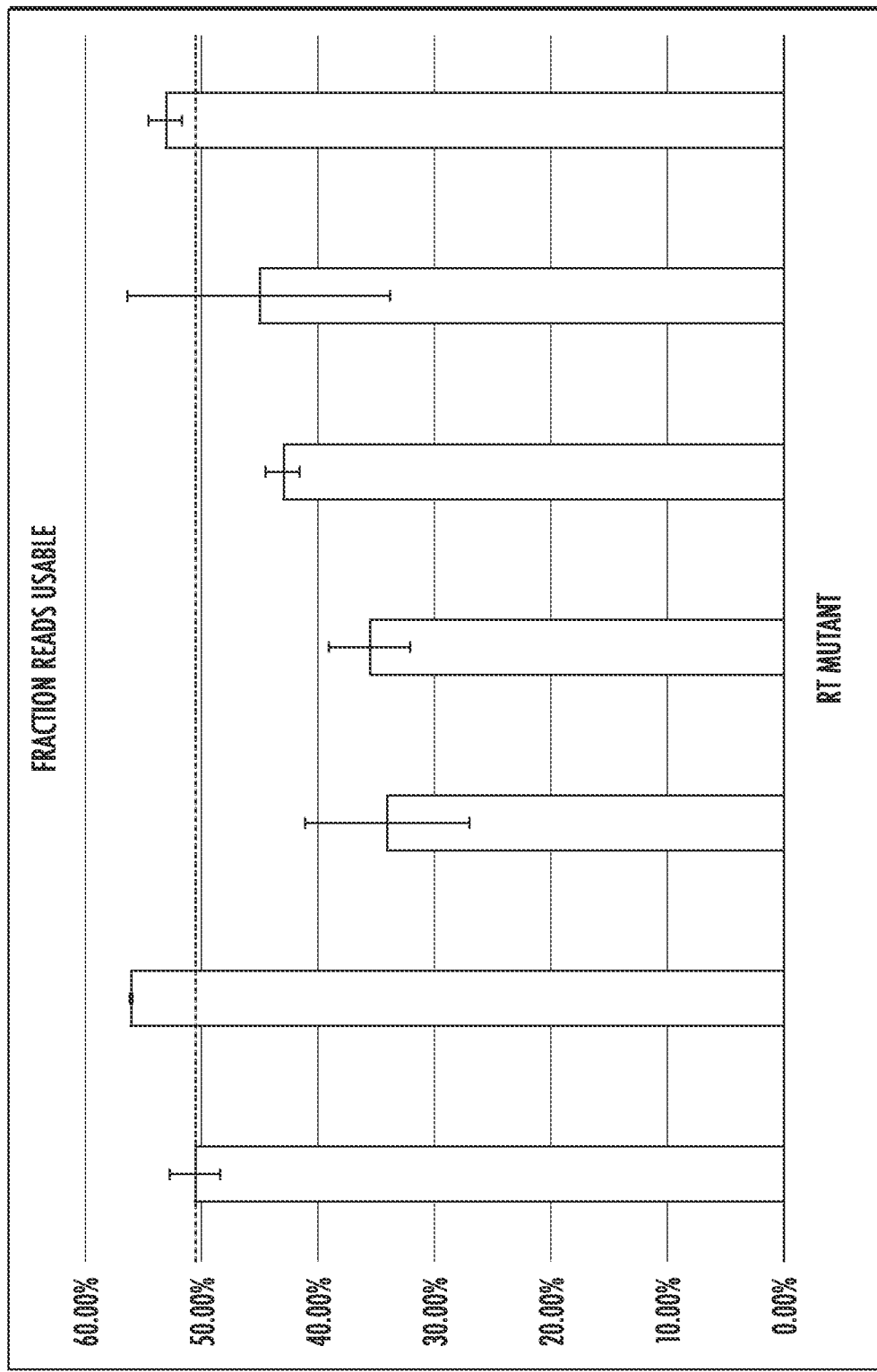

| | SEQ ID NO: 1 | MEDIAN GENES PER CELL (20K) | | MEDIAN UMIs PER CELL (20K) | |
|---|---|---|---|---|---|
| GEX | AY | 1553 | - | 3984 | - |
| | AB | 1478 | -4.83% | 3869 | -2.89% |
| | AY | 1625 | 4.64% | 4264 | 7.03% |
| | AC | 1420 | -8.56% | 3596 | -9.74% |
| | SEQ ID NO: 1 | MEDIAN GENES PER CELL (50K) | | MEDIAN UMIs PER CELL (50K) | |
| GEX | AY | 1810 | - | 4811 | - |
| | AB | 1687 | -6.80% | 4567 | -5.07% |
| | AY | 2008 | 10.94% | 5624 | 16.90% |
| | AC | 1906 | 5.30% | 5306 | 10.29% |
| | SEQ ID NO: 1 | MEDIAN GENES PER CELL (120K) | | MEDIAN UMIs PER CELL (120K) | |
| GEX | AY | 1975 | - | 5882 | - |
| | AB | 1814 | -8.15% | 5294 | -10.00% |
| | AY | 2244 | 13.62% | 6854 | 16.52% |
| | AC | 2221 | 12.46% | 6738 | 14.55% |

| | SEQ ID NO: 1 | VALID UMIs | | RIBSOMAL UMIs | | MITOCHONDRIAL UMIs | | TRANSCRIPT COVERAGE (>1500nt) | | READS MAPPED TO TRANSCRIPTOME | |
|---|---|---|---|---|---|---|---|---|---|---|---|
| GEX | | 96.85% | | 26.10% | | 5.50% | | 43.90% | | 58.05% | |
| | AY | 96.60% | -0.25% | 28.35% | 2.25% | 5.65% | 0.15% | 41.20% | -2.70% | 59.75% | 1.70% |
| | AC | 93.15% | -3.70% | 25.20% | -0.90% | 7.00% | 1.50% | 45.55% | 1.65% | 50.60% | -7.45% |
| | AB | 86.85% | -10.00% | 25.05% | -1.05% | 7.20% | 1.70% | 45.60% | 1.70% | 36.50% | -21.55% |

FIG. 21C

| | SEQ ID NO: 1 | MEDIAN GENES PER CELL (20K) | | MEDIAN UMIs PER CELL (20K) | |
|---|---|---|---|---|---|
| GEX | AV | 1553 | - | 3984 | - |
| | AM | 1520 | -2.12% | 4016 | 0.80% |
| | AN | 1514 | -2.51% | 3988 | 0.10% |
| | AB | 1625 | 4.64% | 4264 | 7.03% |

| | SEQ ID NO: 1 | MEDIAN GENES PER CELL (50K) | | MEDIAN UMIs PER CELL (50K) | |
|---|---|---|---|---|---|
| GEX | AV | 1810 | - | 4811 | - |
| | AM | 1770 | -2.21% | 4862 | 1.06% |
| | AN | 1895 | 4.70% | 5284 | 9.83% |
| | AB | 2008 | 10.94% | 5624 | 16.90% |

| | SEQ ID NO: 1 | MEDIAN GENES PER CELL (120K) | | MEDIAN UMIs PER CELL (120K) | |
|---|---|---|---|---|---|
| GEX | AV | 1975 | - | 5882 | - |
| | AM | 1915 | -3.04% | 5826 | -0.95% |
| | AN | 2116 | 7.14% | 6418 | 9.11% |
| | AB | 2244 | 13.62% | 6854 | 16.52% |

|  | SEQ ID NO: 1 | VALID UMIs |  | RIBOSOMAL UMIs |  | MITOCHONDRIAL UMIs |  | TRANSCRIPT COVERAGE (>1500nt) |  | READS MAPPED TO TRANSCRIPTOME |  |
|---|---|---|---|---|---|---|---|---|---|---|---|
| GEX | SEQ ID NO: 1 | 96.85% | , | 26.10% | , | 5.50% | , | 43.90% | , | 58.05% | , |
|  | AV | 95.95% | -0.90% | 28.10% | 2.00% | 5.55% | 0.05% | 41.50% | -2.40% | 60.00% | 1.95% |
|  | AM | 93.80% | -3.05% | 26.50% | 0.40% | 6.95% | 1.45% | 45.25% | 1.35% | 46.00% | -12.05% |
|  | AB | 93.15% | -3.70% | 25.20% | -0.90% | 7.00% | 1.50% | 45.55% | 1.65% | 50.60% | -7.45% |

FIG. 23B

SEQUENCE LISTING

```
<160> NUMBER OF SEQ ID NOS: 23

<210> SEQ ID NO 1
<211> LENGTH: 661
<212> TYPE: PRT
<213> ORGANISM: Artificial Sequence
<220> FEATURE:
<223> OTHER INFORMATION: Description of Artificial Sequence: Synthetic
      Engineered Reverse Transcriptase
```

<400> SEQUENCE: 1

```
Met Thr Trp Leu Ser Asp Phe Pro Gln Ala Trp Ala Glu Thr Gly Gly
1               5                   10                  15

Met Gly Leu Ala Val Arg Gln Ala Pro Leu Ile Ile Pro Leu Lys Ala
            20                  25                  30

Thr Ser Thr Pro Val Ser Ile Lys Gln Tyr Pro Met Ser Gln Lys Ala
        35                  40                  45

Arg Leu Gly Ile Lys Pro His Ile Gln Arg Leu Leu Asp Gln Gly Ile
    50                  55                  60

Leu Val Pro Cys Gln Ser Pro Trp Asn Thr Pro Leu Leu Pro Val Lys
65                  70                  75                  80

Lys Pro Gly Thr Asn Asp Tyr Arg Pro Val Gln Asp Leu Arg Glu Val
                85                  90                  95

Asn Lys Arg Val Glu Asp Ile His Pro Thr Val Pro Asn Pro Tyr Asn
            100                 105                 110

Leu Leu Ser Gly Pro Pro Ser His Gln Trp Tyr Thr Val Leu Asp
        115                 120                 125

Leu Lys Asp Ala Phe Phe Cys Leu Arg Leu His Pro Thr Ser Gln Pro
    130                 135                 140

Leu Phe Ala Phe Glu Trp Arg Asp Pro Glu Met Gly Ile Ser Gly Gln
145                 150                 155                 160

Leu Thr Trp Thr Arg Leu Pro Gln Gly Phe Lys Asn Ser Pro Thr Leu
                165                 170                 175

Phe Asn Glu Ala Leu His Arg Asp Leu Ala Asp Phe Arg Ile Gln His
            180                 185                 190

Pro Asp Leu Ile Leu Leu Gln Tyr Val Asp Asp Leu Leu Leu Ala Ala
    195                 200                 205

Thr Ser Glu Leu Asp Cys Gln Gln Gly Thr Arg Ala Leu Leu Gln Thr
210                 215                 220

Leu Gly Asn Leu Gly Tyr Arg Ala Ser Ala Lys Lys Ala Gln Ile Cys
225                 230                 235                 240

Gln Lys Gln Val Lys Tyr Leu Gly Tyr Leu Leu Lys Glu Gly Gln Arg
                245                 250                 255

Trp Leu Thr Glu Ala Arg Lys Glu Thr Val Met Gly Gln Pro Thr Pro
            260                 265                 270

Lys Thr Pro Arg Gln Leu Arg Arg Phe Leu Gly Lys Ala Gly Phe Cys
    275                 280                 285

Arg Leu Phe Ile Pro Gly Phe Ala Glu Met Ala Ala Pro Leu Tyr Pro
    290                 295                 300

Leu Thr Lys Pro Gly Thr Leu Phe Asn Trp Gly Pro Asp Gln Gln Lys
305                 310                 315                 320

Ala Tyr Gln Glu Ile Lys Gln Ala Leu Leu Thr Ala Pro Ala Leu Gly
                325                 330                 335

Leu Pro Asp Leu Thr Lys Pro Phe Glu Leu Phe Val Asp Glu Lys Gln
            340                 345                 350

Gly Tyr Ala Lys Gly Val Leu Thr Gln Lys Leu Gly Pro Trp Arg Arg
    355                 360                 365

Pro Val Ala Tyr Leu Ser Lys Lys Leu Asp Pro Val Ala Ala Gly Trp
370                 375                 380

Pro Pro Cys Leu Arg Met Val Ala Ala Ile Ala Val Leu Thr Lys Asp
385                 390                 395                 400

Ala Gly Lys Leu Thr Met Gly Gln Pro Leu Val Ile Gly Ala Pro His
                405                 410                 415
```

```
Ala Val Glu Ala Leu Val Lys Gln Pro Ala Gly Arg Trp Leu Ser Lys
            420                 425                 430
Ala Arg Met Thr His Tyr Gln Ala Leu Leu Leu Asp Thr Asp Arg Val
            435                 440                 445
Gln Phe Gly Pro Val Val Ala Leu Asn Pro Ala Thr Leu Leu Pro Leu
        450                 455                 460
Pro Glu Glu Gly Leu Gln His Asn Cys Leu Asp Ile Leu Ala Glu Ala
465                 470                 475                 480
His Gly Thr Arg Pro Asp Leu Thr Asp Gln Pro Leu Pro Asp Ala Asp
                485                 490                 495
His Thr Trp Tyr Thr Asn Gly Ser Ser Leu Leu Gln Glu Gly Gln Arg
            500                 505                 510
Lys Ala Gly Ala Ala Val Thr Thr Glu Thr Glu Val Ile Trp Ala Lys
            515                 520                 525
Ala Leu Pro Ala Gly Thr Ser Ala Gln Arg Ala Glu Leu Ile Ala Leu
        530                 535                 540
Thr Gln Ala Leu Lys Met Ala Glu Gly Lys Lys Leu Asn Val Tyr Thr
545                 550                 555                 560
Asp Ser Arg Tyr Ala Phe Ala Thr Ala His Ile His Gly Glu Ile Tyr
                565                 570                 575
Arg Arg Arg Gly Trp Leu Thr Ser Lys Gly Lys Glu Ile Lys Asn Lys
            580                 585                 590
Asp Glu Ile Leu Ala Leu Leu Lys Ala Leu Phe Leu Pro Lys Arg Leu
        595                 600                 605
Ser Ile Ile His Cys Pro Gly His Gln Lys Gly His Ser Ala Glu Ala
        610                 615                 620
Arg Gly Asn Arg Met Ala Asp Gln Ala Ala Arg Lys Ala Ala Ile Thr
625                 630                 635                 640
Glu Thr Pro Asp Thr Ser Thr Leu Leu Ile Glu Asn Ser Ser Pro Asn
                645                 650                 655
Ser Arg Leu Ile Asn
            660

<210> SEQ ID NO 2
<211> LENGTH: 1983
<212> TYPE: DNA
<213> ORGANISM: Artificial Sequence
<220> FEATURE:
<223> OTHER INFORMATION: Description of Artificial Sequence: Synthetic
      Engineered Reverse Transcriptase

<400> SEQUENCE: 2
acttggctgt ctgatttccc tcaggcgtgg gccgaaacgg gtggcatggg tctggcagtg      60
cgtcaggcac cgctgattat tccgctgaaa gcgacgtcga ccccggtgag catcaagcaa     120
tatccgatgt cccaaaaggc gcgcttaggt attaagccgc acattcagcg tctgctggat     180
caaggtattc tggttccgtg tcagagcccg tggaataccc gcttctcccg gtgaagaaa     240 ccgggcacga acgattaccg tccagtccaa gacttgcgcg aagttaacaa gcgcgttgaa     300
gatattcacc cgaccgtccc gaacccgtac aatctgctga gcgtccgcc gccaagccac     360 caatggtaca ccgtgctgga tctgaaagat gctttcttct gtctgcgtct gcacccaacc     420
agccagcctc tgtttgcatt tgagtggcgt gaccctgaga tgggtattag cggccagctg     480
acgtggaccc gcctgccgca aggttttaag aattccccta cgctgttttg catggcgctg     540
caccgtgacc tggcggattt ccgtatccag cacccggacc tgatcttgct gcagtacgtt     600
```

```
gatgacctgt tgctggcggc gacgagcgag ctggattgcc aacagggcac ccgtgcgctg      660
ttgcagacct tgtgcaacct gggttatcgc gctagcgcga agaaagcgca gatttgccaa      720
aaacaagtta agtatctggg ctacctgtta aaggaaggcc aacgttggct gaccgaagcc      780
cgcaaagaaa ctgtcatggg tcagccgacc ccgaaaacgc cacgccaact gcgtaggttc      840
ttgggcaaag cgggtttctg ccgcctgttc atcccgggct tgccgaaaat ggcagccccg      900
ctgtatccgt tgaccaagcc gggcaccctg ttcaactggg gtccggacca gcagaaagcg      960
taccaagaaa ttaaacaagc actgctgacg gcaccggcgc tgggtctgcc ggacctgacc     1020
aagccgtttg agctgttcgt ggatgagaag caaggttacg cgaagggcgt gttgacccag     1080
aaattgggtc cgtggcgtcg tccggttgca tacctgtcca agaaactgga cccggttgct     1140
gctggttggc cgccttgcct gcgcatggtt gccgctatcg cggtgctgac taaagacgcg     1200
ggtaagctga cgatgggtca accgctggtg atcaaggcac cgcatgcagt cgaggccctt     1260
gttaagcaac cggcaggcag atggctgagc aaggcgcgta tgacgcatta ccaggcactg     1320
ctgttggaca ccgatcgtgt gcagtttggc ccggtcgttg cgctcaaccc ggcgaccctg     1380
ctgccgctcc cggaagaagg cttgcagcac aactgtttgg acatcctggc agaggcgcac     1440
ggcactcgcc cggatctgac ggaccagccg ctgccggacg ccgatcatac ctggtatacg     1500
aatggtagca gcctgttgca agagggtcag cgtaaggccg gtgccgcggt caccaccgag     1560
actgaagtga tttgggctaa agcattgcct gcgggtacca gcgcgcagcg tgccgagctg     1620
atcgcactga cccaagcgct gaaaatggct gagggtaaga aactgaatgt gtacacggat     1680
agccgttatg cctttgcgac cgcccacatt cacggcgaga tctatcgccg tcgcggctgg     1740
ctgacgtcca aaggcaaaga gatcaagaat aaagacgaaa ttctggcgct gctgaaagcg     1800
ctgttcctgc cgaaacgtct gtcgatcatc cattgcccgg tcaccagaa aggccacagc     1860 gcagaggcgc gtggtaatcg catggctgac caggctgcgc gtaaagccgc aattaccgaa     1920
accccggaca ccagcacgct gctgatcgag aatagcagcc gaacagccg tctgatcaat     1980 tga                                                                    1983
```

<210> SEQ ID NO 3
<211> LENGTH: 1983
<212> TYPE: DNA
<213> ORGANISM: Artificial Sequence
<220> FEATURE:
<223> OTHER INFORMATION: Description of Artificial Sequence: Synthetic
      Engineered Reverse Transcriptase

<400> SEQUENCE: 3

```
acttggctgt ctgatttccc tcaggtctgg gccgaaacgg gtggcatggg tctggcagtg       60
cgtcaggcac cgctgattat tccgctgaaa gcgacgtcga ccccggtgag catcaagcaa      120
tatccgatgt cccaaaaggc gcgcagaggt attaagccgc acattcagcg tctgctggat      180
caaggtattc tggttccgtg tcagagcccg tggaataccc gcttctcccc ggtgaagaaa      240
ccgggcacga acgattaccg tccagtccaa gacttgcgcg aagttaacaa gcgcgttgaa      300
gatattcacc cgaccgtccc gaacccgtac aatctgctga gcggtccgcc gccaagccac      360
caatggtaca ccgtgctgga tctgaaagat gctttcttct gtctgcgtct gcacccaacc      420
agccagcctc tgtttgcatt tgagtggcgt gaccctgaga tgggtattag cggccagctg      480
acgtggaccc gcctgccgca aggttttaag aattccccta cgctgtttaa cgaagcgctg      540
caccgtgacc tggcggattt ccgtatccag caccggacc tgatcttgct gcagtacgtt      600
```

```
gatgacctgt tgctggcggc gacgagcgag ctggattgcc aacagggcac ccgtgcgctg    660
ttgcagacct tgggtaacct gggttatcgc gctagcgcga agaaagcgca gatttgccaa    720
aaacaagtta agtatctggg ctacctgtta aaggaaggcc aacgttggct gaccgaagcc    780
cgcaaaagaa ctgtcatggg tcagccgacc ccgaaaacgc cacgccaact gcgtaagttc    840
ttgggcaaag cgggtttctg ccgcctgttc atcccgggct tgccgaaaat ggcagccccg    900
ctgtatccgt tgaccaagcc gggcaccctg ttcaactggg gtccggacca gcagaaagcg    960
taccaagaaa ttaaacaagc actgctgacg gcaccggcgc tgggtctgcc ggacctgacc   1020
aagccgtttg agctgttcgt ggatgagaag caaggttacg cgaagggcgt gttgacccag   1080
aaattgggtc gagacgtcg tccggttgca tacctgtcca agaaactgga cccggttgct   1140
gctggttggc cgccttgcct gcgcatggtt gccgctatcg cggtgctgac taaagacgcg   1200
ggtaagctga cgatgggtca accgctggtg atcagagcac cgcatgcagt cgaggcccctt   1260 gttaagcaac cggcaggcag atggctgagc aaggcgcgta tgacgcatta ccaggcactg   1320
ctgttggaca ccgatcgtgt gcagtttggc ccggtcgttg cgctcaaccc ggcgaccctg   1380
ctgccgctcc cggaagaagg cttgcagcac aactgtttgg acatcctggc agaggcgcac   1440
ggcactcgcc cggatctgac ggaccagccg ctgccggacg ccgatcatac ctggtatacg   1500
aatggtagca gcctgttgca agagggtcag cgtaaggccg gtgccgcggt caccaccgag   1560
actgaagtga tttgggctaa agcattgcct gcgggtacca gcgcgcagcg tgccgagctg   1620
atcgcactga cccaagcgct gaaaatggct gagggtaaga aactgaatgt gtacacggat   1680
agccgttatg cctttgcgac cgcccacatt cacggcgaga tctatcgccg tcgcggctgg   1740
ctgacgtcca aaggcaaaga gatcaagaat aaagacgaaa ttctggcgct gctgaaagcg   1800
ctgttcctgc cgaaacgtct gtcgatcatc cattgcccgg gtcaccagaa aggccacagc   1860
gcagaggcgc gtggtaatcg catggctgac caggctgcgc gtaaagccgc aattaccgaa   1920
accccggaca ccagcacgct gctgatcgag aatagcagcc gaacagccg tctgatcaat   1980 tga                                                                  1983
```

<210> SEQ ID NO 4
<211> LENGTH: 1983
<212> TYPE: DNA
<213> ORGANISM: Artificial Sequence
<220> FEATURE:
<223> OTHER INFORMATION: Description of Artificial Sequence: Synthetic
    Engineered Reverse Transcriptase

<400> SEQUENCE: 4

```
acttggctgt ctgatttccc tcaggtctgg gccgaaacgg gtggcatggg tctggcagtg     60
cgtcaggcac cgctgattat tccgctgaaa gcgacgtcga ccccggtgag catcaagcaa    120
tatccgatgt cccaaaaggc gcgcagaggt attaagccgc acattcagcg tctgctggat    180
caaggtattc tggttccgtg tcagagcccg tggaataccc gcttctcccc ggtgaagaaa    240
ccgggcacga acgattaccg tccagtccaa gacttgcgcg aagttaacaa gcgcgttgaa    300
gatattcacc cgaccgtccc gaacccgtac aatctgctga gcgtccgcc gccaagccac    360 caatggtaca ccgtgctgga tctgaaagat gctttcttct gtctgcgtct gcacccaacc    420
agccagcctc tgtttgcatt tgagtggcgt gaccctgaga tgggtattag cggccagctg    480
acgtggaccc gcctgccgca aggttttaag aattccccta cgctgttttg cgaagcgctg    540
caccgtgacc tggcggattt ccgtatccag cacccggacc tgatcttgct gcagtacgtt    600
```

```
gatgacctgt tgctggcggc gacgagcgag ctggattgcc aacagggcac ccgtgcgctg      660
ttgcagacct tgtgcaacct gggttatcgc gctagcgcga agaaagcgca gatttgccaa      720
aaacaagtta agtatctggg ctacctgtta aaggaaggcc aacgttggct gaccgaagcc      780
cgcaaaagaa ctgtcatggg tcagccgacc ccgaaaacgc cacgccaact gcgtaagttc      840
ttgggcaaag cgggtttctg ccgcctgttc atcccgggct tgccgaaaat ggcagccccg      900
ctgtatccgt tgaccaagcc gggcaccctg ttcaactggg gtccggacca gcagaaagcg      960
taccaagaaa ttaaacaagc actgctgacg gcaccggcgc tgggtctgcc ggacctgacc     1020
aagccgtttg agctgttcgt ggatgagaag caaggttacg cgaagggcgt gttgacccag     1080
aaattgggtc cgagacgtcg tccggttgca tacctgtcca agaaactgga cccggttgct     1140
gctggttggc cgccttgcct gcgcatggtt gccgctatcg cggtgctgac taaagacgcg     1200
ggtaagctga cgatgggtca accgctggtg atcagagcac cgcatgcagt cgaggccctt     1260
gttaagcaac cggcaggcag atggctgagc aaggcgcgta tgacgcatta ccaggcactg     1320
ctgttggaca ccgatcgtgt gcagtttggc ccggtcgttg cgctcaaccc ggcgaccctg     1380
ctgccgctcc cggaagaagg cttgcagcac aactgtttgg acatcctggc agaggcgcac     1440
ggcactcgcc cggatctgac ggaccagccg ctgccggacg ccgatcatac ctggtatacg     1500
aatggtagca gcctgttgca agagggtcag cgtaaggccg gtgccgcggt caccaccgag     1560
actgaagtga tttgggctaa agcattgcct gcgggtacca gcgcgcagcg tgccgagctg     1620
atcgcactga cccaagcgct gaaaatggct gagggtaaga aactgaatgt gtacacggat     1680
agccgttatg cctttgcgac cgcccacatt cacggcgaga tctatcgccg tcgcggctgg     1740
ctgacgtcca aaggcaaaga gatcaagaat aaagacgaaa ttctggcgct gctgaaagcg     1800
ctgttcctgc cgaaacgtct gtcgatcatc cattgcccgg gtcaccagaa aggccacagc     1860
gcagaggcgc gtggtaatcg catggctgac caggctgcgc gtaaagccgc aattaccgaa     1920 acccccggaca ccagcacgct gctgatcgag aatagcagcc gaacagccg tctgatcaat     1980 tga                                                                   1983
```

<210> SEQ ID NO 5
<211> LENGTH: 1983
<212> TYPE: DNA
<213> ORGANISM: Artificial Sequence
<220> FEATURE:
<223> OTHER INFORMATION: Description of Artificial Sequence: Synthetic
    Engineered Reverse Transcriptase

<400> SEQUENCE: 5

```
acttggctgt ctgatttccc tcaggtctgg gccgaaacgg gtggcatggg tctggcagtg       60
cgtcaggcac cgctgattat tccgctgaaa gcgacgtcga ccccggtgag catcaagcaa      120
tatccgatgt cccaaaaggc gcgcagaggt attaagccgc acattcagcg tctgctggat      180
caaggtattc tggttccgtg tcagagcccg tggaataccc gcttctcccc ggtgaagaaa      240
ccgggcacga acgattaccg tccagtccaa gacttgcgcg aagttaacaa gcgcgttgaa      300
gatattcacc cgaccgtccc gaacccgtac aatctgctga gcggtccgcc gccaagccac      360
caatggtaca ccgtgctgga tctgaaagat gctttcttct gtctgcgtct gcacccaacc      420
agccagcctc tgtttgcatt tgagtggcgt gaccctgaga tgggtattag cggccagctg      480
acgtggaccc gcctgccgca aggttttaag aattccccta cgctgtttaa catgcgcctg      540
caccgtgacc tggcggattt ccgtatccag cacccggacc tgatcttgct gcagtacgtt      600
```

```
gatgacctgt tgctggcggc gacgagcgag ctggattgcc aacagggcac ccgtgcgctg      660
ttgcagacct tgtgcaacct gggttatcgc gctagcgcga agaaagcgca gatttgccaa      720
aaacaagtta agtatctggg ctacctgtta aggaaggcc aacgttggct gaccgaagcc       780
cgcaaaagaa ctgtcatggg tcagccgacc ccgaaaacgc cacgccaact gcgtaagttc      840
ttgggcaaag cgggtttctg ccgcctgttc atcccgggct tgccgaaat ggcagccccg       900 ctgtatccgt tgaccaagcc gggcaccctg ttcaactggg gtccggacca gcagaaagcg     960
taccaagaaa ttaaacaagc actgctgacg gcaccggcgc tgggtctgcc ggacctgacc    1020
aagccgtttg agctgttcgt ggatgagaag caaggttacg cgaagggcgt gttgacccag    1080
aaattgggtc cgagacgtcg tccggttgca tacctgtcca agaaactgga cccggttgct    1140
gctggttggc cgccttgcct gcgcatggtt gccgctatcg cggtgctgac taaagacgcg    1200
ggtaagctga cgatgggtca accgctggtg atcagagcac cgcatgcagt cgaggccctt    1260
gttaagcaac cggcaggcag atggctgagc aaggcgcgta tgacgcatta ccaggcactg    1320
ctgttggaca ccgatcgtgt gcagtttggc ccggtcgttg cgctcaaccc ggcgaccctg    1380
ctgccgctcc cggaagaagg cttgcagcac aactgtttgg acatcctggc agaggcgcac    1440
ggcactcgcc cggatctgac ggaccagccg ctgccggacg ccgatcatac ctggtatacg    1500
aatggtagca gcctgttgca agagggtcag cgtaaggccg gtgccgcggt caccaccgag    1560
actgaagtga tttgggctaa agcattgcct gcgggtacca gcgcgcagcg tgccgagctg    1620
atcgcactga cccaagcgct gaaaatggct gagggtaaga aactgaatgt gtacacggat    1680
agccgttatg cctttgcgac cgcccacatt cacggcgaga tctatcgccg tcgcggctgg    1740
ctgacgtcca aaggcaaaga gatcaagaat aaagacgaaa ttctggcgct gctgaaagcg    1800
ctgttcctgc cgaaacgtct gtcgatcatc cattgcccgg gtcaccagaa aggccacagc    1860
gcagaggcgc gtggtaatcg catggctgac caggctgcgc gtaaagccgc aattaccgaa    1920 acccccggaca ccagcacgct gctgatcgag aatagcagcc gaacagccg tctgatcaat    1980 tga                                                                   1983
```

<210> SEQ ID NO 6  
<211> LENGTH: 1983  
<212> TYPE: DNA  
<213> ORGANISM: Artificial Sequence  
<220> FEATURE:  
<223> OTHER INFORMATION: Description of Artificial Sequence: Synthetic Engineered Reverse Transcriptase

<400> SEQUENCE: 6

```
acttggctgt ctgatttccc tcaggtctgg gccgaaacgg gtggcatggg tctggcagtg       60
cgtcaggcac cgctgattat tccgctgaaa gcgacgtcga ccccggtgag catcaagcaa      120
tatccgatgt cccaaaaggc gcgcagaggt attaagccgc acattcagcg tctgctggat      180
caaggtattc tggttccgtg tcagagcccg tggaataccc gcttctcccc ggtgaagaaa      240
ccgggcacga acgattaccg tccagtccaa gacttgcgcg aagttaacaa gcgcgttgaa      300
gatattcacc cgaccgtccc gaaccgtac aatctgctga gcggtccgcc gccaagccac      360
caatggtaca ccgtgctgga tctgaaagat gctttcttct gtctgcgtct gcacccaacc      420
agccagcctc tgtttgcatt tgagtggcgt gaccctgaga tgggtattag cggccagctg      480
acgtggaccc gcctgccgca aggttttaag aattccccta cgctgttttg catggcgctg      540
caccgtgacc tggcggattt ccgtatccag cacccggacc tgatcttgct gcagtacgtt      600
```

```
gatgacctgt tgctggcggc gacgagcgag ctggattgcc aacagggcac ccgtgcgctg      660
ttgcagacct tgggtaacct gggttatcgc gctagcgcga agaaagcgca gatttgccaa      720
aaacaagtta agtatctggg ctacctgtta aggaaggcc aacgttggct gaccgaagcc       780
cgcaaaagaa ctgtcatggg tcagccgacc ccgaaaacgc cacgccaact gcgtaagttc      840
ttgggcaaag cgggtttctg ccgcctgttc atcccgggct tgccgaaat ggcagccccg       900 ctgtatccgt tgaccaagcc gggcaccctg ttcaactggg gtccggacca gcagaaagcg     960
taccaagaaa ttaaacaagc actgctgacg gcaccggcgc tgggtctgcc ggacctgacc     1020
aagccgtttg agctgttcgt ggatgagaag caaggttacg cgaagggcgt gttgacccag     1080
aaattgggtc cgagacgtcg tccggttgca tacctgtcca agaaactgga cccggttgct     1140
gctggttggc cgccttgcct gcgcatggtt gccgctatcg cggtgctgac taaagacgcg     1200
ggtaagctga cgatgggtca accgctggtg atcagagcac cgcatgcagt cgaggcccct     1260
gttaagcaac cggcaggcag atggctgagc aaggcgcgta tgacgcatta ccaggcactg     1320
ctgttggaca ccgatcgtgt gcagtttggc ccggtcgttg cgctcaaccc ggcgacccctg     1380 ctgccgctcc cggaagaagg cttgcagcac aactgtttgg acatcctggc agaggcgcac     1440
ggcactcgcc cggatctgac ggaccagccg ctgccggacg ccgatcatac ctggtatacg     1500
aatggtagca gcctgttgca agagggtcag cgtaaggccg gtgccgcggt caccaccgag     1560
actgaagtga tttgggctaa agcattgcct gcgggtacca gcgcgcagcg tgccgagctg     1620
atcgcactga cccaagcgct gaaaatggct gagggtaaga aactgaatgt gtacacggat     1680
agccgttatg cctttgcgac cgcccacatt cacggcgaga tctatcgccg tcgcggctgg     1740
ctgacgtcca aaggcaaaga gatcaagaat aaagacgaaa ttctggcgct gctgaaagcg     1800
ctgttcctgc cgaaacgtct gtcgatcatc cattgcccgg gtcaccagaa aggccacagc     1860
gcagaggcgc gtggtaatcg catggctgac caggctgcgc gtaaagccgc aattaccgaa     1920
accccggaca ccagcacgct gctgatcgag aatagcagcc gaacagccg tctgatcaat     1980 tga                                                                  1983
```

<210> SEQ ID NO 7
<211> LENGTH: 1983
<212> TYPE: DNA
<213> ORGANISM: Artificial Sequence
<220> FEATURE:
<223> OTHER INFORMATION: Description of Artificial Sequence: Synthetic Engineered Reverse Transcriptase

<400> SEQUENCE: 7

```
acttggctgt ctgatttccc tcaggtctgg gccgaaacgg gtggcatggg tctggcagtg      60
cgtcaggcac cgctgattat tccgctgaaa gcgacgtcga ccccggtgag catcaagcaa     120
tatccgatgt cccaaaaggc gcgcagaggt attaagccgc acattcagcg tctgctggat     180
caaggtattc tggttccgtg tcagagcccg tggaataccc cgcttctccc ggtgaagaaa     240
ccgggcacga acgattaccg tccagtccaa gacttgcgcg aagttaacaa gcgcgttgaa     300
gatattcacc cgaccgtccc gaaccgtac aatctgctga gcgtccgcc gccaagccac       360 caatggtaca ccgtgctgga tctgaaagat gctttcttct gtctgcgtct gcacccaacc     420
agccagcctc tgtttgcatt tgagtggcgt gaccctgaga tgggtattag cggccagctg     480
acgtggaccc gcctgccgca aggttttaag aattccccta cgctgttttg catggcgctg     540
caccgtgacc tggcggattt ccgtatccag cacccggacc tgatcttgct gcagtacgtt     600
```

```
gatgacctgt tgctggcggc gacgagcgag ctggattgcc aacagggcac ccgtgcgctg      660
ttgcagacct tgtgcaacct gggttatcgc gctagcgcga agaaagcgca gatttgccaa      720
aaacaagtta agtatctggg ctacctgtta aaggaaggcc aacgttggct gaccgaagcc      780
cgcaaaagaa ctgtcatggg tcagccgacc ccgaaaacgc cacgccaact gcgtaagttc      840
ttgggcaaag cgggtttctg ccgcctgttc atcccgggct tgccgaaaat ggcagccccg      900
ctgtatccgt tgaccaagcc gggcaccctg ttcaactggg gtccggacca gcagaaagcg      960
taccaagaaa ttaaacaagc actgctgacg gcaccggcgc tgggtctgcc ggacctgacc     1020
aagccgtttg agctgttcgt ggatgagaag caaggttacg cgaagggcgt gttgacccag     1080
aaattgggtc cgagacgtcg tccggttgca tacctgtcca agaaactgga cccggttgct     1140
gctggttggc cgccttgcct gcgcatggtt gccgctatcg cggtgctgac taaagacgcg     1200
ggtaagctga cgatgggtca accgctggtg atcagagcac cgcatgcagt cgaggccctt     1260
gttaagcaac cggcaggcag atggctgagc aaggcgcgta tgacgcatta ccaggcactg     1320
ctgttggaca ccgatcgtgt gcagtttggc ccggtcgttg cgctcaaccc ggcgacccctg     1380 ctgccgctcc cggaagaagg cttgcagcac aactgtttgg acatcctggc agaggcgcac     1440
ggcactcgcc cggatctgac ggaccagccg ctgccggacg ccgatcatac ctggtatacg     1500
aatggtagca gcctgttgca agagggtcag cgtaaggccg gtgccgcggt caccaccgag     1560
actgaagtga tttgggctaa agcattgcct gcgggtacca gcgcgcagcg tgccgagctg     1620
atcgcactga cccaagcgct gaaaatggct gagggtaaga aactgaatgt gtacacggat     1680
agccgttatg cctttgcgac cgcccacatt cacggcgaga tctatcgccg tcgcggctgg     1740
ctgacgtcca aaggcaaaga gatcaagaat aaagacgaaa ttctggcgct gctgaaagcg     1800
ctgttcctgc cgaaacgtct gtcgatcatc cattgcccgg gtcaccagaa aggccacagc     1860
gcagaggcgc gtggtaatcg catggctgac caggctgcgc gtaaagccgc aattaccgaa     1920
accccggaca ccagcacgct gctgatcgag aatagcagcc gaacagccg tctgatcaat     1980 tga                                                                  1983
```

<210> SEQ ID NO 8
<211> LENGTH: 1983
<212> TYPE: DNA
<213> ORGANISM: Artificial Sequence
<220> FEATURE:
<223> OTHER INFORMATION: Description of Artificial Sequence: Synthetic
      Engineered Reverse Transcriptase

<400> SEQUENCE: 8

```
acttggctgt ctgatttccc tcaggcgtgg gccgaaacgg gtggcatggg tctggcagtg       60
cgtcaggcac cgctgattat tctgctgaaa gcgacgtcga ccccggtgag catcaagcaa      120
tatccgatga gacaaaaggc gcgcttaggt attaagccgc acattcagcg tctgctggat      180
caaggtattc tggttccgtg tcagagcccg tggaataccc gcttctcccc ggtgaagaaa      240
ccgggcacga acgattaccg tccagtccaa gacttgcgcg aagttaacaa gcgcgttgaa      300
gatattcacc cgaccgtccc gaaccgtac aatctgctga gcggtccgcc gccaagccac      360
caatggtaca ccgtgctgga tctgaaagat gctttcttct gtctgcgtct gcacccaacc      420
agccagcctc tgtttgcatt tgagtggcgt gaccctgaga tgggtattag cggccagctg      480
acgtggaccc gcctgccgca aggttttaag aattcccctg ccctgtttaa cgaagcgctg      540
agacgtgacc tggcggattt ccgtatccag cacccggacc tgatcttgct gcagtacgtt      600
```

-continued

```
gatgacctgt tgctggcggc gacgagcgag ctggattgcc aacagggcac ccgtgcgctg    660
ttgcagacct tgggtaacct gggttatcgc gctagcgcga agaaagcgca gatttgccaa    720
aaacaagtta agtatctggg ctacctgtta aaggaaggcc aacgttggct gaccgaagcc    780
cgcaaagaaa ctgtcatggg tcagccgacc ccgaaaacgc cacgccaact gcgtaggttc    840
ttgggcaaag cgggtaactg ccgcctgttc atcccgggct tgccgaaat ggcagccccg     900 ctgtatccgt tgaccaagcc gggcaccctg ttcaactggg gtccggacca gcagaaagcg    960
taccaagaaa ttaaacaagc actgctgacg gcaccggcgc tgggtctgcc ggacctgacc    1020
aagccgtttg agctgttcgt ggatgagaag caaggttacg cgaagggcgt gttgacccag    1080
aaattgggtc cgtggcgtcg tccggttgca tacctgtcca agaaactgga cccggttgct    1140
gctggttggc cgccttgcct gcgcatggtt gccgctatcg cggtgctgac taaagacgcg    1200
ggtaagctga cgatgggtca accgctggtg atcggagcac cgcatgcagt cgaggccctt    1260
gttaagcaac cggcaggcag atggctgagc aaggcgcgta tgacgcatta ccaggcactg    1320
ctgttggaca ccgatcgtgt gcagtttggc ccggtcgttg cgctcaaccc ggcgaccctg    1380
ctgccgctcc cggaagaagg cttgcagcac aactgtttgg acatcctggc agaggcgcac    1440
ggcactcgcc cggatctgac ggaccagccg ctgccggacg ccgatcatac ctggtatacg    1500
ggaggtagca gcctgttgca agagggtcag cgtaaggccg cgtgccgcggt caccaccgag   1560 actgaagtga tttgggctaa agcattgcct gcgggtacca gcgcgcagcg tgccgagctg    1620
atcgcactga cccaagcgct gaaaatggct gagggtaaga aactgaatgt gtacacgaac    1680
agccgttatg cctttgcgac cgcccacatt cagggcgaga tctatcgccg tcgcggctgg    1740
ctgacgtcca aaggcaaaga gatcaagaat aaagacgaaa ttctggcgct gctgaaagcg    1800
ctgttcctgc cgaaacgtct gtcgatcatc cattgcccgg gtcaccagaa aggccacagc    1860
gcagaggcgc gtggtaatcg catggctaac caggctgcgc gtaaagccgc aattaccgaa    1920
accccggaca ccagcacgct gcccatcgag aatagcagcc cgaacagccg tctgatcaat    1980
tga                                                                 1983
```

<210> SEQ ID NO 9
<211> LENGTH: 1983
<212> TYPE: DNA
<213> ORGANISM: Artificial Sequence
<220> FEATURE:
<223> OTHER INFORMATION: Description of Artificial Sequence: Synthetic
    Engineered Reverse Transcriptase

<400> SEQUENCE: 9

```
acttggctgt ctgatttccc tcaggcgtgg gccgaaacgg gtggcatggg tctggcagtg    60
cgtcaggcac cgctgattat tctgctgaaa gcgacgtcga ccccggtgag catcaagcaa    120
tatccgatga caaaaggc gcgcttaggt attaagccgc acattcagcg tctgctggat     180
caaggtattc tggttccgtg tcagagcccg tggaataccc gcttctcccc ggtgaagaaa    240
ccgggcacga acgattaccg tccagtccaa gacttgcgcg aagttaacaa gcgcgttgaa    300
gatattcacc cgaccgtccc gaaccgtac aatctgctga gcgtccgcc gccaagccac      360 caatggtaca ccgtgctgga tctgaaagat gctttcttct gtctgcgtct gcacccaacc    420
agccagcctc tgtttgcatt tgagtggcgt gaccctgaga tgggtattag cggccagctg    480
acgtggaccc gcctgccgca aggttttaag aattcccctg ccctgttttg cgaagcgctg    540
agacgtgacc tggcggattt ccgtatccag cacccggacc tgatcttgct gcagtacgtt    600
```

```
gatgacctgt tgctggcggc gacgagcgag ctggattgcc aacagggcac ccgtgcgctg      660
ttgcagacct tgggtaacct gggttatcgc gctagcgcga agaaagcgca gatttgccaa      720
aaacaagtta agtatctggg ctacctgtta aggaaggcc aacgttggct gaccgaagcc       780
cgcaaagaaa ctgtcatggg tcagccgacc ccgaaaacgc cacgccaact gcgtaggttc      840
ttgggcaaag cgggtaactg ccgcctgttc atcccgggct tgccgaaat ggcagccccg       900 ctgtatccgt tgaccaagcc gggcaccctg ttcaactggg gtccggacca gcagaaagcg     960
taccaagaaa ttaaacaagc actgctgacg gcaccggcgc tgggtctgcc ggacctgacc     1020
aagccgtttg agctgttcgt ggatgagaag caaggttacg cgaagggcgt gttgacccag    1080
aaattgggtc cgtggcgtcg tccggttgca tacctgtcca agaaactgga cccggttgct    1140
gctggttggc cgccttgcct gcgcatggtt gccgctatcg cggtgctgac taaagacgcg    1200
ggtaagctga cgatgggtca accgctggtg atcggagcac cgcatgcagt cgaggcccctt  1260 gttaagcaac cggcaggcag atggctgagc aaggcgcgta tgacgcatta ccaggcactg    1320
ctgttggaca ccgatcgtgt gcagtttggc ccggtcgttg cgctcaaccc ggcgaccctg    1380
ctgccgctcc cggaagaagg cttgcagcac aactgtttgg acatcctggc agaggcgcac    1440
ggcactcgcc cggatctgac ggaccagccg ctgccggacg ccgatcatac ctggtatacg    1500
ggaggtagca gcctgttgca agagggtcag cgtaaggccg gtgccgcggt caccaccgag    1560
actgaagtga tttgggctaa agcattgcct gcgggtacca gcgcgcagcg tgccgagctg    1620
atcgcactga cccaagcgct gaaaatggct gagggtaaga aactgaatgt gtacacgaac    1680
agccgttatg cctttgcgac cgcccacatt cagggcgaga tctatcgccg tcgcggctgg    1740
ctgacgtcca aaggcaaaga gatcaagaat aaagacgaaa ttctggcgct gctgaaagcg    1800
ctgttcctgc cgaaacgtct gtcgatcatc cattgcccgg gtcaccagaa aggccacagc    1860
gcagaggcgc gtggtaatcg catggctaac caggctgcgc gtaaagccgc aattaccgaa    1920
accccggaca ccagcacgct gcccatcgag aatagcagcc gaacagccg tctgatcaat    1980 tga                                                                  1983
```

<210> SEQ ID NO 10
<211> LENGTH: 1983
<212> TYPE: DNA
<213> ORGANISM: Artificial Sequence
<220> FEATURE:
<223> OTHER INFORMATION: Description of Artificial Sequence: Synthetic
      Engineered Reverse Transcriptase

<400> SEQUENCE: 10

```
acttggctgt ctgatttccc tcaggcgtgg gccgaaacgg gtggcatggg tctggcagtg      60
cgtcaggcac cgctgattat tctgctgaaa gcgacgtcga ccccggtgag catcaagcaa    120
tatccgatga acaaaaggc gcgcttaggt attaagccgc acattcagcg tctgctggat    180
caaggtattc tggttccgtg tcagagcccg tggaataccc cgcttctccc ggtgaagaaa    240
ccgggcacga acgattaccg tccagtccaa gacttgcgcg aagttaacaa gcgcgttgaa    300
gatattcacc cgaccgtccc gaaccgtac aatctgctga gcggtccgcc gccaagccac    360
caatggtaca ccgtgctgga tctgaaagat gctttcttct gtctgcgtct gcacccaacc    420
agccagcctc tgtttgcatt tgagtggcgt gaccctgaga tgggtattag cggccagctg    480
acgtggaccc gcctgccgca aggttttaag aattcccctg ccctgttttg cgaagcgctg    540
agacgtgacc tggcggattt ccgtatccag cacccggacc tgatcttgct gcagtacgtt    600
```

```
gatgacctgt tgctggcggc gacgagcgag ctggattgcc aacagggcac ccgtgcgctg      660
ttgcagacct tgtgcaacct gggttatcgc gctagcgcga agaaagcgca gatttgccaa      720
aaacaagtta agtatctggg ctacctgtta aggaaggcc aacgttggct gaccgaagcc       780
cgcaaagaaa ctgtcatggg tcagccgacc ccgaaaacgc cacgccaact gcgtaggttc      840
ttgggcaaag cgggtaactg ccgcctgttc atcccgggct tgccgaaat ggcagccccg       900 ctgtatccgt tgaccaagcc gggcaccctg ttcaactggg gtccggacca gcagaaagcg      960
taccaagaaa ttaaacaagc actgctgacg gcaccggcgc tgggtctgcc ggacctgacc     1020
aagccgtttg agctgttcgt ggatgagaag caaggttacg cgaagggcgt gttgacccag     1080
aaattgggtc cgtggcgtcg tccggttgca tacctgtcca agaaactgga cccggttgct     1140
gctggttggc cgccttgcct gcgcatggtt gccgctatcg cggtgctgac taaagacgcg     1200
ggtaagctga cgatgggtca accgctggtg atcggagcac cgcatgcagt cgaggccctt     1260
gttaagcaac cggcaggcag atggctgagc aaggcgcgta tgacgcatta ccaggcactg     1320
ctgttggaca ccgatcgtgt gcagtttggc ccggtcgttg cgctcaaccc ggcgacccctg   1380 ctgccgctcc cggaagaagg cttgcagcac aactgtttgg acatcctggc agaggcgcac     1440
ggcactcgcc cggatctgac ggaccagccg ctgccggacg ccgatcatac ctggtatacg     1500
ggaggtagca gcctgttgca agagggtcag cgtaaggccg tgccgcggt caccaccgag      1560 actgaagtga tttgggctaa agcattgcct gcgggtacca gcgcgcagcg tgccgagctg     1620
atcgcactga cccaagcgct gaaaatggct gagggtaaga aactgaatgt gtacacgaac     1680
agccgttatg cctttgcgac cgcccacatt cagggcgaga tctatcgccg tcgcggctgg     1740
ctgacgtcca aaggcaaaga gatcaagaat aaagacgaaa ttctggcgct gctgaaagcg     1800
ctgttcctgc cgaaacgtct gtcgatcatc cattgcccgg gtcaccagaa aggccacagc     1860
gcagaggcgc gtggtaatcg catggctaac caggctgcgc gtaaagccgc aattaccgaa     1920
accccggaca ccagcacgct gcccatcgag aatagcagcc gaacagccg tctgatcaat     1980 tga                                                                     1983
```

<210> SEQ ID NO 11
<211> LENGTH: 1983
<212> TYPE: DNA
<213> ORGANISM: Artificial Sequence
<220> FEATURE:
<223> OTHER INFORMATION: Description of Artificial Sequence: Synthetic
      Engineered Reverse Transcriptase

<400> SEQUENCE: 11

```
acttggctgt ctgatttccc tcaggcgtgg gccgaaacgg gtggcatggg tctggcagtg       60
cgtcaggcac cgctgattat tctgctgaaa gcgacgtcga ccccggtgag catcaagcaa      120
tatccgatga acaaaaggc gcgcttaggt attaagccgc acattcagcg tctgctggat      180
caaggtattc tggttccgtg tcagagcccg tggaataccc gcttctcccc ggtgaagaaa      240
ccgggcacga acgattaccg tccagtccaa gacttgcgcg aagttaacaa gcgcgttgaa      300
gatattcacc cgaccgtccc gaacccgtac aatctgctga gcggtccgcc gccaagccac      360
caatggtaca ccgtgctgga tctgaaagat gctttcttct gtctgcgtct gcacccaacc      420
agccagcctc tgtttgcatt tgagtggcgt gaccctgaga tgggtattag cggccagctg      480
acgtggaccc gcctgccgca aggttttaag aattcccctg ccctgtttaa cgaagcgctg      540
agacgtgacc tggcggattt ccgtatccag caccccggacc tgatcttgct gcagtacgtt      600
```

```
gatgacctgt tgctggcggc gacgagcgag ctggattgcc aacagggcac ccgtgcgctg      660
ttgcagacct tgtgcaacct gggttatcgc gctagcgcga agaaagcgca gatttgccaa      720
aaacaagtta agtatctggg ctacctgtta aggaaggcc aacgttggct gaccgaagcc       780
cgcaaagaaa ctgtcatggg tcagccgacc ccgaaaacgc cacgccaact gcgtaggttc      840
ttgggcaaag cgggtaactg ccgcctgttc atcccgggct tgccgaaat ggcagccccg       900 ctgtatccgt tgaccaagcc gggcaccctg ttcaactggg tccggacca gcagaaagcg      960 taccaagaaa ttaaacaagc actgctgacg gcaccggcgc tgggtctgcc ggacctgacc      1020
aagccgtttg agctgttcgt ggatgagaag caaggttacg cgaagggcgt gttgacccag      1080
aaattgggtc cgtggcgtcg tccggttgca tacctgtcca agaaactgga cccggttgct      1140
gctggttggc cgccttgcct gcgcatggtt gccgctatcg cggtgctgac taaagacgcg      1200
ggtaagctga cgatgggtca accgctggtg atcggagcac cgcatgcagt cgaggccctt      1260
gttaagcaac cggcaggcag atggctgagc aaggcgcgta tgacgcatta ccaggcactg      1320
ctgttggaca ccgatcgtgt gcagtttggc ccggtcgttg cgctcaaccc ggcgaccctg      1380
ctgccgctcc cggaagaagg cttgcagcac aactgtttgg acatcctggc agaggcgcac      1440
ggcactcgcc cggatctgac ggaccagccg ctgccggacg ccgatcatac ctggtatacg      1500
ggaggtagca gcctgttgca agagggtcag cgtaaggccg gtgccgcggt caccaccgag      1560
actgaagtga tttgggctaa agcattgcct gcgggtacca gcgcgcagcg tgccgagctg      1620
atcgcactga cccaagcgct gaaaatggct gagggtaaga aactgaatgt gtacacgaac      1680
agccgttatg cctttgcgac cgcccacatt cagggcgaga tctatcgccg tcgcggctgg      1740
ctgacgtcca aaggcaaaga gatcaagaat aaagacgaaa ttctggcgct gctgaaagcg      1800
ctgttcctgc cgaaacgtct gtcgatcatc cattgcccgg gtcaccagaa aggccacagc      1860
gcagaggcgc gtggtaatcg catggctaac caggctgcgc gtaaagccgc aattaccgaa      1920 acccccggaca ccagcacgct gcccatcgag aatagcagcc gaacagccg tctgatcaat      1980 tga                                                                   1983
```

<210> SEQ ID NO 12
<211> LENGTH: 1983
<212> TYPE: DNA
<213> ORGANISM: Artificial Sequence
<220> FEATURE:
<223> OTHER INFORMATION: Description of Artificial Sequence: Synthetic
      Engineered Reverse Transcriptase

<400> SEQUENCE: 12

```
acttggctgt ctgatttccc tcaggcgtgg gccgaaacgg gtggcatggg tctggcagtg      60
cgtcaggcac cgctgattat tctgctgaaa gcgacgtcga ccccggtgag catcaagcaa      120
tatccgatga gacaaaaggc gcgcttaggt attaagccgc acattcagcg tctgctggat      180
caaggtattc tggttccgtg tcagagcccg tggaataccc gcttctcccc ggtgaagaaa      240
ccgggcacga acgattaccg tccagtccaa gacttgcgcg aagttaacaa gcgcgttgaa      300
gatattcacc cgaccgtccc cgaacccgtac aatctgctga gcgtccgcc gccaagccac      360 caatggtaca ccgtgctgga tctgaaagat gctttcttct gtctgcgtct gcacccaacc      420
agccagcctc tgtttgcatt tgagtggcgt gaccctgaga tgggtattag cggccagctg      480
acgtggaccc gcctgccgca aggttttaag aattcccctg ccctgtttaa catgcgcctg      540
agacgtgacc tggcggattt ccgtatccag cacccggacc tgatcttgct gcagtacgtt      600
```

```
gatgacctgt tgctggcggc gacgagcgag ctggattgcc aacagggcac ccgtgcgctg    660
ttgcagacct tgggtaacct gggttatcgc gctagcgcga agaaagcgca gatttgccaa    720
aaacaagtta agtatctggg ctacctgtta aggaaggcc aacgttggct gaccgaagcc     780
cgcaaagaaa ctgtcatggg tcagccgacc ccgaaaacgc cacgccaact gcgtaggttc    840
ttgggcaaag cgggtaactg ccgcctgttc atcccgggct tgccgaaat ggcagccccg     900 ctgtatccgt tgaccaagcc gggcaccctg ttcaactggg gtccggacca gcagaaagcg    960
taccaagaaa ttaaacaagc actgctgacg gcaccggcgc tgggtctgcc ggacctgacc   1020
aagccgtttg agctgttcgt ggatgagaag caaggttacg cgaagggcgt gttgacccag   1080
aaattgggtc cgtggcgtcg tccggttgca tacctgtcca agaaactgga cccggttgct   1140
gctggttggc cgccttgcct gcgcatggtt gccgctatcg cggtgctgac taaagacgcg   1200
ggtaagctga cgatgggtca accgctggtg atcggagcac cgcatgcagt cgaggccctt   1260
gttaagcaac cggcaggcag atggctgagc aaggcgcgta tgacgcatta ccaggcactg   1320
ctgttggaca ccgatcgtgt gcagtttggc ccggtcgttg cgctcaaccc ggcgacccctg  1380 ctgccgctcc cggaagaagg cttgcagcac aactgtttgg acatcctggc agaggcgcac   1440
ggcactcgcc cggatctgac ggaccagccg ctgccggacg ccgatcatac ctggtatacg   1500
ggaggtagca gcctgttgca agagggtcag cgtaaggccg gtgccgcggt caccaccgag   1560
actgaagtga tttgggctaa agcattgcct gcgggtacca gcgcgcagcg tgccgagctg   1620
atcgcactga cccaagcgct gaaaatggct gagggtaaga aactgaatgt gtacacgaac   1680
agccgttatg cctttgcgac cgcccacatt cagggcgaga tctatcgccg tcgcggctgg   1740
ctgacgtcca aaggcaaaga gatcaagaat aaagacgaaa ttctggcgct gctgaaagcg   1800
ctgttcctgc cgaaacgtct gtcgatcatc cattgcccgg gtcaccagaa aggccacagc   1860
gcagaggcgc gtggtaatcg catggctaac caggctgcgc gtaaagccgc aattaccgaa   1920
accccggaca ccagcacgct gcccatcgag aatagcagcc gaacagccg tctgatcaat    1980 tga                                                                 1983
```

<210> SEQ ID NO 13
<211> LENGTH: 1983
<212> TYPE: DNA
<213> ORGANISM: Artificial Sequence
<220> FEATURE:
<223> OTHER INFORMATION: Description of Artificial Sequence: Synthetic
      Engineered Reverse Transcriptase

<400> SEQUENCE: 13

```
acttggctgt ctgatttccc tcaggcgtgg gccgaaacgg gtggcatggg tctggcagtg     60
cgtcaggcac cgctgattat tctgctgaaa gcgacgtcga ccccggtgag catcaagcaa    120
tatccgatga gacaaaaggc gcgcttaggt attaagccgc acattcagcg tctgctggat    180
caaggtattc tggttccgtg tcagagcccg tggaataccc gcttctcccc ggtgaagaaa    240
ccgggcacga acgattaccg tccagtccaa gacttgcgcg aagttaacaa gcgcgttgaa    300
gatattcacc cgaccgtccc gaacccgtac aatctgctga gcggtccgcc gccaagccac    360
caatggtaca ccgtgctgga tctgaaagat gctttcttct gtctgcgtct gcacccaacc    420
agccagcctc tgttttgcatt tgagtggcgt gaccctgaga tgggtattag cggccagctg    480
acgtggaccc gcctgccgca aggttttaag aattcccctg ccctgtttaa catgcgctg     540 agacgtgacc tggcggattt ccgtatccag cacccggacc tgatcttgct gcagtacgtt    600
```

```
gatgacctgt tgctggcggc gacgagcgag ctggattgcc aacagggcac ccgtgcgctg      660
ttgcagacct tgtgcaacct gggttatcgc gctagcgcga agaaagcgca gatttgccaa      720
aaacaagtta agtatctggg ctacctgtta aaggaaggcc aacgttggct gaccgaagcc      780
cgcaaagaaa ctgtcatggg tcagccgacc ccgaaaacgc cacgccaact gcgtaggttc      840
ttgggcaaag cgggtaactg ccgcctgttc atcccgggct tgccgaaaat ggcagccccg      900
ctgtatccgt tgaccaagcc gggcaccctg ttcaactggg gtccggacca gcagaaagcg      960
taccaagaaa ttaaacaagc actgctgacg gcaccggcgc tgggtctgcc ggacctgacc     1020
aagccgtttg agctgttcgt ggatgagaag caaggttacg cgaagggcgt gttgacccag     1080
aaattgggtc cgtggcgtcg tccggttgca tacctgtcca agaaactgga cccggttgct     1140
gctggttggc cgccttgcct gcgcatggtt gccgctatcg cggtgctgac taaagacgcg     1200
ggtaagctga cgatgggtca accgctggtg atcggagcac cgcatgcagt cgaggccctt     1260
gttaagcaac cggcaggcag atggctgagc aaggcgcgta tgacgcatta ccaggcactg     1320
ctgttggaca ccgatcgtgt gcagtttggc ccggtcgttg cgctcaaccc ggcgaccctg     1380
ctgccgctcc cggaagaagg cttgcagcac aactgtttgg acatcctggc agaggcgcac     1440
ggcactcgcc cggatctgac ggaccagccg ctgccggacg ccgatcatac ctggtatacg     1500
ggaggtagca gcctgttgca agagggtcag cgtaaggccg gtgccgcggt caccaccgag     1560
actgaagtga tttgggctaa agcattgcct gcgggtacca gcgcgcagcg tgccgagctg     1620
atcgcactga cccaagcgct gaaaatggct gagggtaaga aactgaatgt gtacacgaac     1680
agccgttatg cctttgcgac cgcccacatt cagggcgaga tctatcgccg tcgcggctgg     1740
ctgacgtcca aaggcaaaga gatcaagaat aaagacgaaa ttctggcgct gctgaaagcg     1800
ctgttcctgc cgaaacgtct gtcgatcatc cattgcccgg gtcaccagaa aggccacagc     1860
gcagaggcgc gtggtaatcg catggctaac caggctgcgc gtaaagccgc aattaccgaa     1920
accccggaca ccagcacgct gcccatcgag aatagcagcc gaacagccg tctgatcaat     1980 tga                                                                   1983
```

<210> SEQ ID NO 14
<211> LENGTH: 1983
<212> TYPE: DNA
<213> ORGANISM: Artificial Sequence
<220> FEATURE:
<223> OTHER INFORMATION: Description of Artificial Sequence: Synthetic
      Engineered Reverse Transcriptase

<400> SEQUENCE: 14

```
acttggctgt ctgatttccc tcaggcgtgg gccgaaacgg gtggcatggg tctggcagtg       60
cgtcaggcac cgctgattat tctgctgaaa gcgacgtcga ccccggtgag catcaagcaa      120
tatccgatga gacaaaaggc gcgcttaggt attaagccgc acattcagcg tctgctggat      180
caaggtattc tggttccgtg tcagagcccg tggaataccc cgcttctccc ggtgaagaaa      240
ccgggcacga acgattaccg tccagtccaa gacttgcgcg aagttaacaa gcgcgttgaa      300
gatattcacc cgaccgtccc gaaccccgtac aatctgctga gcggtccgcc gccaagccac      360
caatggtaca ccgtgctgga tctgaaagat gctttcttct gtctgcgtct gcacccaacc      420
agccagcctc tgtttgcatt tgagtggcgt gaccctgaga tgggtattag cggccagctg      480
acgtggaccc gcctgccgca aggttttaag aattcccctg ccctgttttg catgcgcgctg      540 agacgtgacc tggcggattt ccgtatccag caccccggacc tgatcttgct gcagtacgtt      600
```

```
gatgacctgt tgctggcggc gacgagcgag ctggattgcc aacagggcac ccgtgcgctg      660
ttgcagacct tgtgcaacct gggttatcgc gctagcgcga agaaagcgca gatttgccaa      720
aaacaagtta agtatctggg ctacctgtta aaggaaggcc aacgttggct gaccgaagcc      780
cgcaaagaaa ctgtcatggg tcagccgacc ccgaaaacgc cacgccaact gcgtaggttc      840
ttgggcaaag cgggtaactg ccgcctgttc atcccgggct tgccgaaat ggcagccccg       900 ctgtatccgt tgaccaagcc gggcaccctg ttcaactggg gtccggacca gcagaaagcg     960
taccaagaaa ttaaacaagc actgctgacg gcaccggcgc tgggtctgcc ggacctgacc     1020
aagccgtttg agctgttcgt ggatgagaag caaggttacg cgaagggcgt gttgacccag     1080
aaattgggtc cgtggcgtcg tccggttgca tacctgtcca agaaactgga cccggttgct     1140
gctggttggc cgccttgcct gcgcatggtt gccgctatcg cggtgctgac taaagacgcg     1200
ggtaagctga cgatgggtca accgctggtg atcggagcac cgcatgcagt cgaggccctt     1260
gttaagcaac cggcaggcag atggctgagc aaggcgcgta tgacgcatta ccaggcactg     1320
ctgttggaca ccgatcgtgt gcagtttggc ccggtcgttg cgctcaaccc ggcgaccctg     1380
ctgccgctcc cggaagaagg cttgcagcac aactgtttgg acatcctggc agaggcgcac     1440
ggcactcgcc cggatctgac ggaccagccg ctgccggacg ccgatcatac ctggtatacg     1500
ggaggtagca gcctgttgca agagggtcag cgtaaggccg gtgccgcggt caccaccgag     1560
actgaagtga tttgggctaa agcattgcct gcgggtacca gcgcgcagcg tgccgagctg     1620
atcgcactga cccaagcgct gaaaatggct gagggtaaga aactgaatgt gtacacgaac     1680
agccgttatg cctttgcgac cgcccacatt cagggcgaga tctatcgccg tcgcggctgg     1740
ctgacgtcca aaggcaaaga gatcaagaat aaagacgaaa ttctggcgct gctgaaagcg     1800
ctgttcctgc cgaaacgtct gtcgatcatc cattgcccgg gtcaccagaa aggccacagc     1860
gcagaggcgc gtggtaatcg catggctaac caggctgcgc gtaaagccgc aattaccgaa     1920
accccggaca ccagcacgct gcccatcgag aatagcagcc gaacagccg tctgatcaat     1980 tga                                                                   1983
```

<210> SEQ ID NO 15
<211> LENGTH: 1983
<212> TYPE: DNA
<213> ORGANISM: Artificial Sequence
<220> FEATURE:
<223> OTHER INFORMATION: Description of Artificial Sequence: Synthetic
      Engineered Reverse Transcriptase

<400> SEQUENCE: 15

```
acttggctgt ctgatttccc tcaggcgtgg gccgaaacgg gtggcatggg tctggcagtg      60
cgtcaggcac cgctgattat tctgctgaaa gcgacgtcga ccccggtgag catcaagcaa     120
tatccgatga dacaaaaggc gcgcttaggt attaagccgc acattcagcg tctgctggat     180
caaggtattc tggttccgtg tcagagcccg tggaataccc gcttctcccc ggtgaagaaa     240
ccgggcacga acgattaccg tccagtccaa gacttgcgcg aagttaacaa gcgcgttgaa     300
gatattcacc cgaccgtccc gaaccgtac aatctgctga gcgtccgcc gccaagccac      360 caatggtaca ccgtgctgga tctgaaagat gctttcttct gtctgcgtct gcacccaacc     420
agccagcctc tgtttgcatt tgagtggcgt gaccctgaga tgggtattag cggccagctg     480
acgtggaccc gcctgccgca aggttttaag aattcccctg ccctgttttg catggcgctg     540
agacgtgacc tggcggattt ccgtatccag cacccggacc tgatcttgct gcagtacgtt     600
```

```
gatgacctgt tgctggcggc gacgagcgag ctggattgcc aacagggcac ccgtgcgctg      660
ttgcagacct tgggtaacct gggttatcgc gctagcgcga agaaagcgca gatttgccaa      720
aaacaagtta agtatctggg ctacctgtta aggaaggcc aacgttggct gaccgaagcc       780
cgcaaagaaa ctgtcatggg tcagccgacc ccgaaaacgc cacgccaact gcgtaggttc      840
ttgggcaaag cgggtaactg ccgcctgttc atcccgggct tgccgaaat ggcagccccg       900 ctgtatccgt tgaccaagcc gggcaccctg ttcaactggg tccggacca gcagaaagcg      960 taccaagaaa ttaaacaagc actgctgacg gcaccggcgc tgggtctgcc ggacctgacc     1020
aagccgtttg agctgttcgt ggatgagaag caaggttacg cgaagggcgt gttgacccag     1080
aaattgggtc cgtggcgtcg tccggttgca tacctgtcca agaaactgga cccggttgct     1140
gctggttggc cgccttgcct gcgcatggtt gccgctatcg cggtgctgac taaagacgcg     1200
ggtaagctga cgatgggtca accgctggtg atcggagcac cgcatgcagt cgaggccctt     1260
gttaagcaac cggcaggcag atggctgagc aaggcgcgta tgacgcatta ccaggcactg     1320
ctgttggaca ccgatcgtgt gcagtttggc ccggtcgttg cgctcaaccc ggcgaccctg     1380
ctgccgctcc cggaagaagg cttgcagcac aactgtttgg acatcctggc agaggcgcac     1440
ggcactcgcc cggatctgac ggaccagccg ctgccggacg ccgatcatac ctggtatacg     1500
ggaggtagca gcctgttgca agagggtcag cgtaaggccg gtgccgcggt caccaccgag     1560
actgaagtga tttgggctaa agcattgcct gcgggtacca gcgcgcagcg tgccgagctg     1620
atcgcactga cccaagcgct gaaaatggct gagggtaaga aactgaatgt gtacacgaac     1680
agccgttatg cctttgcgac cgcccacatt cagggcgaga tctatcgccg tcgcggctgg     1740
ctgacgtcca aaggcaaaga gatcaagaat aaagacgaaa ttctggcgct gctgaaagcg     1800
ctgttcctgc cgaaacgtct gtcgatcatc cattgcccgg gtcaccagaa aggccacagc     1860
gcagaggcgc gtggtaatcg catggctaac caggctgcgc gtaaagccgc aattaccgaa     1920
accccggaca ccagcacgct gcccatcgag aatagcagcc gaacagccg tctgatcaat      1980 tga                                                                   1983
```

<210> SEQ ID NO 16
<211> LENGTH: 1983
<212> TYPE: DNA
<213> ORGANISM: Artificial Sequence
<220> FEATURE:
<223> OTHER INFORMATION: Description of Artificial Sequence: Synthetic
      Engineered Reverse Transcriptase

<400> SEQUENCE: 16

```
acttggctgt ctgatttccc tcaggcgtgg gccgaaacgg gtggcatggg tctggcagtg       60
cgtcaggcac cgctgattat tctgctgaaa gcgacgtcga ccccggtgag catcaagcaa      120
tatccgatga gacaaaaggc gcgcttaggt attaagccgc acattcagcg tctgctggat      180
caaggtattc tggttccgtg tcagagcccg tggaataccc cgcttctccc ggtgaagaaa      240
ccgggcacga acgattaccg tccagtccaa gacttgcgcg aagttaacaa gcgcgttgaa      300
gatattcacc cgaccgtccc gaaccgtac aatctgctga gcggtccgcc gccaagccac       360
caatggtaca ccgtgctgga tctgaaagat gctttcttct gtctgcgtct gcacccaacc     420
agccagcctc tgtttgcatt tgagtggcgt gaccctgaga tgggtattag cggccagctg     480
acgtggaccc gcctgccgca aggttttaag aattccctg ccctgtttaa cgaagcgctg       540
agacgtgacc tggcggattt ccgtatccag cacccggacc tgatcttgct gcagtacgtt     600
```

```
gatgacctgt tgctggcggc gacgagcgag ctggattgcc aacagggcac ccgtgcgctg      660
ttgcagacct tgggtaacct gggttatcgc gctagcgcga agaaagcgca gatttgccaa      720
aaacaagtta agtatctggg ctacctgtta aaggaaggcc aacgttggct gaccgaagcc      780
cgcaaagaaa ctgtcatggg tcagccgacc ccgaaaacgc cacgccaact gcgtaggttc      840
ttgggcaaag cgggtaactg ccgcctgttc atcccgggct tgccgaaat ggcagccccg       900 ctgtatccgt tgaccaagcc gggcaccctg ttcaactggg gtccggacca gcagaaagcg      960
tttcaagaac tgaaacaagc actgctgacg gcaccggcgc tgggtctgcc ggacctgacc     1020
aagccgtttg agctgttcgt ggatgagaag caaggttacg cgaagggcgt gttgacccag     1080
aaattgggtc cgtggcgtcg tccggttgca tacctgtcca agaaactgga cccggttgct     1140
gctggttggc cgccttgcct gcgcatggtt gccgctatcg cggtgctgac taaagacgcg     1200
ggtaagctga cgatgggtca accgctggtg atcggagcac cgcatgcagt cgaggcccctt    1260 gttaagcaac cggcaggcag atggctgagc aaggcgcgta tgacgcatta ccaggcactg     1320
ctgttggaca ccgatcgtgt gcagtttggc ccggtcgttg cgctcaaccc ggcgaccctg     1380
ctgccgctcc cggaagaagg cttgcagcac aactgtttgg acatcctggc agaggcgcac     1440
ggcactcgcc cggatctgac ggaccagccg ctgccggacg ccgatcatac ctggtatacg     1500
ggaggtagca gcctgttgca agagggtcag cgtaaggccg gtgccgcggt caccaccgag     1560
actgaagtga tttgggctaa agcattgcct gcgggtacca gcgcgcagcg tgccgagctg     1620
atcgcactga cccaagcgct gaaaatggct gagggtaaga aactgaatgt gtacacgaac     1680
agccgttatg cctttgcgac cgcccacatt cagggcgaga tctatcgccg tcgcggctgg     1740
ctgacgtcca aaggcaaaga gatcaagaat aaagacgaaa ttctggcgct gctgaaagcg     1800
ctgttcctgc cgaaacgtct gtcgatcatc cattgcccgg gtcaccagaa aggccacagc     1860
gcagaggcgc gtggtaatcg catggctaac caggctgcgc gtaaagccgc aattaccgaa     1920
accccggaca ccagcacgct gcccatcgag aatagcagcc gaacagccg tctgatcaat     1980 tga                                                                    1983

<210> SEQ ID NO 17
<211> LENGTH: 2043
<212> TYPE: DNA
<213> ORGANISM: Artificial Sequence
<220> FEATURE:
<223> OTHER INFORMATION: Description of Artificial Sequence: Synthetic
      Engineered Reverse Transcriptase

<400> SEQUENCE: 17
atgggtagct cacatcacca tcatcatcat tcttctggtc tggtcccacg cggcagcact       60
tggctgtctg atttccctca ggcgtgggcc gaaacgggtg gcatgggtct ggcagtgcgt      120
caggcaccgc tgattattcc gctgaaagcg acgtcgaccc cggtgagcat caagcaatat      180
ccgatgtccc aaaaggcgcg cttaggtatt aagccgcaca ttcagcgtct gctggatcaa      240
ggtattctgg ttccgtgtca gagcccgtgg aataccccgc ttctcccggt gaagaaaccg      300
ggcacgaacg attaccgtcc agtccaagac ttgcgcgaag ttaacaagcg cgttgaagat      360
attcacccga ccgtcccgaa cccgtacaat ctgctgagcg gtccgccgcc aagccaccaa      420
tggtacaccg tgctggatct gaaagatgct ttcttctgtc tgcgtctgca cccaaccagc      480
cagcctctgt ttgcatttga gtggcgtgac cctgagatgg gtattagcgg ccagctgacg      540
tggacccgcc tgccgcaagg ttttaagaat tcccctacgc tgtttaacga agcgctgcac      600
```

```
cgtgacctgg cggatttccg tatccagcac ccggacctga tcttgctgca gtacgttgat    660
gacctgttgc tggcggcgac gagcgagctg gattgccaac agggcacccg tgcgctgttg    720
cagaccttgg gtaacctggg ttatcgcgct agcgcgaaga aagcgcagat tgccaaaaa     780 caagttaagt atctgggcta cctgttaaag aaggccaac gttggctgac cgaagcccgc     840
aaagaaactg tcatgggtca gccgaccccg aaaacgccac gccaactgcg taggttcttg    900
ggcaaagcgg gtttctgccg cctgttcatc ccgggctttg ccgaaatggc agccccgctg    960
tatccgttga ccaagccggg caccctgttc aactggggtc cggaccagca gaaagcgttt   1020
caagaactga acaagcact gctgacggca ccggcgctgg gtctgccgga cctgaccaag    1080
ccgtttgagc tgttcgtgga tgagaagcaa ggttacgcga agggcgtgtt gacccagaaa   1140
ttgggtccgt ggcgtcgtcc ggttgcatac ctgtccaaga actggacccc ggttgctgct   1200
ggttggccgc cttgcctgcg catggttgcc gctatcgcgg tgctgactaa agacgcgggt   1260
aagctgacga tgggtcaacc gctggtgatc aaggcaccgc atgcagtcga ggcccttgtt   1320
aagcaaccgg caggcagatg gctgagcaag gcgcgtatga cgcattacca ggcactgctg   1380
ttggacaccg atcgtgtgca gtttggcccg gtcgttgcgc tcaacccggc gaccctgctg   1440
ccgctcccgg aagaaggctt gcagcacaac tgtttggaca tcctggcaga ggcgcacggc   1500
actcgcccgg atctgacgga ccagccgctg ccggacgccg atcatacctg gtatacgaat   1560
ggtagcagcc tgttgcaaga gggtcagcgt aaggccggtg ccgcggtcac caccgagact   1620
gaagtgattt gggctaaagc attgcctgcg ggtaccagcg cgcagcgtgc cgagctgatc   1680
gcactgaccc aagcgctgaa atggctgagg gtaagaaac tgaatgtgta cacggatagc   1740
cgttatgcct ttgcgaccgc ccacattcac ggcgagatct atcgccgtcg cggctggctg   1800
acgtccaaag gcaaagagat caagaataaa gacgaaattc tggcgctgct gaaagcgctg   1860
ttcctgccga acgtctgtc gatcatccat tgcccgggtc accagaaagg ccacagcgca   1920
gaggcgcgtg gtaatcgcat ggctgaccag gctgcgcgta aagccgcaat taccgaaacc   1980
ccggacacca gcacgctgct gatcgagaat agcagcccga cagccgtct gatcaattga   2040 taa                                                                  2043
```

<210> SEQ ID NO 18
<211> LENGTH: 671
<212> TYPE: PRT
<213> ORGANISM: Moloney murine leukemia virus

<400> SEQUENCE: 18

```
Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110
```

```
Gln Asp Leu Arg Glu Val Asn Lys Arg Val Glu Asp Ile His Pro Thr
        115                 120                 125
Val Pro Asn Pro Tyr Asn Leu Leu Ser Gly Leu Pro Ser His Gln
    130                 135                 140
Trp Tyr Thr Val Leu Asp Leu Lys Asp Ala Phe Phe Cys Leu Arg Leu
145                 150                 155                 160
His Pro Thr Ser Gln Pro Leu Phe Ala Phe Glu Trp Arg Asp Pro Glu
                165                 170                 175
Met Gly Ile Ser Gly Gln Leu Thr Trp Thr Arg Leu Pro Gln Gly Phe
            180                 185                 190
Lys Asn Ser Pro Thr Leu Phe Asp Glu Ala Leu His Arg Asp Leu Ala
        195                 200                 205
Asp Phe Arg Ile Gln His Pro Asp Leu Ile Leu Leu Gln Tyr Val Asp
    210                 215                 220
Asp Leu Leu Leu Ala Ala Thr Ser Glu Leu Asp Cys Gln Gln Gly Thr
225                 230                 235                 240
Arg Ala Leu Leu Gln Thr Leu Gly Asn Leu Gly Tyr Arg Ala Ser Ala
                245                 250                 255
Lys Lys Ala Gln Ile Cys Gln Lys Gln Val Lys Tyr Leu Gly Tyr Leu
            260                 265                 270
Leu Lys Glu Gly Gln Arg Trp Leu Thr Glu Ala Arg Lys Glu Thr Val
        275                 280                 285
Met Gly Gln Pro Thr Pro Lys Thr Pro Arg Gln Leu Arg Glu Phe Leu
    290                 295                 300
Gly Thr Ala Gly Phe Cys Arg Leu Trp Ile Pro Gly Phe Ala Glu Met
305                 310                 315                 320
Ala Ala Pro Leu Tyr Pro Leu Thr Lys Thr Gly Thr Leu Phe Asn Trp
                325                 330                 335
Gly Pro Asp Gln Gln Lys Ala Tyr Gln Glu Ile Lys Gln Ala Leu Leu
            340                 345                 350
Thr Ala Pro Ala Leu Gly Leu Pro Asp Leu Thr Lys Pro Phe Glu Leu
        355                 360                 365
Phe Val Asp Glu Lys Gln Gly Tyr Ala Lys Gly Val Leu Thr Gln Lys
    370                 375                 380
Leu Gly Pro Trp Arg Arg Pro Val Ala Tyr Leu Ser Lys Lys Leu Asp
385                 390                 395                 400
Pro Val Ala Ala Gly Trp Pro Pro Cys Leu Arg Met Val Ala Ala Ile
                405                 410                 415
Ala Val Leu Thr Lys Asp Ala Gly Lys Leu Thr Met Gly Gln Pro Leu
            420                 425                 430
Val Ile Leu Ala Pro His Ala Val Glu Ala Leu Val Lys Gln Pro Pro
        435                 440                 445
Asp Arg Trp Leu Ser Asn Ala Arg Met Thr His Tyr Gln Ala Leu Leu
    450                 455                 460
Leu Asp Thr Asp Arg Val Gln Phe Gly Pro Val Val Ala Leu Asn Pro
465                 470                 475                 480
Ala Thr Leu Leu Pro Leu Pro Glu Glu Gly Leu Gln His Asn Cys Leu
                485                 490                 495
Asp Ile Leu Ala Glu Ala His Gly Thr Arg Pro Asp Leu Thr Asp Gln
            500                 505                 510
Pro Leu Pro Asp Ala Asp His Thr Trp Tyr Thr Asp Gly Ser Ser Leu
        515                 520                 525
```

-continued

```
Leu Gln Glu Gly Gln Arg Lys Ala Gly Ala Ala Val Thr Thr Glu Thr
        530                 535                 540
Glu Val Ile Trp Ala Lys Ala Leu Pro Ala Gly Thr Ser Ala Gln Arg
545                 550                 555                 560
Ala Glu Leu Ile Ala Leu Thr Gln Ala Leu Lys Met Ala Glu Gly Lys
                565                 570                 575
Lys Leu Asn Val Tyr Thr Asp Ser Arg Tyr Ala Phe Ala Thr Ala His
            580                 585                 590
Ile His Gly Glu Ile Tyr Arg Arg Gly Leu Leu Thr Ser Glu Gly
        595                 600                 605
Lys Glu Ile Lys Asn Lys Asp Glu Ile Leu Ala Leu Lys Ala Leu
    610                 615                 620
Phe Leu Pro Lys Arg Leu Ser Ile Ile His Cys Pro Gly His Gln Lys
625                 630                 635                 640
Gly His Ser Ala Glu Ala Arg Gly Asn Arg Met Ala Asp Gln Ala Ala
                645                 650                 655
Arg Lys Ala Ala Ile Thr Glu Thr Pro Asp Thr Ser Thr Leu Leu
            660                 665                 670

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 19

His His His His His
1               5

<210> SEQ ID NO 20
<211> LENGTH: 63
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
acgaccgucg ucauguagcg uuugucggag acuccuagau cagauguccu ccuggcuacu    60
gca                                                                 63

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgactcactg acactcgc                                                 18

<210> SEQ ID NO 22
<211> LENGTH: 30
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<400> SEQUENCE: 22
aagcagtggt atcaacgcag agtacatggg                                              30

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<223> OTHER INFORMATION: See specification as filed for detailed
      description of substitutions and preferred embodiments

<400> SEQUENCE: 23
tttttttttt                                                                    10
```

REVERSE TRANSCRIPTASE VARIANTS

CROSS REFERENCE

This application is a continuation of PCT/US2020/064323 filed on Dec. 10, 2020 which claims priority to U.S. Provisional Application No. 62/946,885 filed on Dec. 11, 2019 and to U.S. Provisional Application No. 63/017,913 filed on Apr. 30, 2020, all of which are hereby incorporated by reference in their entirety.

FIELD OF INVENTION

The present invention relates to the field of protein engineering, particularly development of reverse transcriptase variants. The reverse transcriptase variants exhibit one or more improved properties of interest.

SEQUENCE LISTING INCORPORATION BY REFERENCE

The application herein incorporates by reference in its entirety the sequence listing material in the ASCII text file named "10416.026US2_SeqList.txt", created Apr. 7, 2021, and having the size of 58 kilobytes, filed with this application.

BACKGROUND

One of the major challenges in cDNA synthesis reactions is interference in cDNA synthesis from RNA secondary structures. While a higher reaction temperature can remove secondary structure from the template RNA, elevated temperatures typically lead to lower reverse-transcriptase (RT) enzyme activity without the use of an efficient, thermostable RT enzyme. Additionally, RT enzyme activity can be reduced by inhibitors, such as cell lysates and associated reagents. Wild-type (WT) Moloney Murine Leukemia Virus (MMLV) reverse-transcriptase is an RT enzyme that is typically inactivated at higher temperatures. Additionally low volume reactions negatively impact wild-type (WT) MMLV reverse-transcriptase activity. Specific residues of MMLV have been linked to thermostability. M39V, M66L, E69K, E302R, T306K, W313F, L/K435G, and N454K sites have been shown to improve thermostability, see Arezi et al (2009) *Nucleic Acids Res.* 37(2):473-481, U.S. Pat. No. 7,078,208, and Baranauskas et al 2012 *Prot Engineering* 25(10): 657-668.

A wide variety of different applications of single cell processing and analysis methods and systems are known in the art, including analysis of specific individual cells, analysis of different cell types within populations of differing cell types, analysis and characterization of large populations of cells for environmental, human health, epidemiological forensic, or any of a wide variety of different applications. However, reverse transcription of mRNA from a single cell can be inhibited when the reaction volume is less than about 1 nL. Overcoming this reaction volume effect has been a challenge.

SUMMARY

Engineered reverse transcriptases with altered reverse transcriptase-related activities are provided. In various aspects, the engineered reverse transcriptases of the current application allow improved sequencing, particularly in low volume reactions.

An embodiment of the application provides an engineered reverse transcriptase comprising an amino acid sequence that is at least 95% identical to SEQ ID NO:1 and wherein the amino acid sequence of the engineered reverse transcriptase comprises at least one mutation indexed to SEQ ID NO:18 selected from the group comprising a M17 mutation; an A32 mutation, a M44 mutation, a M39 mutation, a K47 mutation, a P51 mutation, an M66 mutation, an S67 mutation, an E69 mutation, a L72 mutation, a W94 mutation, a K103 mutation, an R110 mutation, a P117 mutation, an L139 mutation, an F155 mutation, an N178 mutation, an E179 mutation, a T197 mutation, a D200 mutation, an E201 mutation, an H204 mutation, a Q221 mutation, a V223 mutation, a V238 mutation, a G248 mutation, a T265 mutation, an E268 mutation, an R279 mutation, an R280 mutation, a K284 mutation, a T287 mutation, a F291 mutation, an E302 mutation, a T306 mutation, a P308 mutation, an F309 mutation, a W313 mutation, a T330 mutation, a Y344 mutation, an 1347 mutation, a C387 mutation, a W388 mutation, an R389 mutation, a C409 mutation, an R411 mutation, a G413 mutation, an A426 mutation, a G427 mutation, a K435 mutation, an L435K mutation, an L435G mutation, an L435 mutation, a P448 mutation, a D449 mutation, an R450 mutation, a n N454 mutation, an A480 mutation, an H481 mutation, an N502 mutation, an A502 mutation, an H503 mutation, a N524 mutation, a D524 mutation, an H572 mutation, a W581 mutation, a D583 mutation, a K585 mutation, an H594 mutation, an L603 mutation, an E607 mutation, an H612 mutation, a P614 mutation, a G615 mutation, an H634 mutation, a P636 mutation, a G637 mutation, an H638 mutation, a D653 mutation, and an L671 mutation wherein the position is indexed to wild-type MMLV (SEQ ID NO:18); and wherein the engineered reverse transcriptase exhibits an altered reverse transcriptase related activity as compared to a reverse transcriptase having the amino acid sequence set forth in SEQ ID NO:1.

An embodiment of the invention provides an engineered reverse transcriptase comprising an amino acid sequence that is at least 95% identical to SEQ ID NO:1 and wherein said amino acid sequence comprises at least one mutation indexed to SEQ ID NO:18 and selected from the group comprising an A32 mutation, a M39 mutation, a P51 mutation, a M66 mutation, an S67 mutation, an E69 mutation, an L72 mutation, a W94 mutation, a K103 mutation, a R110 mutation, an L139 mutation, a T197 mutation, a D200 mutation, an E201 mutation, an H204 mutation, a Q221 mutation, a V223 mutation, a V238 mutation, a G248 mutation, an E286 mutation, a T287 mutation, an E302 mutation, a T306 mutation, a F309 mutation, W313 mutation, a T330 mutation, a W388, a C409 mutation, an R411 mutation, an L435G mutation, an L435K mutation, a K435 mutation, a P448 mutation, a D449 mutation, an R450 mutation, an N454 mutation, an A502 mutation, an H503 mutation, an N524 mutation, a D583 mutation, an H594 mutation, an L603 mutation, an E607 mutation, an H634 mutation, a P636 mutation, a G637 mutation, a D653 mutation, and an L671 mutation, and wherein the engineered reverse transcriptase exhibits an altered reverse transcriptase related activity as compared to a reverse transcriptase having the amino acid sequence set forth in SEQ ID NO:1.

An embodiment of the invention provides an engineered reverse transcriptase comprising an amino acid sequence that is at least 95% identical to SEQ ID NO:1 and wherein said amino acid sequence comprises at least two mutations indexed to SEQ ID NO:18 and selected from the group comprising an A32 mutation, a M39 mutation, a P51 mutation, a M66 mutation, an S67 mutation, an E69 mutation, an L72 mutation, a W94 mutation, a K103 mutation, a R110 mutation, an L139 mutation, a T197 mutation, a D200 mutation, an E201 mutation, an H204 mutation, a Q221 mutation, a V223 mutation, a V238 mutation, a G248 mutation, an E286 mutation, a T287 mutation, an E302 mutation, a T306 mutation, a F309 mutation, W313 mutation, a T330 mutation, a W388, a C409 mutation, an R411 mutation, an L435G mutation, an L435K mutation, an L435 mutation, a P448 mutation, a D449 mutation, an R450 mutation, an N454 mutation, an A502 mutation, an H503 mutation, an N524 mutation, a D583 mutation, an H594 mutation, an L603 mutation, an E607 mutation, an H634 mutation, a P636 mutation, a G637 mutation, a D653 mutation, and an L671 mutation, and wherein the engineered reverse transcriptase exhibits an altered reverse transcriptase related activity as compared to a reverse transcriptase having the amino acid sequence set forth in SEQ ID NO:1.

In various aspects, the at least one mutation of the engineered reverse transcriptase is selected from the group comprising an A32V mutation, an M39V mutation, a P51L mutation, an M66L mutation, an S67R mutation, an E69K mutation, an L72R mutation, a T197A mutation, a D200C mutation, an E201M mutation, an E201H mutation, a V238R mutation, a G248C mutation, an E286R mutation, an E302K mutation, an F309N mutation, a W313F mutation, a T330P mutation, a W388R mutation, a C409S mutation, an L435R mutation, an L435G mutation, an N454K mutation, an R450A mutation, an N524 mutation, a D583N mutation, an H594Q mutation, an H634Y mutation, a G637R mutation, a D653N mutation, and an L671P mutation.

An embodiment provides an engineered reverse transcriptase comprising an amino acid sequence that is at least 95% identical to SEQ ID NO:1 and wherein the amino acid sequence comprises at least one mutation selected from the group comprising an M39 mutation; an M66 mutation, an E201 mutation, a T287 mutation, a C409 mutation, an H503 mutation, an H594 mutation, an H634 mutation, and a G637 mutation; and wherein the engineered reverse transcription enzyme exhibits an altered reverse transcriptase related activity. In aspects the at least one mutation is selected from group comprising an M39V mutation; an M66L mutation, an E201Q mutation, a T287A mutation, a C409S mutation, an H503 mutation, an H594K mutation, an H634Y mutation, and a G637R mutation.

In various aspects, in low volume reactions the engineered reverse transcriptase yields at least 90% of median unique molecular identifier (UMI) counts per cell as compared to a low volume reaction comprising a reverse transcriptase having the amino acid sequence set forth in SEQ ID NO:1. In various aspects, the altered reverse transcriptase related activity is an increased ability to yield median UMI counts per cell in a low volume reaction as compared to a reverse transcriptase having the amino acid sequence set forth in SEQ ID NO:1. In aspects of the invention the low volume reaction is less than 1 nanoliter, less than 750 picoliters or less than 500 picoliters. In aspects, the altered reverse transcriptase related activity is an increased transcription efficiency as compared to the transcription efficiency of a reverse transcriptase having the amino acid sequence set forth in SEQ ID NO:1. In various aspects, the altered reverse transcriptase related activity is an altered, increased or decreased template switching (TSO) efficiency as compared to template switching efficiency of a reverse transcriptase having the amino acid sequence set forth in SEQ ID NO:1. In various aspects, the altered reverse transcriptase related activity is an increased ability to yield UMI reads from genes of a desired length in a 3' reverse transcription assay as compared to a reverse transcriptase having the amino acid sequence set forth in SEQ ID NO:1. In various aspects the desired length of genes is selected from the group of lengths comprising less than 500 nucleotides, between 500 and 1000 nucleotides, between 1000-1500 nucleotides and greater than 1500 nucleotides. In various aspects, the altered reverse transcriptase related activity is an increased ability to yield UMI reads from genes of a desired length in a 5' reverse transcription assay as compared to a reverse transcriptase having the amino acid sequence set forth in SEQ ID NO:1. In various aspects, the desired length is selected from the group of lengths comprising less than 500 nucleotides, between 500 and 1000 nucleotides, between 1000-1500 nucleotides, and greater than 1500 nucleotides. In aspects the altered reverse transcriptase related activity is an increased ability to yield median UMIs/cell as compared to a reaction comprising a reverse transcriptase having the amino acid sequence set forth in SEQ ID NO:1. In various aspects the altered reverse transcriptase related activity is an increased transcription efficiency and an increased template switching efficiency as compared to a reverse transcriptase having the amino acid sequence set forth in SEQ ID NO:1.

In aspects, the engineered reverse transcriptase has an amino acid sequence comprising at least two mutations indexed to SEQ ID NO:18 selected from the group comprising an M39 mutation; an M66 mutation, an E201 mutation, a T287 mutation, a C409 mutation, an H503 mutation, an H594 mutation, an H634 mutation, and a G637 mutation. In aspects the engineered reverse transcriptase has an amino acid sequence comprising at least three mutations selected from the group comprising an M39 mutation; an M66 mutation, an E201 mutation, a T287 mutation, a C409 mutation, an H503 mutation, an H594 mutation, an H634 mutation, and a G637 mutation. In other aspects the engineered reverse transcriptase has an amino acid sequence comprising at least four mutations selected from the group comprising an M39 mutation; an M66 mutation, an E201 mutation, a T287 mutation, a C409 mutation, an H503 mutation, an H594 mutation, an H634 mutation, and a G637 mutation. In other aspects the engineered reverse transcriptase has an amino acid sequence comprising at least five mutations selected from the group comprising an M39 mutation; an M66 mutation, an E201 mutation, a T287 mutation, a C409 mutation, an H503 mutation, an H594 mutation, an H634 mutation, and a G637 mutation. In further aspects, the engineered reverse transcriptase has an amino acid sequence comprising at least six mutations selected from the group comprising an M39 mutation; an M66 mutation, an E201 mutation, a T287 mutation, a C409 mutation, an H503 mutation, an H594 mutation, an H634 mutation, and a G637 mutation. In yet another aspect, the engineered reverse transcriptase has an amino acid sequence comprising at least seven mutations selected from the group comprising an M39 mutation; an M66 mutation, an E201 mutation, a T287 mutation, a C409 mutation, an H503 mutation, an H594 mutation, an H634 mutation, and a G637 mutation. In yet another aspect, the engineered reverse transcriptase has an amino acid sequence comprising at least eight mutations selected from the group comprising a M39 mutation; a M66 mutation, an E201 mutation, a T287 mutation, a C409 mutation, an H503 mutation, an H594 mutation, an H634 mutation, and a G637 mutation. In an aspect the engineered reverse transcriptase comprises an amino acid sequence encoded by a nucleotide sequence set forth in SEQ ID NO:2, SEQ ID NO:3, SEQ ID NO:4, SEQ ID NO:5, SEQ ID NO:6, SEQ ID NO: 7, SEQ ID NO: 8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17.

In an aspect, the engineered reverse transcriptase comprises an amino acid sequence that is at least 95%, 96%, 97%, 98% or 99% identical to SEQ ID NO:1, and wherein said amino acid sequence comprises at least seven mutations selected from the group comprising an M39 mutation; an M66 mutation, an E201 mutation, a T287 mutation, a C409 mutation, an H503 mutation, an H594 mutation, an H634 mutation, and a G637 mutation.

In another aspect, the amino acid sequence of the engineered reverse comprises an E69K mutation, an E302R mutation, a T306K mutation, a W313F mutation, an L435G mutation, and an N454K mutation and further comprises at least one mutation selected from the group comprising an M39V mutation, an M66L mutation, an L139P mutation, a D200N mutation, an E201Q mutation, a T287A mutation, a T330P mutation, an R411F mutation, a P448A mutation, a D449G mutation, an H503V mutation, an H594K mutation, an L603W mutation, an E607 mutation, an H634Y mutation and a G637R mutation, wherein the engineered reverse transcriptase exhibits an altered template switching (TS) efficiency as compared to the template switching efficiency of a reverse transcriptase having the amino acid sequence set forth in SEQ ID NO:1. In an aspect, the amino acid sequence of the engineered reverse transcriptase further comprises at least one mutation selected from the group consisting of an M39V mutation and an M66L mutation and at least one mutation selected from the group comprising an L139P mutation, a D200N mutation, an E201Q mutation, a T287A mutation, a T330P mutation, an R411F mutation, a P448A mutation, a D449G mutation, an H503V mutation, an H594K mutation, an L603W mutation, an E607 mutation, an H634Y mutation and a G637R mutation.

In an aspect, the application provides an engineered reverse transcriptase comprising an amino acid sequence that is at least 95% identical to SEQ ID NO:1, wherein the engineered reverse transcriptase exhibits an altered reverse transcriptase related activity, and wherein the amino acid sequence of the engineered reverse transcriptase comprises at least three mutations selected from the group consisting of an L139P mutation, a D200N mutation, a T330P mutation, an L603W mutation and an E607K mutation, and further comprises at least one mutation selected from the group consisting of an M39V mutation, an M66L mutation, an E69K mutation, an E201Q mutation, a T287A mutation, an E302R mutation, a T306K mutation, a W313F mutation, an R411F mutation, an L435G mutation, a P448A mutation, a D449G mutation, an N454K mutation, an H503V mutation, an H594K mutation, an H634Y mutation and a G637R mutation.

In an aspect, the application provides an engineered reverse transcriptase comprising an amino acid sequence that is at least 95% identical to SEQ ID NO:1, wherein the engineered reverse transcriptase exhibits an altered reverse transcriptase related activity, and wherein the amino acid sequence of the engineered reverse transcriptase comprises an L139P mutation, a D200N mutation, a T330P mutation, an L603W mutation and an E607K mutation and further comprises a combination of mutations. The further combination of mutations is selected from the group of combinations consisting of:

(a) a M39V mutation, an E69K mutation, an E302R mutation, a T306K mutation, a W313F mutation, an L435G mutation, a P448A mutation, a D449G mutation, and an N454K mutation; (AA);

(b) an M66L mutation, an E69K mutation, an E302R mutation, a T306K mutation, a W313F mutation, an L435G mutation, a P448A mutation, a D449G mutation, and an N454K mutation (AB);

(c) a M39V mutation, an M66L mutation, an E69K mutation, an E302R mutation, a T306K mutation, a W313F mutation, an L435G mutation, a P448A mutation, a D449G mutation, and an N454K mutation (AC);

(d) an E69K mutation, an E302R mutation, a T306K mutation, a W313F mutation, an N454K mutation, and an H503V mutation (AQ);

(e) a M66L mutation, an E69K mutation, an E302R mutation, a T306K mutation, a W313F mutation, an N454K mutation, an H503V mutation, and an H634Y mutation (AM);

(f) a M39V mutation, an M66L mutation, an E69K mutation, an E201Q mutation, E302R mutation, a T306K mutation, a W313F mutation, an L435G, a P448A mutation, a D449G mutation, an N454K mutation, an H503V mutation, an H594K mutation, and an H634Y mutation (AD);

(g) an E69K mutation, an E201Q mutation, a T287A mutation, E302R mutation, a T306K mutation, a W313F mutation, an L435G mutation, a P448A mutation, a D449G mutation, an N454K mutation, (AE);

(h) a M39V mutation, an M66L mutation, an E201Q mutation, a P448A mutation, a D449G mutation, an H503V mutation, an H594K mutation, and an H634Y mutation (AN);

(i) an M39V mutation, an M66L mutation, an E69K mutation, an E201Q mutation, a T287A mutation, E302R mutation, a T306K mutation, a W313F mutation, a C409S mutation, an L435G mutation, a P448A mutation, a D449G mutation, an N454K mutation, an H503V mutation, an H594K mutation, and an H634Y mutation (AF);

(j) an E69K mutation, an E201Q mutation, a T287A mutation, E302R mutation, a T306K mutation, a W313F mutation, a C409S mutation, an L435G mutation, a P448A mutation, a D449G mutation, an N454K mutation, and an H634Y mutation (AG);

(k) an E69K mutation, an E201Q mutation, an E302R mutation, a T306K mutation, a W313F mutation, an L435G mutation, a P448A mutation, a D449G mutation, and an N454K mutation, (AH);

(l) an E69K mutation, a T287A mutation, an E302R mutation, a T306K mutation, a W313F mutation, an L435G mutation, a P448A mutation, a D449G mutation, and an N454K mutation (AI);

(m) an H503V mutation and an H634Y mutation (AR);

(n) an M39V mutation, an M66L mutation, an E201Q mutation, a T287A mutation, P448A mutation, a D449G mutation, an H503V mutation, an H594K mutation, and an H634Y mutation (AO);

(o) an E69K mutation, an E201Q mutation, a T287A mutation, an E302R mutation, a T306K mutation, a W313F mutation, an L435G mutation, a P448A mutation, a D449G mutation, an N454K mutation, and an H634Y mutation (AJ);

(p) an M39V mutation, an M66L mutation, an E201Q mutation, a T287A mutation, a P448A mutation, a D449G mutation, an H503V mutation, an H594K mutation, an H634Y mutation, a P636H mutation (AP);

(q) an E69K mutation, an E201Q mutation, a T287A mutation, an E302R mutation, a T306K mutation, a W313F mutation, an L435G mutation, a P448A mutation, a D449G mutation, an N454K mutation, an H503V mutation, an H594K mutation, and an H634Y mutation (AK);
(r) an M39V mutation, an M66L mutation an E69K mutation, an E201Q mutation, a T287A mutation, an E302R mutation, a T306K mutation, a W313F mutation, an R411F mutation, an L435G mutation, a P448A mutation, a D449G mutation, an N454K mutation, an H503V mutation, an H594K mutation, an H634Y mutation, and a G637R mutation (AL) and
(s) an E69K mutation, an E302R mutation, a T306K mutation, a W313F mutation, an L435G-mutation, an N454K mutation, and an H594K mutation (AY). The variant identifier is indicated in parenthesis; see, for example, (AB) or (AY).

In various aspects, the application provides an engineered reverse transcriptase comprising an amino acid sequence that is at least 95% identical to SEQ ID NO:1, wherein the engineered reverse transcriptase exhibits an altered reverse transcriptase related activity, comprising at least two mutations selected from the recited group of mutations, wherein the amino acid sequence of the engineered reverse transcriptase comprises a combination of mutations selected from the group consisting of (a) an A32V mutation, an L72R mutation, a D200C mutation, a G248C mutation, an E286R mutation, an E302R mutation, a W388R mutation and an L435G mutation and (b) a Y344L mutation and an I347L mutation.

In an embodiment, the application provides an engineered reverse transcriptase comprising an amino acid sequence that is at least 95% identical to SEQ ID NO:1, wherein said engineered reverse transcriptase exhibits an altered reverse transcriptase activity as compared to a reverse transcriptase having the amino acid sequence set forth in SEQ ID NO:1, and wherein the amino acid sequence of the engineered reverse transcriptase comprises a combination of mutations indexed to SEQ ID NO:18 selected from the group consisting of: (i) an E69K mutation, an E302R mutation, a T306K mutation, a W313F mutation, an L435G mutation, and an N454K mutation, and further comprising at least one mutation selected from the group consisting of an M39V mutation, an M66L mutation, an L139P mutation, an F155Y mutation, a D200N mutation, an E201Q mutation, a T287A mutation, a T330P mutation, an R411F mutation, a P448A mutation, a D449G mutation, an H503V mutation, an H594K mutation, a L603W mutation, an E607K mutation, an H634Y mutation, a G637R mutation, and an H638G mutation; (ii) an L139P mutation, a D200N mutation, a T330P mutation, an L603W mutation, and an E607K mutation, and further comprising at least one mutation selected from the group consisting of an M39V mutation, an M66L mutation, an E69K mutation, an F155Y mutation, an E201Q mutation, a T287A mutation, an E302R mutation, a T306K mutation, a W313F mutation, an R411F mutation, an L435G mutation, a P448A mutation, a D449G mutation, an N454K mutation, an H503V mutation, an H594K mutation, an H634Y mutation, a G637R mutation, and an H638G mutation; (iii) an 32V mutation, an L72R mutation, a D200C mutation, a G248C mutation, an E286R mutation, an E302R mutation, a W388R mutation, and an L435G mutation; and (iv) a Y344L mutation and an I347L mutation.

In an aspect, the amino acid sequence of the engineered reverse transcriptase comprises a combination of mutations selected from the group consisting of (i) an E69K mutation, an E302R mutation, a T306K mutation, a W313F mutation, an L435G mutation, and an N454K mutation, further comprising a second combination of mutations selected from the group consisting of:
(a) a M39V mutation, an L139P mutation, a D200N mutation, a T330P mutation, a P448A mutation, a D449G mutation, an L603W mutation, and an E607K mutation (AA);
(b) an M66L mutation, an L139P mutation, a D200N mutation, a T330P mutation, a P448A mutation, a D449G mutation, an L603W mutation, and an E607K mutation (AB);
(c) an L139P mutation, a D200N mutation, a T330P mutation, an L603W mutation, and an E607K mutation (AV);
(d) an L139P mutation, a D200N mutation, a T330P mutation, a P448A mutation, a D449G mutation, an L603W mutation, an E607K mutation, and an H638G mutation (AW);
(e) a M39V mutation, an M66L mutation, an L139P mutation, a D200N mutation, a T330P mutation, a P448A mutation, a D449G mutation, an L603W mutation, and an E607K mutation (AC);
(f) a M39V mutation, an M66L mutation, an L139P mutation, a D200N mutation, an E201Q mutation, a T330P mutation, a P448A mutation, a D449G mutation, an H503V mutation, an H594K mutation, an L603W mutation, an E607K mutation, and an H634Y mutation (AD);
(g) an L139P mutation, a D200N mutation, an E201Q mutation, a T287A mutation, a T330P mutation, a P448A mutation, a D449G mutation, an L603W mutation, and an E607K mutation (AE);
(h) an M39V mutation, an M66L mutation, an L139P mutation, a D200N mutation, an E201Q mutation, a T287A mutation, a T330P mutation, a C409S mutation, a P448A mutation, a D449G mutation, an H503V mutation, an H594K mutation, an L603W mutation, an E607K mutation and an H634Y mutation (AF);
(i) an L139P mutation, a D200N mutation, an E201Q mutation, a T287A mutation, a T330P mutation, a C409S mutation, a P448A mutation, a D449G mutation, an L603W mutation, an E607K mutation and an H634Y mutation (AG);
(j) an L139P mutation, a D200N mutation, an E201Q mutation, a T330P mutation, a P448A mutation, a D449G mutation, L603W mutation, and an E607K mutation (AH);
(k) an L139P mutation, a D200N mutation, a T287A mutation, a T330P mutation, a P448A mutation, a D449G mutation, L603W mutation, and an E607K mutation (AI);
(l) an L139P mutation, a D200N mutation, an E201Q mutation, a T287A mutation, a T330P mutation, a P448A mutation, a D449G mutation, L603W mutation, an E607K mutation and an H634Y mutation (AJ);
(m) an L139P mutation, a D200N mutation, an E201Q mutation, a T287A mutation, a T330P mutation, a P448A mutation, a D449G mutation, an H503V mutation, an H594K mutation, L603W mutation, an E607K mutation, and an H634Y mutation (AK);
(n) an M39V mutation, an M66L mutation, an L139P mutation, a D200N mutation, an E201Q mutation, a T287A mutation, a T330P mutation, an R411F mutation, a P448A mutation, a D449G mutation, an H503V mutation, an H594K mutation, L603W mutation, an E607K mutation, an H634Y mutation, and a G637R mutation (AL);

(o) an L139P mutation, a D200N mutation, a T330P mutation, an H594K mutation, an L603W mutation, and an E607K mutation (AY);
(p) an L139P mutation, an F155Y mutation, a D200N mutation, a T330P mutation, a P448A mutation, a D449G mutation, an L603W mutation, an E607K mutation, and an H638G mutation (AX);
  ii. an L139P mutation, a D200N mutation, a T330P mutation, an L603W mutation, and an E607K mutation, further comprising a second combination of mutations selected from the group consisting of:
  (aa) a M39V mutation, an E69K mutation, an E302R mutation, a T306K mutation, a W313F mutation, an L435G mutation, a P448A mutation, a D449G mutation, and an N454K mutation; (AA)
  (bb) an M66L mutation, an E69K mutation, an E302R mutation, a T306K mutation, a W313F mutation, an L435G mutation, a P448A mutation, a D449G mutation, and an N454K mutation (AB);
  (cc) an E69K mutation, an E302R mutation, a T306K mutation, a W313F mutation, an L435G mutation, and an N454K mutation (AV);
  (dd) a M66L mutation, an E69K mutation, an E302R mutation, a T306K mutation, a W313F mutation, an N454K mutation, an H503V mutation, and an H634Y mutation (AM);
  (ee) an E69K mutation, an E302R mutation, a T306K mutation, a W313F mutation, an L435G mutation, a P448A mutation, a D449G mutation, an N454K mutation, and an H638G mutation (AW);
  (ff) a M39V mutation, an M66L mutation, an E69K mutation, an E302R mutation, a T306K mutation, a W313F mutation, an L435G mutation, a P448A mutation, a D449G mutation, and an N454K mutation (AC);
  (gg) a M39V mutation, an M66L mutation, an E69K mutation, an E201Q mutation, E302R mutation, a T306K mutation, a W313F mutation, an L435G mutation, a P448A mutation, a D449G mutation, an N454K mutation, an H503V mutation, an H594K mutation, and an H634Y mutation (AD);
  (hh) an E69K mutation, an E201Q mutation, a T287A mutation, E302R mutation, a T306K mutation, a W313F mutation, an L435G mutation, a P448A mutation, a D449G mutation, an N454K mutation, (AE);
  (ii) a M39V mutation, an M66L mutation, an E201Q mutation, a P448A mutation, a D449G mutation, an H503V mutation, an H594K mutation, and an H634Y mutation (AN);
  (jj) an M39V mutation, an M66L mutation, an E69K mutation, an E201Q mutation, a T287A mutation, E302R mutation, a T306K mutation, a W313F mutation, a C409S mutation, an L435G mutation, a P448A mutation, a D449G mutation, an N454K mutation, an H503V mutation, an H594K mutation, and an H634Y mutation (AF);
  (kk) an E69K mutation, an E201Q mutation, a T287A mutation, E302R mutation, a T306K mutation, a W313F mutation, a C409S mutation, an L435G mutation, a P448A mutation, a D449G mutation, an N454K mutation, and an H634Y mutation (AG);
  (ll) an E69K mutation, an E201Q mutation, an E302R mutation, a T306K mutation, a W313F mutation, an L435G mutation, a P448A mutation, a D449G mutation, and an N454K mutation, (AH);
  (mm) an E69K mutation, a T287A mutation, an E302R mutation, a T306K mutation, a W313F mutation, an L435G mutation, a P448A mutation, a D449G mutation, and an N454K mutation (AI);
  (nn) an H503V mutation and an H634Y mutation (AR);
  (oo) an M39V mutation, an M66L mutation, an E201Q mutation, a T287A mutation, P448A mutation, a D449G mutation, an H503V mutation, an H594K mutation, and an H634Y mutation (AO);
  (pp) an E69K mutation, an E201Q mutation, a T287A mutation, an E302R mutation, a T306K mutation, a W313F mutation, an L435G mutation, a P448A mutation, a D449G mutation, an N454K mutation, and an H634Y mutation (AJ);
  (qq) an M39V mutation, an M66L mutation, an E201Q mutation, a T287A mutation, a P448A mutation, a D449G mutation, an H503V mutation, an H594K mutation, an H634Y mutation, a P636H mutation (AP);
  (rr) an E69K mutation, an E201Q mutation, a T287A mutation, an E302R mutation, a T306K mutation, a W313F mutation, an L435G mutation, a P448A mutation, a D449G mutation, an N454K mutation, an H503V mutation, an H594K mutation, and an H634Y mutation (AK);
  (ss) an M39V mutation, an M66L mutation, an E69K mutation, an E201Q mutation, a T287A mutation, an E302R mutation, a T306K mutation, a W313F mutation, an R411F mutation, an L435G mutation, a P448A mutation, a D449G mutation, an N454K mutation, an H503V mutation, an H594K mutation, an H634Y mutation, and a G637R mutation (AL);
  (tt) an E69K mutation, an E302R mutation, a T306K mutation, a W313F mutation, an N454K mutation, and an H503V mutation (AQ);
  (uu) an E69K mutation, an E302R mutation, a T306K mutation, a W313F mutation, an L435G mutation, an N454K mutation, and an H594K mutation (AY); and
  (vv) an E69K mutation, an F155Y mutation, an E302R mutation, a T306K mutation, a W313F mutation, an L435G mutation, a P448A mutation, a D449G mutation, an N454K mutation, and an H638G mutation (AX). The variant indicator or identifier is provided in parenthesis.

In various aspects, the altered reverse transcriptase related activity is an altered template switching (TS) efficiency as compared to the template switching efficiency of a reverse transcriptase having the amino acid sequence set forth in SEQ ID NO:1. In other aspects, the altered reverse transcriptase activity is an increased ability to yield UMI reads from genes of a desired length in a 3' reverse transcription assay as compared to a reverse transcriptase having the amino acid sequence set forth in SEQ ID NO:1. In some aspects, the desired length of genes is selected from the group of lengths comprising less than 500 nucleotides, between 500 and 1000 nucleotides, between 1000-1500 nucleotides and greater than 1500 nucleotides. In aspects of the application, the altered reverse transcriptase related activity is an increased ability to yield UMI reads from genes of a desired length in a 5' reverse transcription assay as compared to a reverse transcriptase having the amino acid sequence set forth in SEQ ID NO:1. The desired length is selected from the group of lengths comprising less than 500 nucleotides, between 500 and 1000 nucleotides, between 1000-1500 nucleotides, and greater than 1500 nucleotides. In some aspects, the altered reverse transcriptase related activity is an increased ability to yield median UMIs/cell as compared to a reaction comprising a reverse transcriptase having the amino acid sequence set forth in SEQ ID NO:1. In aspects, the altered reverse transcriptase related activity is an increased transcription efficiency and an increased template switching efficiency as compared to a reverse transcriptase having the amino acid sequence set forth in SEQ ID NO:1. In various aspects, the altered reverse transcriptase related activity is an increased transcription efficiency as compared to the transcription efficiency of a reverse transcriptase having the amino acid sequence set forth in SEQ ID NO:1.

In various aspects, in low volume reactions the engineered reverse transcriptase yields at least 90% of median unique molecular identifier (UMI) counts per cell as compared to a low volume reaction comprising a reverse transcriptase having the amino acid sequence set forth in SEQ ID NO:1. In various aspects, the altered reverse transcriptase related activity is an increased ability to yield median UMI counts per cell in a low volume reaction as compared to a reverse transcriptase having the amino acid sequence set forth in SEQ ID NO:1. In aspects of the invention the low volume reaction is less than 1 nanoliter, less than 750 picoliters or less than 500 picoliters.

In an embodiment, the application provides an engineered reverse transcriptase comprising a combination of mutations in the amino acid sequence of SEQ ID NO:18, wherein the combination of mutations comprises E69K, L139P, D200N, E302R, T306K, W313F, T330P, L435K, P448A, D449G, N454K, D524N, L603W, E607K and one or more of A32V, M39V, M66L, L72R, L139P, F155Y, D200C, D200E, E201Q, H204R, G248C, E286R, T287A, Y344L, I347L, W388R, R411F, K435G, H503V, D583N, H594K, H594Q, L603F, E607G, H634Y, G637R, H638G, D653H, and L671P. In an aspect, the engineered reverse transcriptase comprises M66L, E69K, L139P, D200N, E302R, T306K, W313F, T330P, P448A, D449G, N454K, L603W and E607K. In an aspect, the engineered reverse transcriptase comprises E69K, L139P, D200N, E302R, T306K, W313F, T330P, P448A, D449G, N454K, H503V, L603W and E607K. In an aspect, the engineered reverse transcriptase comprises E69K, L139P, D200N, E302R, T306K, W313F, T330P, P448A, D449G, N454K, L603W, E607K and H634Y. In an aspect, an engineered reverse transcriptase comprising M66L, E69K, L139P, D200N, E302R, T306K, W313F, T330P, P448A, D449G, N454K, L603W and E607K further comprises H503V. In an aspect, an engineered reverse transcriptase comprising M66L, E69K, L139P, D200N, E302R, T306K, W313F, T330P, P448A, D449G, N454K, L603W and E607K further comprises H634Y. In an aspect, an engineered reverse transcriptase comprising M66L, E69K, L139P, D200N, E302R, T306K, W313F, T330P, P448A, D449G, N454K, L603W and E607K further comprises H503V and H634Y. In an aspect, an engineered reverse transcriptase of the application comprises a combination of mutations in the amino acid sequence of SEQ ID NO:18, wherein the combination of mutations comprises E69K, L139P, D200N, E302R, T306K, W313F, T330P, L435K, P448A, D449G, N454K, D524N, L603W, E607K and one or more of A32V, M39V, M66L, L72R, L139P, F155Y, D200C, D200E, E201Q, H204R, G248C, E286R, T287A, Y344L, I347L, W388R, R411F, K435G, H503V, D583N, H594K, H594Q, L603F, E607G, H634Y, G637R, H638G, D653H, and L671P.

In various aspects of the application, an engineered reverse transcriptase exhibits an altered reverse transcriptase related activity as compared to a reverse transcriptase having the amino acid sequence set forth in SEQ ID NO:1. In certain aspects, the altered reverse transcriptase activity is an altered template switching efficiency as compared to the template switching activity of a reverse transcriptase having the amino acid sequence set forth in SEQ ID NO:1. In some aspects, the engineered reverse transcriptase maintains reverse transcriptase activity in a low reaction volume, wherein the low reaction volume is less than 1 nanoliter, less than 750 picoliters or less than 500 picoliters. In some aspects, the low reaction volume is less than 1 nanoliter, less than 750 picoliters or less than 500 picoliters.

In an embodiment the application provides an engineered reverse transcriptase comprising a nucleic acid sequence from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17. In an aspect of the engineered reverse transcriptase, the nucleic acid sequence is SEQ ID NO:4. In an aspect of the engineered reverse transcriptase, the nucleic acid sequence is SEQ ID NO:17.

In an embodiment, a plasmid comprising a nucleic acid sequence encoding an engineered reverse transcriptase comprising a combination of mutations in the amino acid sequence of SEQ ID NO:18, wherein the combination of mutations comprises E69K, L139P, D200N, E302R, T306K, W313F, T330P, L435K, P448A, D449G, N454K, D524N, L603W, E607K and one or more of A32V, M39V, M66L, L72R, L139P, F155Y, D200C, D200E, E201Q, H204R, G248C, E286R, T287A, Y344L, I347L, W388R, R411F, K435G, H503V, D583N, H594K, H594Q, L603F, E607G, H634Y, G637R, H638G, D653H, and L671P, for expression in a host is provided. In an aspect, the application provides a plasmid comprising the nucleic acid sequence of an engineered reverse transcriptase comprising a combination of mutations in the amino acid sequence of SEQ ID NO:18, wherein the combination of mutations comprises E69K, L139P, D200N, E302R, T306K, W313F, T330P, L435K, P448A, D449G, N454K, D524N, L603W, E607K and one or more of A32V, M39V, M66L, L72R, L139P, F155Y, D200C, D200E, E201Q, H204R, G248C, E286R, T287A, Y344L, I347L, W388R, R411F, K435G, H503V, D583N, H594K, H594Q, L603F, E607G, H634Y, G637R, H638G, D653H, and L671P, wherein the plasmid can be transformed into a suitable host for expression of the engineered reverse transcriptase.

In an embodiment, the application provides methods for performing a reverse transcription reaction using an engineered reverse transcriptase of the application. An engineered reverse transcriptase of the application may comprise a combination of mutations in the amino acid sequence of SEQ ID NO:18, wherein the combination of mutations comprises E69K, L139P, D200N, E302R, T306K, W313F, T330P, L435K, P448A, D449G, N454K, D524N, L603W, E607K and one or more of A32V, M39V, M66L, L72R, L139P, F155Y, D200C, D200E, E201Q, H204R, G248C, E286R, T287A, Y344L, I347L, W388R, R411F, K435G, H503V, D583N, H594K, H594Q, L603F, E607G, H634Y, G637R, H638G, D653H, and L671P.

In an embodiment, the application provides methods for performing a template switching reaction using an engineered reverse transcriptase of the application. An engineered reverse transcriptase of the application may comprise a combination of mutations in the amino acid sequence of SEQ ID NO:18, wherein the combination of mutations comprises E69K, L139P, D200N, E302R, T306K, W313F, T330P, L435K, P448A, D449G, N454K, D524N, L603W, E607K and one or more of A32V, M39V, M66L, L72R, L139P, F155Y, D200C, D200E, E201Q, H204R, G248C, E286R, T287A, Y344L, I347L, W388R, R411F, K435G, H503V, D583N, H594K, H594Q, L603F, E607G, H634Y, G637R, H638G, D653H, and L671P.

In an aspect, the application provides an engineered reverse transcriptase wherein the engineered reverse transcriptase maintains reverse transcription activity at temperatures between about 70° C. to about 90° C. when compared to SEQ ID NO:1. An engineered reverse transcriptase of the application may comprise a combination of mutations in the amino acid sequence of SEQ ID NO:18, wherein the combination of mutations comprises E69K, L139P, D200N, E302R, T306K, W313F, T330P, L435K, P448A, D449G, N454K, D524N, L603W, E607K and one or more of A32V, M39V, M66L, L72R, L139P, F155Y, D200C, D200E, E201Q, H204R, G248C, E286R, T287A, Y344L, I347L, W388R, R411F, K435G, H503V, D583N, H594K, H594Q, L603F, E607G, H634Y, G637R, H638G, D653H, and L671P.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

FIGS. 13A-13E summarize information obtained from the SEQ ID NO:1 engineered reverse transcriptase and two engineered reverse transcriptase variants, AD and AE in gene expression assays. FIG. 13A shows the median number of genes compared to the median unique molecular identifier (UMI) per cell per engineered reverse transcriptase. Assays performed with all three engineered reverse transcriptases indicated at least 2400 UMI per cell and 99% of the UMIs were detected. UMI's (light bars) and genes (dark bars) are shown. FIG. 13B indicates comparable levels of UMI's were detected in assays with the 3 engineered reverse transcriptases. FIG. 13C indicates the fraction of ribosomal UMI's detected in assays with each engineered reverse transcriptase. FIG. 13D indicates the fraction of mitochondrial UMI's detected in assays with each engineered reverse transcriptase. FIG. 13E provides a summary of the data.

FIGS. 16A-16D summarize information obtained from the engineered reverse transcriptase with the amino acid sequence set forth in SEQ ID NO:1 and two engineered reverse transcriptase variants, encoded by the nucleotide sequences set forth in SEQ ID NO:4 and SEQ ID NO:17 in gene expression assays. FIG. 16A shows the median number of genes compared to the median unique molecular identifier (UMI) per cell per engineered reverse transcriptase. Assays performed with the variant having an amino acid sequence encoded by the nucleotide sequence set forth in SEQ ID NO:4 indicate approximately 2500 UMIs read per cell; assays performed with the variant having an amino acid sequence encoded by the nucleotide sequence set forth in SEQ ID NO:17 indicated approximately 1200 UMIs read per cell. UMI's (light bars) and genes (dark bars) are shown. A reduction in complexity is observed with both variants. FIG. 16B indicates comparable levels of UMI's were detected in assays with the 3 engineered reverse transcriptases. FIG. 16C indicates the fraction of ribosomal UMI's detected in assays with each engineered reverse transcriptase. FIG. 16D indicates the fraction of mitochondrial UMI's detected in assays with each engineered reverse transcriptase.

FIGS. 18A-18G summarize results obtained from multiple variants AG, AF, AB, AA, AH, AI and SEQ ID NO:1. FIG. 18A shows the median number of genes compared to the median unique molecular identifier (UMI) per cell per engineered reverse transcriptase. Assays performed with SEQ ID NO:1 indicate approximately 3800 UMIs read per cell. Assays performed with AG indicated approximately 3700 UMIs read per cell. Assays performed with AF indicated approximately 3000 UMIs read per cell. Assays performed with AB indicated approximately 3700 UMIs read per cell. Assays performed with AA indicated approximately 3900 UMIs read per cell. Assays performed with AH indicated approximately 2900 UMIs read per cell. Assays performed with AI indicated approximately 3700 UMIs read per cell. UMI's (light bars) and genes (dark bars) are shown. A reduction in complexity is observed with the AF and AH variants.

FIG. 18B indicates comparable levels of UMI's were detected in assays with an enzyme having the amino acid sequence set forth in SEQ ID NO:1, AG, AH and AI; while slightly lower levels of UMIS were detected in assays with variants AF, AB and AA. FIG. 18C shows the median number of genes compared to the median unique molecular identifier (UMI) per cell per engineered reverse transcriptase with 50 k raw reads. Assays performed with the enzyme having the amino acid sequence set forth in SEQ ID NO:1 indicate approximately 4800 UMIs read per cell. Assays performed with AG indicated approximately 4400 UMIs read per cell. Assays performed with AB indicated approximately 5400 UMIs read per cell. Assays performed with AA indicated approximately 5200 UMIs read per cell. Assays performed with AH indicated approximately 3400 UMIs read per cell. Assays performed with AI indicated approximately 4500 UMIs read per cell. UMI's (light bars) and genes (dark bars) are shown. A reduction in complexity is observed with the AG and AF variants.

FIG. 18D summarizes the fraction of ribosomal UMI's (dark bars) and mitochondrial UMI's (light bars) detected in assays with each engineered reverse transcriptase. FIG. 18E depicts results obtained with each indicated engineered reverse transcriptase. The fraction of UMI's for different transcript length ranges (<500, 500-1000, 1000-1500, and >1500 nucleotides) are shown. Dotted lines indicate the fraction of UMI's at each transcript length range for the reverse transcriptase having the amino acid sequence set forth in SEQ ID NO:1. The AB and AA variants show a higher fraction of UMI's in transcripts greater than 1500 nucleotides than with an enzyme having the amino acid sequence set forth in SEQ ID NO:1. The AG variant shows a higher fraction of UMI's in transcripts between 1000-1500 nucleotides in length than with an enzyme having the amino acid sequence set forth in SEQ ID NO:1.

FIG. 18F summarizes the percent of reads confidently mapped to the transcriptome for each of the indicated variants. FIG. 18G summarizes the fraction of usable reads obtained with each indicated variant. The fraction of usable reads obtained from variants AG and AI exceeded the fraction of usable reads obtained from an enzyme having the amino acid sequence set forth in SEQ ID NO:1. Variants AF and AB had similar fractions of usable reads. Variants AA and AH also showed similar fractions of usable reads.

FIGS. 20A, 20B and 20C summarize the median genes and UMI's per cell for each variant at 20,000 raw reads (20 K), 50,000 (50 K) raw reads and 120,000 (120 K) raw reads respectively. At 20K raw reads, an enzyme having the amino acid sequence set forth in SEQ ID NO:1, variants AB and AA yielded approximately 1500 genes per cell; UMI counts were approximately 3800 for an enzyme having the amino acid sequence set forth in SEQ ID NO:1 and AB and approximately 3900 for AA. At 50K raw reads, an enzyme having the amino acid sequence set forth in SEQ ID NO:1, AA and AB yielded approximately 1700, 1900 and 1800 genes per cell; median UMI counts for an enzyme having the amino acid sequence set forth in SEQ ID NO:1, AA and AB were approximately 4500, 5400 and 5000. At 120K raw reads, an enzyme having the amino acid sequence set forth in SEQ ID NO:1, AA and AB yielded approximately 1900, 2200 and 2000 genes per cell; median UMI counts for an enzyme having the amino acid sequence set forth in SEQ ID NO:1, variants AA, and AB were approximately 4500, 5400 and 5000. FIG. 20D summarizes the percent of valid UMIs obtained with an enzyme having the amino acid sequence set forth in SEQ ID NO:1 and variants AB and AA. FIG. 20E indicates the fraction of ribosomal and mitochondrial UMI's obtained with the indicated variant. FIG. 20F summarizes the transcription coverage as a fraction of UMI counts for transcripts less than 500 nucleotides (nt), 500-1000 nt, 1000-1500 nt and more than 1500 nt. FIGS. 20G and 20 H summarizes the fraction of reads confidently mapped to the transcriptome and genome respectively for each indicated variant. FIG. 20I summarizes the fraction of usable reads obtained for each variant in this series. Values vary slightly between experiments and cell population (FIG. 20F vs FIG. 18E).

FIGS. 21A-21C provide a summary of data obtained from a series of assays with an enzyme having the amino acid sequence set forth in SEQ ID NO:1 and variants AB, AY and AC. FIG. 21A summarizes results of a 5' cDNA amplification assay. An enzyme having the amino acid sequence set forth in SEQ ID NO:1 and variant AY show similar results; variant AC resulted in a significantly reduced output in the 500-3000 base pair range; variant AB resulted in a reduced output in the 500-3000 base pair range but greater than that from the AC variant. FIG. 21B summarizes sequencing depth obtained from an enzyme having the amino acid sequence set forth in SEQ ID NO:1 and variants AB, AY and AC. Variants AC and AB exhibited similar sensitivities, at 50,000 and 120,000 reads per cell, both exceeding the sensitivity of an enzyme having the amino acid sequence set forth in SEQ ID NO:1. At 20,000 reads/cell, 50,000 reads/cell and 120,000 reads/cell, variant AY showed decreased median gene per cell and decreased UMI's per cell. FIG. 21C summarizes valid UMI results, ribosomal UMI results, mitochondrial UMI results, transcript coverage and reads mapped to the transcriptome. Variant AC has a much more significant hit to quality control (QC) metrics relative to variant AB and sensitivity is worse at lower depths. Variant AY showed decreased valid UMIs and transcript coverage with slight increases in ribosomal UMIs and mitochondrial UMIs.

FIGS. 23A-23B provide a summary of data obtained from a series of assays with an enzyme having the amino acid sequence set forth in SEQ ID NO:1 and variants AB, AV and AM. FIG. 23A summarizes sequencing depth or median genes per cell as a function of reads per cell. Variants AB and AM exhibit increased median genes per cell and median UMIs per cell at 50,000 reads and 120,000 reads. Variant AV exhibits slightly lower median genes per cell at 20,000 reads; 50,000 reads and 120,000 reads. FIG. 23B summarizes QC metrics in terms of valid UMI results, ribosomal UMI results, mitochondrial UMI results, transcript coverage and reads mapped to the transcriptome for the variants.

FIG. 24A summarizes sequencing depth or median genes per cell as a function of reads per cell. Variant AW shows a moderate improvement to sensitivity at lower read depths than variants having the amino acid sequence set forth in SEQ ID NO:1. FIG. 24B summarizes QC metrics in terms of valid UMI results, ribosomal UMI results, mitochondrial UMI results, transcript coverage and reads mapped to the transcriptome for the variants. Variant AW exhibits QC metrics similar to those exhibited by an enzyme having the amino acid sequence set forth in SEQ ID NO:1 with no significant loss in valid UMIs or mapping.

DETAILED DESCRIPTION

Figure 1:
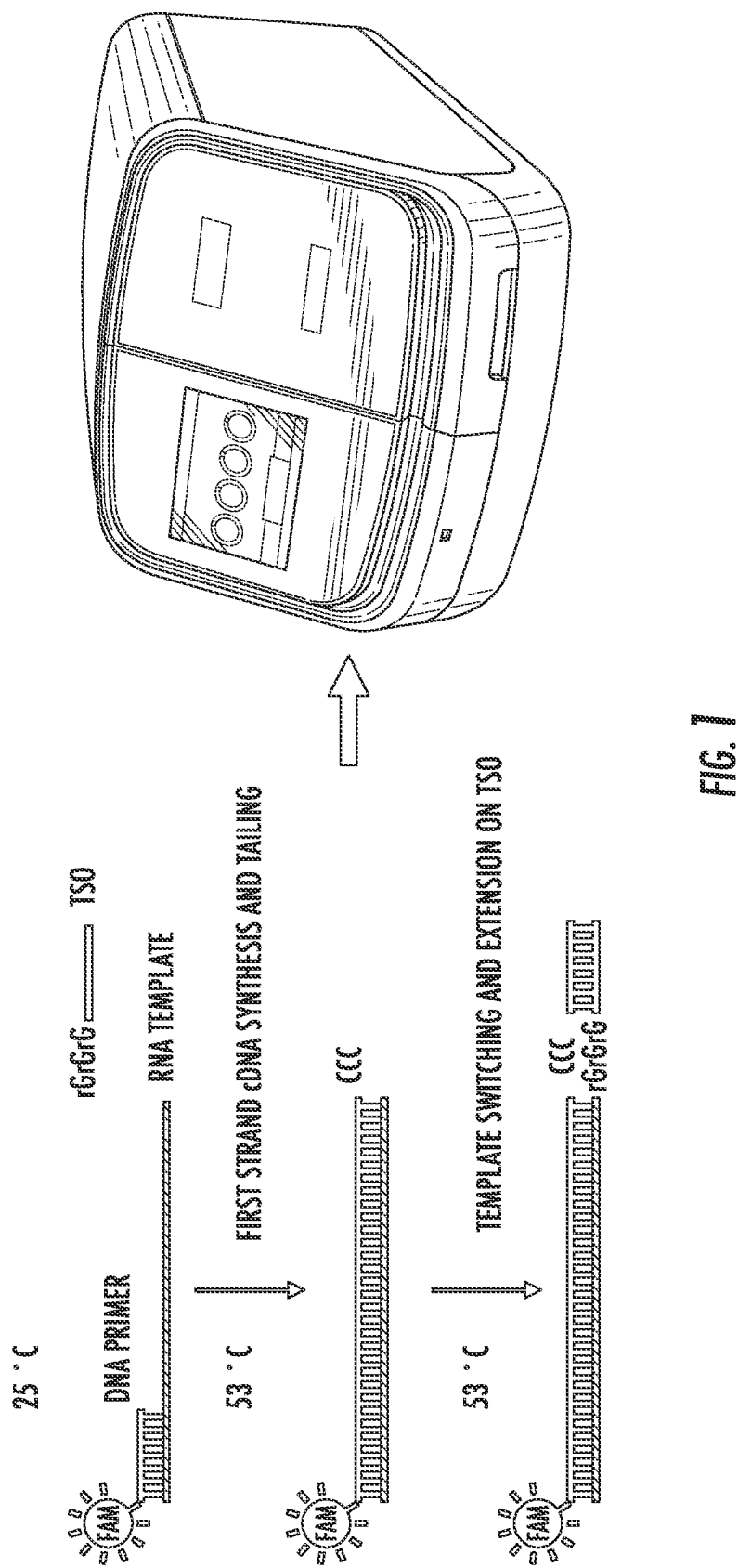
FIG. 1 provides a schematic of the CE validation assay process. 5'-end labeled DNA primers are bound to RNA templates at room temperature (approx. 25° C.). Poly rG-labeled template switching oligos (rG-TSO) are added to the reaction mixture. The temperature is raised to 53° C.; first strand cDNA synthesis, the addition of a poly-C tail (tailing), template switching and TSO extension occur. Samples are transferred to a SeqStudio Genetic Analyzer for analysis.

Reverse transcriptases or reverse transcription enzymes are known in the art; reverse transcriptases perform a reverse transcription reaction. "Reverse transcriptase" and "reverse transcription enzyme" are synonymous. In some embodiments, reverse transcription is initiated by hybridization of a priming sequences to an RNA molecule and is extended by an engineered reverse transcription enzyme in a template directed fashion. In some embodiments, a reverse transcription enzyme adds a plurality of non-template oligonucleotides to a nucleotide strand. In some embodiments, the reverse transcription reaction produces single stranded complementary deoxyribonucleic acid (cDNA) molecules each having a molecular tag from a molecular tags on a 5' end thereof, followed by amplification of cDNA to produce a double stranded cDNA having the molecular tag on the 5' end and a 3' end of the double stranded cDNA. As used herein, the term "wild-type" refers to a gene or gene product that has the characteristics of that gene or gene product when isolated from a naturally occurring source. The amino acid sequence set forth in SEQ ID NO:18 is an MMLV amino acid sequence.

An engineered reverse transcriptase may exhibit one or more reverse transcriptase related activities including but not limited to, RNA-dependent DNA polymerase activity, an RNAse H activity, DNA-dependent DNA polymerase activity, an RNA binding activity, a DNA binding activity, a polymerase activity, a primer extension activity, a strand-displacement activity, a helicase activity, a strand transfer activity, a template binding activity, transcription template switching, ability to yield unique molecular identifiers (UMI), ability to yield median UMI, transcription efficiency, template switching efficiency, processivity, incorporation efficiency, Kd, distribution, fidelity, polymerization efficiency, Km, specificity, non-templated base addition, thermostability, tailing, adapter binding, binding efficiency, binding affinity (Km/Kcat), Vmax and ability to yield median UMI/cell. It is recognized that a change in any activity may increase, decrease or have no effect on a different reverse-transcriptase related activity. It is also recognized that a change in one activity may alter multiple properties of a reverse transcriptase. It is understood that when multiple properties are affected, the properties may be altered similarly or differently. It is further recognized that methods of evaluating reverse transcriptase related activities are known in the art.

In some embodiments, engineered reverse transcription enzymes may further comprise an affinity tag at the N-terminus or at a C-terminus of the amino acid sequence. In some instances, the affinity tag may include, but is not limited to, albumin binding protein (ABP), AU1 epitope, AU5 epitope, T7-tag, V5-tag, B-tag, Chloramphenicol Acetyl Transferase (CAT), Dihydrofolate reductase (DHFR), AviTag, Calmodulin-tag, polyglutamate tag, E-tag, FLAG-tag, HA-tag, Myc-tag, NE-tag, S-tag, SBP-tag, Doftag 1, Softag 3, Spot-tag, tetracysteine (TC) tag, Ty tag, VSV-tag, Xpress tag, biotin carboxyl carrier protein (BCCP), green fluorescent protein tag, HaloTag, Nus-tag, thioredoxin-tag, Fc-tag, cellulose binding domain, chitin binding protein (CBP), choline-binding domain, galactose binding domain, maltose binding protein (MBP), Horseradish Peroxidase (HRP), Strep-tag, HSV epitope, Ketosteroid isomerase (KSI), KT3 epitope, LacZ, Luciferase, PDZ domain, PDZ ligand, Polyarginine (Arg-tag), Polyaspartate (Asp-tag), Polycysteine (Cys-tag), Polyphenylalanine (Phe-tag), Profinity eXact, Protein C, S1-tag, S1-tag, Staphylococcal protein A (Protein A), Staphylococcal protein G (Protein G), Small Ubiquitin-like Modifier (SUMO), Tandem Affinity Purification (TAP), TrpE, Ubiquitin, Universal, glutathione-S-transferase (GST), and poly(His) tag. In some instances, said affinity tag is at least 5 histidine amino acids (SEQ ID NO: 19).

In some embodiments, an engineered reverse transcription enzyme further comprises a protease cleavage sequence, wherein cleavage of the protease cleavage sequence by a protease results in cleavage of the affinity tag from the engineered reverse transcription enzyme. In some instances, protease cleavage sequence is the protease cleavage sequence recognized by a protease including, but not limited to, alanine carboxypeptidase, Armillaria mellea astacin, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, Iga-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB, and Xaa-pro aminopeptidase. In some instances, the protease cleavage sequence is a thrombin cleavage sequence.

Numeric ranges are inclusive of the numbers defining the range. The term about is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

As used herein, "purified" means that a molecule is present in a sample at a concentration of at least 95% by weight, or at least 98% by weight of the sample in which it is contained.

The term "% homology" is used interchangeably herein with the term "% identity" herein and refers to the level of nucleic acid or amino acid sequence identity between the nucleic acid sequence that encodes any one of the inventive polypeptides or the inventive polypeptide's amino acid sequence, when aligned using a sequence alignment program.

"Variant" means a protein which is derived from a precursor protein (such as the native protein, set forth in SEQ ID NO:18) by addition of one or more amino acids to either or both the C- and N-terminal end, substitution of one or more amino acids at one or a number of different sites in the amino acid sequence, or deletion of one or more amino acids at either or both ends of the protein or at one or more sites in the amino acid sequence. SEQ ID NO:1 is a variant of MMLV. The preparation of an enzyme variant is preferably achieved by modifying a DNA sequence which encodes for the wild-type protein, transformation of that DNA sequence into a suitable host, and expression of the modified DNA sequence to form the derivative enzyme. It is recognized that the preparation of an enzyme variant may be achieved by modifying a DNA sequence which encodes for a variant of a wild-type protein, transformation of that DNA sequence into a suitable host, and expression of the modified DNA sequence to form the derivative enzyme. A variant reverse transcriptase of the invention includes peptides comprising altered amino acid sequences in comparison with a precursor enzyme amino acid sequence wherein the variant reverse transcriptase retains the characteristic enzymatic nature of the precursor enzyme but which may have altered properties in some specific aspect. For example, an engineered reverse transcriptase variant may have an altered pH optimum or increased temperature stability but may retain its characteristic transcriptase activity. A "variant" may have at least about 45%, at least about 50%, at least about 55%, at least about 60%, at least about 65%, at least about 70%, at least about 75%, at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, or at least about 99.5% sequence identity to a polypeptide sequence when optimally aligned for comparison. As used herein variant residue position is described in relation to the wild-type or precursor amino acid sequence set forth in SEQ ID NO:18; the amino acid position is indexed to SEQ ID NO:18.

As used herein, a polypeptide having a certain percent (e.g., at least 90%, at least 91%, at least 92%, at least 93%, at least 94%, at least 95%, at least 96%, at least 97%, at least 98%, or at least 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY, Ausubel et al., eds., 1987, Supplement 30, section 7.7.18. Representative programs include the Vector NTI Advance™ 9.0 (Invitrogen Corp. Carlsbad, Calif.), GCG Pileup, FASTA (Pearson et al. (1988) Proc. Natl Acad. ScL USA 85:2444-2448), and BLAST (BLAST Manual, Altschul et al., Nat'l Cent. Biotechnol. Inf., Nat'l Lib. Med. (NCIB NLM NIH), Bethesda, Md., and Altschul et al., (1997) Nucleic Acids Res. 25:3389-3402) programs. Another typical alignment program is ALIGN Plus (Scientific and Educational Software, PA), generally using default parameters. Other sequence software programs that find use are the TFASTA Data Searching Program available in the Sequence Software Package Version 6.0 (Genetics Computer Group, University of Wisconsin, Madison, Wis. and CLC Main Workbench (Qiagen) Version 20.0.

In some embodiments, the engineered reverse transcription enzyme comprises an amino acid sequence that is at least 95% identical to a reverse transcriptase having the amino acid sequence set forth in SEQ ID NO:1. In some embodiments, the engineered reverse transcription enzyme comprises an amino acid sequence that is at least 95% identical to SEQ ID NO: 1 and has at least one mutation selected from the group comprising, consisting or consisting essentially of a M39 mutation; a M66 mutation, a K69 mutation, a W94 mutation, a P139 mutation, a N200 mutation, an E201 mutation, a T287 mutation, an R301 mutation, an R302 mutation, a K306 mutation, a F309 mutation, a P330 mutation, a C409 mutation, an R411 mutation, an L435 mutation, an A448 mutation, a G449 mutation, a K454 mutation, an A502 mutation, an H503 mutation, a N524 mutation, a D524 mutation, an H594 mutation, a W603 mutation, a K607 mutation, an H634 mutation, a P636 mutation, and a G637 mutation; and the engineered reverse transcription enzyme exhibits an altered reverse transcriptase related activity.

In some embodiments, the engineered reverse transcription enzyme comprises an amino acid sequence that is at least 95% identical to SEQ ID NO: 1 and has at least one mutation selected from the group comprising, consisting or consisting essentially of a M39 mutation; a M66 mutation, an E201 mutation, a T287 mutation, a C409 mutation, an H503 mutation, an H594 mutation, an H634 mutation, and a G637 mutation and wherein said engineered reverse transcription enzyme exhibits an altered reverse transcriptase related activity. In various embodiment an engineered reverse transcriptase has at least two, at least three, at least four, at least five, at least six, at least seven or at least eight mutations from the group comprising, consisting or consisting essentially of a M39 mutation; a M66 mutation, an E201 mutation, a T287 mutation, a C409 mutation, an H503 mutation, an H594 mutation, an H634 mutation, and a G637 mutation. In some embodiments, the engineered reverse transcriptase has at least one mutation is selected from the group comprising a M39 mutation; a M66 mutation, an E201 mutation, a T287 mutation, a C409 mutation, an H503 mutation, an H594 mutation, an H634 mutation, and a G637 mutation. In some embodiments an engineered reverse transcriptase of the present application has an amino acid sequence encoded by a nucleotide sequence set forth in the group comprising SEQ ID NO:2, SEQ ID NO:3, SEQ ID NO:4, SEQ ID NO:5, SEQ ID NO:6, SEQ ID NO: 7, SEQ ID NO: 8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17.

In some embodiments, engineered reverse transcription enzyme comprises an amino acid sequence that is at least 95% identical to SEQ ID NO: 1 and has at least one mutation selected from the group comprising, consisting or consisting essentially of an A32 mutation, a M39 mutation; a P51 mutation, a M66 mutation, an S67 mutation, a K69 mutation, an L72 mutation, a W94 mutation, a K103 mutation, an R110 mutation, a P139 mutation, an F155 mutation, a T197 mutation, an N200 mutation, an E201 mutation, an H204 mutation, a Q221 mutation, a V223 mutation, a V238 mutation, a G248 mutation, an E286 mutation, a T287 mutation, an R301 mutation, an R302 mutation, a K306 mutation, a F309 mutation, an F323 mutation, a P330 mutation, a Y344 mutation, an 1347 mutation, a W388 mutation, a C409 mutation, an R411 mutation, an L435- mutation, an A448 mutation, a G449 mutation, a D450 mutation, a K454 mutation, an A502 mutation, an H503 mutation, a N524 mutation, a D524 mutation, a D583 mutation, an H594 mutation, a W603 mutation, a K607 mutation, an H634 mutation, a D653 mutation, a P636 mutation, a G637 mutation, an H638 mutation, and an L671 mutation; and the engineered reverse transcription enzyme exhibits an altered reverse transcriptase related activity.

In some embodiments, an engineered reverse transcriptase comprising an amino acid sequence that is at least 95% identical to SEQ ID NO:1, wherein the engineered reverse transcriptase exhibits an altered reverse transcriptase related activity as compared to a reverse transcriptase having the amino acid sequence set forth in SEQ ID NO:1, and wherein the engineered reverse transcriptase comprises a combination of mutations indexed to SEQ ID NO:18 selected from the group consisting of i) an E69K mutation, an E302R mutation, a T306K mutation, a W313F mutation, an L435G mutation, and an N454K mutation, and further comprising at least one mutation selected from the group consisting of an M39V mutation, an M66L mutation, an L139P mutation, an F155Y mutation, a D200N mutation, an E201Q mutation, a T287A mutation, a T330P mutation, an R411F mutation, a P448A mutation, a D449G mutation, an H503V mutation, an H594K mutation, L603W mutation, an E607K mutation, an H634Y mutation, a G637R mutation and an H638G mutation; ii) an L139P mutation, a D200N mutation, a T330P mutation, an L603W mutation, and an E607K mutation, and further comprising at least one mutation selected from the group consisting of: an M39V mutation, an M66L mutation an E69K mutation, an F155Y mutation, an E201Q mutation, a T287A mutation, an E302R mutation, a T306K mutation, a W313F mutation, an R411F mutation, an L435G mutation, a P448A mutation, a D449G mutation, an N454K mutation, an H503V mutation, an H594K mutation, an H634Y mutation, a G637R mutation and an H638G mutation; iii) an A32V mutation, an L72R mutation, a D200C mutation, a G248C mutation, an E286R mutation, an E302R mutation, a W388R mutation, and an L435G mutation; and iv) a Y344L mutation and an I347L mutation. A variant may comprise a combination of mutations or alterations and may further comprise a second combination of mutations.

In some embodiments, the engineered reverse transcription enzyme is engineered to have reduced and/or abolished RNase activity. In some embodiments, the engineered reverse transcription enzyme is engineered to have reduced and/or abolished RNase H activity. In some embodiments, the engineered reverse transcription enzyme engineered to have reduced and/or abolished RNase H activity comprises a mutation analogous to a MMLV reverse transcriptase D524 mutation.

The engineered reverse transcription enzyme variants of the present disclosure unexpectedly provided an altered reverse transcriptase activity, such as but not limited to, improved thermal stability, processive reverse transcription, non-templated base addition, and template switching ability. An engineered reverse transcription enzyme of the current application may exhibit an altered base-biased template switching activity such as an increased base-biased template switching activity, decreased base-biased template switching activity or an altered base-bias to the template switching activity. An engineered reverse transcriptase variant may exhibit enhanced template switching with a 5'-G cap on the substrate. Furthermore, an engineered reverse transcription enzyme variants described herein may also exhibit unexpectedly higher resistance to cell lysate (i.e., are less inhibited by cell lysate) than that exhibited by an enzyme having the amino acid sequence set forth in SEQ ID NO:1. Lastly, an engineered reverse transcription enzyme variants of the present disclosure may have an unexpectedly greater ability to capture full-length transcripts (e.g., in T-cell receptor paired transcriptional profiling), as compared to that exhibited by an enzyme having the amino acid sequence set forth in SEQ ID NO:1.

It is recognized that mutation of one or more residues may alter a first reverse transcriptase activity differently than a second reverse transcriptase activity. Further it is recognized that a different combination of mutations, such as different sites or residue changes may alter a reverse transcriptase activity similarly or differently. The variants that can template switch in the 5' assay share the following alterations: E69K, E302R, T306K, W313F, L/K435G, and N454K. These variants may further comprise additional alterations that may affect one or more reverse transcriptase related activities. The current work indicates M39V and M66L improve template switching. The AF variant comprises M39V and M66L and other mutations. AF does not show increased product yield in the 5'-GEM assay; without being limited by mechanism, mutations present in AF may alter $k_d$ and/or processivity. Without being limited by mechanism variants comprising a M39V or a M66L mutation that do not exhibit altered performance in the 5' GEM assay may exhibit an altered processivity, an altered $k_d$ or both.

Some variants share the following alterations: an L139P mutation, a D200N mutation, a T330P mutation, an L603W mutation, and an E607K mutation. These variants may further comprise additional alterations that may affect one or more reverse transcriptase related activities.

The engineered reverse transcriptases of the present application may be used in any application in which a reverse transcriptase with the indicated altered activity is desired. Methods of using reverse transcriptases are known in the art; one skilled in the art may select any of the engineered reverse transcriptases disclosed herein. In some embodiments, a reverse transcription reaction introduces a bar code. In some embodiments, the barcoding reaction is an enzymatic reaction. In some embodiments, the barcoding reaction is a reverse transcription amplification reaction that generates complementary deoxyribonucleic acid (cDNA) molecules upon reverse transcription of ribonucleic acid (RNA) molecules of the cell. In some embodiments, the RNA molecules are released from the cell. In some embodiments, the RNA molecules are released from the cell by lysing the cell. In some embodiments, the RNA molecules are messenger RNA (mRNA).

In some embodiments, the molecular tags are coupled to priming sequences and the barcoding reaction is initiated by hybridization of the priming sequences to the RNA molecules. In some embodiments, each priming sequence comprises a random N-mer sequence. In some embodiments, the random N-mer sequence is complementary to a 3' sequence of a ribonucleic acid molecule of said cell. In some embodiments, the random N-mer sequence comprises a poly-dT sequence having a length of at least 5 bases. In some embodiments, the random N-mer sequence comprises a poly-dT sequence having a length of at least 10 bases (SEQ ID NO:23). In some embodiments, the barcoding reaction is performed by extending the priming sequences in a template directed fashion using reagents for reverse transcription. In some embodiments, the reagents for reverse transcription comprise a reverse transcription enzyme, a buffer and a mixture of nucleotides. In some embodiments, the reverse transcription enzyme adds a plurality of non-template oligonucleotides upon reverse transcription of a ribonucleic acid molecule from the nucleic acid molecules. In some embodiments, the reverse transcription enzyme is an engineered reverse transcription enzyme as disclosed herein.

In some embodiments, the barcoding reaction produces single stranded complementary deoxyribonucleic acid (cDNA) molecules each having a molecular tag from said molecular tags on a 5' end thereof, followed by amplification of cDNA to produce a double stranded cDNA having the molecular tag on the 5' end and a 3' end of the double stranded cDNA.

In some embodiments, the molecular tags (e.g., barcode oligonucleotides) include unique molecular identifiers (UMIs). In some embodiments, the UMIs comprise oligonucleotides. In some embodiments, the molecular tags are coupled to priming sequences. In some embodiments, each of said priming sequences comprises a random N-mer sequence. In some embodiments, the random N-mer sequence is complementary to a 3' sequence of said RNA molecules. In some embodiments, the priming sequence comprises a poly-dT sequence having a length of at least 5 bases. In some embodiments, the priming sequence comprises a poly-dT sequence having a length of at least 10 bases (SEQ ID NO:23). In some embodiments, the priming sequence comprises a poly-dT sequence having a length of at least 5 bases, at least 6 bases, at least 7 bases, at least 8 bases, at least 9 bases, at least 10 bases (SEQ ID NO:23.

Unique molecular identifiers (UMIs), e.g., in the form of nucleic acid barcodes are assigned or associated with individual cells or populations of cells, in order to tag or label the cell's components (and as a result, its characteristics) with the unique identifiers. These unique molecular identifiers may be used to attribute the cell's components and characteristics to an individual cell or group of cells.

In some aspects, the unique molecular identifiers are provided in the form of nucleic acid molecules (e.g., oligonucleotides) that comprise nucleic acid barcode sequences that may be attached to or otherwise associated with the nucleic acid contents of individual cell, or to other components of the cell, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

Moreover, when a population of barcodes is partitioned, the resulting population of partitions can also include a diverse barcode library that may include at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

The engineered reverse transcriptases of the present application may be suitable for use in methods in which a cell can be co-partitioned along with a barcode bearing bead. The barcoded nucleic acid molecules can be released from the bead in the partition. By way of example, in the context of analyzing sample RNA, the poly-dT (poly-deoxythymine, also referred to as oligo (dT)) segment of one of the released nucleic acid molecules can hybridize to the poly-A tail of a mRNA molecule. Reverse transcription may result in a cDNA transcript of the mRNA, but which transcript includes each of the sequence segments of the nucleic acid molecule. Without being limited by mechanism, because the nucleic acid molecule comprises an anchoring sequence, it may be more likely hybridize to and prime reverse transcription at the sequence end of the poly-A tail of the mRNA. Within any given partition, all of the cDNA transcripts of the individual mRNA molecules may include a common barcode sequence segment. However, the transcripts made from the different mRNA molecules within a given partition may vary at the unique molecular identifying sequence segment (e.g., UMI segment). Beneficially, even following any subsequent amplification of the contents of a given partition, the number of different UMIs can be indicative of the quantity of mRNA originating from a given partition, and thus from the cell. As noted above, the transcripts can be amplified, cleaned up and sequenced to identify the sequence of the cDNA transcript of the mRNA, as well as to sequence the barcode segment and the UMI segment. While a poly-dT primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

Template switching oligonucleotides (also referred to herein as "switch oligos" or "switch oligonucleotides") may be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination. Suitable lengths of a switch oligo are known in the art. See for example U.S. patent application Ser. No. 15/975,516, filed May 9, 2018, herein incorporated by reference in its entirety.

In various embodiments the poly-dT segment may be extended in a reverse transcription reaction using the mRNA as a template to produce a cDNA transcript complementary to the mRNA and also includes sequence segments of a barcode oligonucleotide. Terminal transferase activity of the reverse transcriptase can add additional bases to the cDNA transcript (e.g., polyC). The switch oligo may then hybridize with the additional bases added to the cDNA transcript and facilitate template switching. A sequence complementary to the switch oligo sequence can then be incorporated into the cDNA transcript via extension of the cDNA transcript using the switch oligo as a template. Within any given partition, all the cDNA transcripts of the individual mRNA molecules include a common barcode sequence segment. However, by including the unique random N-mer sequence, the transcripts made from different mRNA molecules within a given partition will vary at this unique sequence. As described elsewhere herein, this provides a quantification feature that can be identifiable even following any subsequent amplification of the contents of a given partition, e.g., the number of unique segments associated with a common barcode can be indicative of the quantity of mRNA originating from a single partition, and thus, a single cell. The cDNA transcript may then be amplified with PCR primers. Next, the amplified product may then be purified (e.g., via solid phase reversible immobilization (SPRI)). The amplified product is then sheared, ligated to additional functional sequences, and further amplified (e.g., via PCR). The functional sequences may include a sequencer specific flow cell attachment sequence such as but not limited to, a P7 sequence for Illumina sequencing systems, as well as functional sequence, which may include a sequencing primer binding site, e.g., for a R2 primer for Illumina sequencing systems, as well as functional sequence, which may include a sample index, e.g., an i7 sample index sequence for Illumina sequencing systems. Although described in terms of specific sequence references used for certain sequencing systems, e.g., Illumina systems, it will be understood that the reference to these sequences is for illustration purposes only, and the methods described herein may be configured for use with other sequencing systems incorporating specific priming, attachment, index, and other operational sequences used in those systems, e.g., systems available from Ion Torrent, Oxford Nanopore, Genia, Pacific Biosciences, Complete Genomics, and the like.

It is recognized that certain reverse transcriptase enzymes may increase UMI reads from genes of a desired length or length of interest. The desired length of genes may be selected from the group of lengths comprising or consisting of less than 500 nucleotides, between 500 and 1000 nucleotides, between 1000 and 1500 nucleotides and greater than 1500 nucleotides. It is recognized that a reverse transcriptase may preferentially increase UMI reads from genes of one length range. It is recognized that an engineered reverse transcriptase may perform similarly, differently or comparably in a 3'-reverse transcription assay or a 5'-reverse transcription assay. It is similarly recognized that an engineered reverse transcriptase may preferentially increase UMI reads from a length of genes in a 3'-reverse transcription assay than in a 5'-reverse transcription assay.

By "low volume reaction" is intended a reaction volume less than 1 nanoliter, less than 750 picoliters, or less than 500 picoliters.

Figure 4:
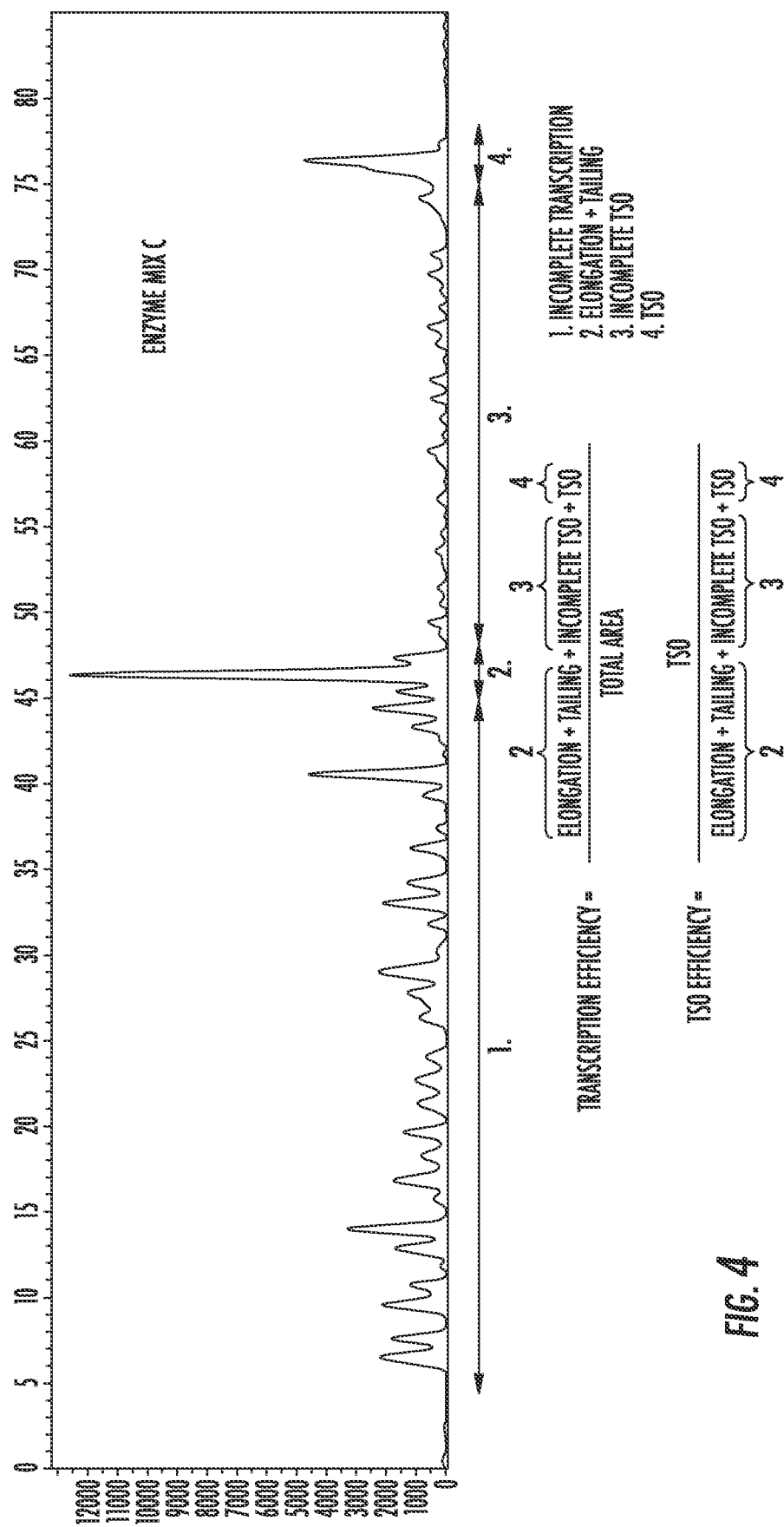
FIG. 4 provides a trace of CE assay output for enzyme mix C and the length parameters associated with various reaction products as used for transcription efficiency and template switching efficiency calculations. Reads less than 45 nucleotides are considered incomplete (section 1). Reads including the full length and the full length plus the tail are considered the elongation and tailing phase (section 2). Reads longer than the full length plus the tail and shorter than the full length plus tail and template switching are considered incomplete template switching products (incomplete TSO, section 3). Reads having the full length plus tail and template switching size are considered template switched (TSO, section 4). Transcription efficiency is the sum of the area under the curve for section 2, section 3 and section 4 divided by the total area under the curve. Template switching efficiency is the area under the curve of the template switched (section 4) divided by the sum of the area under curve for section 2, section 3 and section 4.

Transcription efficiency may be calculated as the sum of the area under the curve for the elongation, elongation plus tail, incomplete template switching (TSO) and complete template switching (TSO) regions over the total area under the curve for all products. Transcription efficiency reflects all those products for which transcription was successfully completed. Template switching oligonucleotide efficiency may be calculated as the area under the curve for the complete template switching region (4) over the total area under the curve for all full-length products. See FIG. 4 for an example and designations of chromatograph regions or areas under the curve. An engineered reverse transcriptase may have an increased transcription efficiency, an increased TSO efficiency or both an increased transcription efficiency and an increased TSO efficiency.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion) Torrent®. Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

In one aspect, the present invention provides methods that utilize the engineered reverse transcriptases described herein for nucleic acid sample processing. In one embodiment, the method comprises contacting a template ribonucleic acid (RNA) molecule with an engineered reverse transcriptase to reverse transcribe the RNA molecule to a complementary DNA (cDNA) molecule. The contacting step may be in the presence of a plurality of nucleic acid barcode molecules, wherein each nucleic acid barcode molecule comprises a barcode sequence. The nucleic acid barcode molecule may further comprise a sequence configured to couple to a template RNA molecule. Suitable sequences include, without limitation, an oligo(dT) sequence, a random N-mer primer, or a target-specific primer. The nucleic acid barcode molecule may further comprise a template switching sequence. In other embodiments, the RNA molecule is a messenger RNA (mRNA) molecule. In one embodiment, contacting step provides conditions suitable to allow the engineered reverse transcriptase to (i) transcribe the mRNA molecule into the cDNA molecule with the oligo(dT) sequence and/or (ii) perform a template switching reaction, thereby generating the cDNA molecule which comprises the barcode sequence, or a derivative thereof. In another embodiment, the contacting step may occur in (i) a partition having a reaction volume (as further described herein and see e.g., U.S. Pat. Nos. 10,400,280 and 10,323,278, each of which is incorporated herein by reference in its entirety), (ii) in a bulk reaction where the reaction components (e.g., template RNA and engineered reverse transcriptase) are in solution, or (iii) on a nucleic acid array (see e.g., U.S. Pat. Nos. 10,480,022 and 10,030,261 as well as WO/2020/047005 and WO/2020/047010, each of which is incorporated herein by reference in its entirety).

In another embodiment, the method comprises providing a reaction volume which comprises an engineered reverse transcriptase and a template ribonucleic acid (RNA) molecule. The reaction volume may further comprise a plurality of nucleic acid barcode molecules, wherein each nucleic acid barcode molecule comprises a barcode sequence. In one other embodiment, the contacting occurs in a reaction volume, which may be less than 1 nanoliter, less than 750 picoliters, or less than 500 picoliters. In other embodiments, the reaction volume is present in a partition, such as a droplet or well (including a microwell or a nanowell).

It will be understood that the reference to the below examples is for illustration purposes only and do not limit the scope of the claims.

EXAMPLES

Example 1 CE Assay Validation

Figure 2:
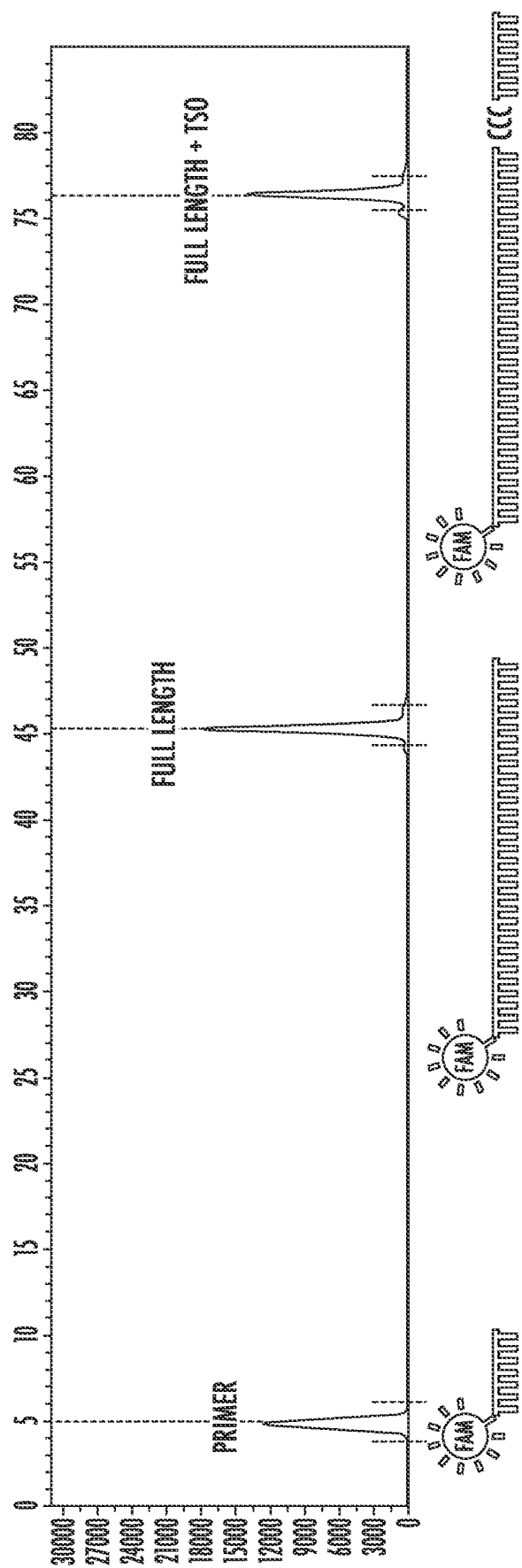
FIG. 2 provides a trace of the CE assay output. Product size was calibrated with synthetically sized controls for the primer alone size, a full-length extension of the primer length, and a full-length extension of the primer plus template switching oligo. Product length is indicated on the x-axis.
Figure 3:
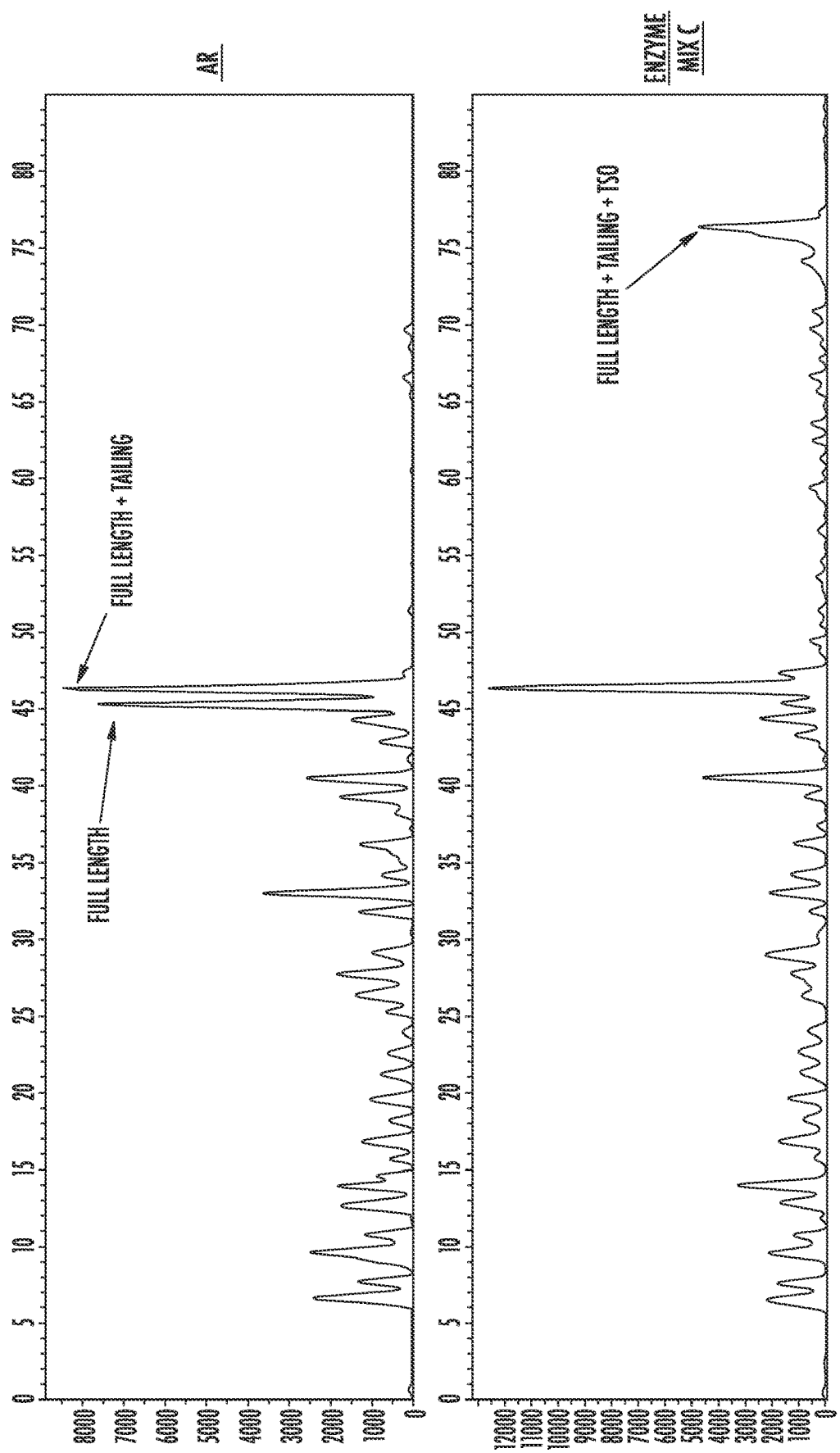
FIG. 3 provides a trace of CE assay output for enzyme controls for enzyme mix C (containing a commercially prepared engineered reverse transcriptase) and an engineered reverse transcriptase AR. Product length is indicated on the x-axis; signal intensity is indicated on the y-axis. Peaks associated with the full-length product, the full length product plus tail and the full length product plus tail and template switching are indicated. The trace indicates reactions with enzyme mix C (EMC, a commercially available reverse transcriptase) yield full sized template switched product. The trace indicates reactions with enzyme AR yield full length transcription products; a full-size template switched product peak is not significantly present.

Reverse transcription and sequencing reactions were prepared. The reaction volume was 50 µl; reactions contained 5'-end labeled FAM Reverse Transcriptase primer 2, GEM-U reagent, RNA template (RNA Temp 2CE), template switching oligo 1 (TSO1), and the indicated engineered reverse transcriptase. Stock concentrations and final concentrations in the reactions are shown in Table 1. The reactions included stoichiometrically equal amounts of enzyme and template for single turnover conditions. Reactants were incubated at 53° C. for one hour, then diluted 1:40 in water and then 1:20 in HiDi formamide. The formamide mixture was heated to 95° C. for 5 mins, then chilled on ice for 2 mins. Samples were loaded on the CE, the DS-33 dye set was selected and fragment analysis (SnapShot) was performed using the GS120LIZ size standard. The assay was validated with synthetically sized oligonucleotides (FIG. 2) and with a transcription positive, template switching null engineered reverse transcriptase AR and a transcription positive, template switching positive commercially prepared reverse transcriptase (Enzyme Mix C) (FIG. 3). The GEM-U reagent approximates the formulation of the actual reagent mixture in a GEM assay when the contents of the $Z_1$ and $Z_2$ channels are mixed.

TABLE 1

Capillary Electrophoresis (CE) Assay Reactants and Template, Primer and TSO sequences (SEQ ID NOS: 20-22, respectively in order of appearance.)

| Reagent | Stock | Final |
| --- | --- | --- |
| GEM-U Reagent | 2.66 x | 1.00 x |
| FAM.RT.Primer2 | 100.00 uM | 0.50 uM |
| RNA.Temp2.CE | 84.40 uM | 0.50 uM |

TABLE 1-continued

Capillary Electrophoresis (CE) Assay Reactants and Template, Primer and TSO sequences (SEQ ID NOS: 20-22, respectively in order of appearance.)

| | | |
| --- | --- | --- |
| TSO1.Oligo | 91.20 uM | 5.00 uM |
| Enzyme | 15.40 uM | 0.50 uM |
| Water | — | — |
| Template | RNA.Temp2.CE | rArCrG rArCrC rGrUrC rGrUrC rArUrG rUrArG rCrGru rUrUrG rUrCrG rGrArG rArCrU rCrCrU rArGrA rUrCrA rGrArU rGrUrC rCrUrC rCrUrG rGrCrU rArCrU rGrCrA |
| Primer | FAM.RT.Primer2 | /56-FAM/CGA CTC ACT GAC ACT CGC |
| TSO | TSO1.Oligo | AAG CAG TGG TAT CAA CGC AGA GTA CAT rGrGrG |

Example 2. Construction of Engineered Reverse Transcriptases

Some mutants were constructed using a Q5 mutagenesis kit (NEB) with mutagenic primers. Linearized products were then circularized by KLD treatment (kinase, ligase, DpN1) and cloned. Some mutants were synthesized as whole plasmids (Twist).

Figure 5:
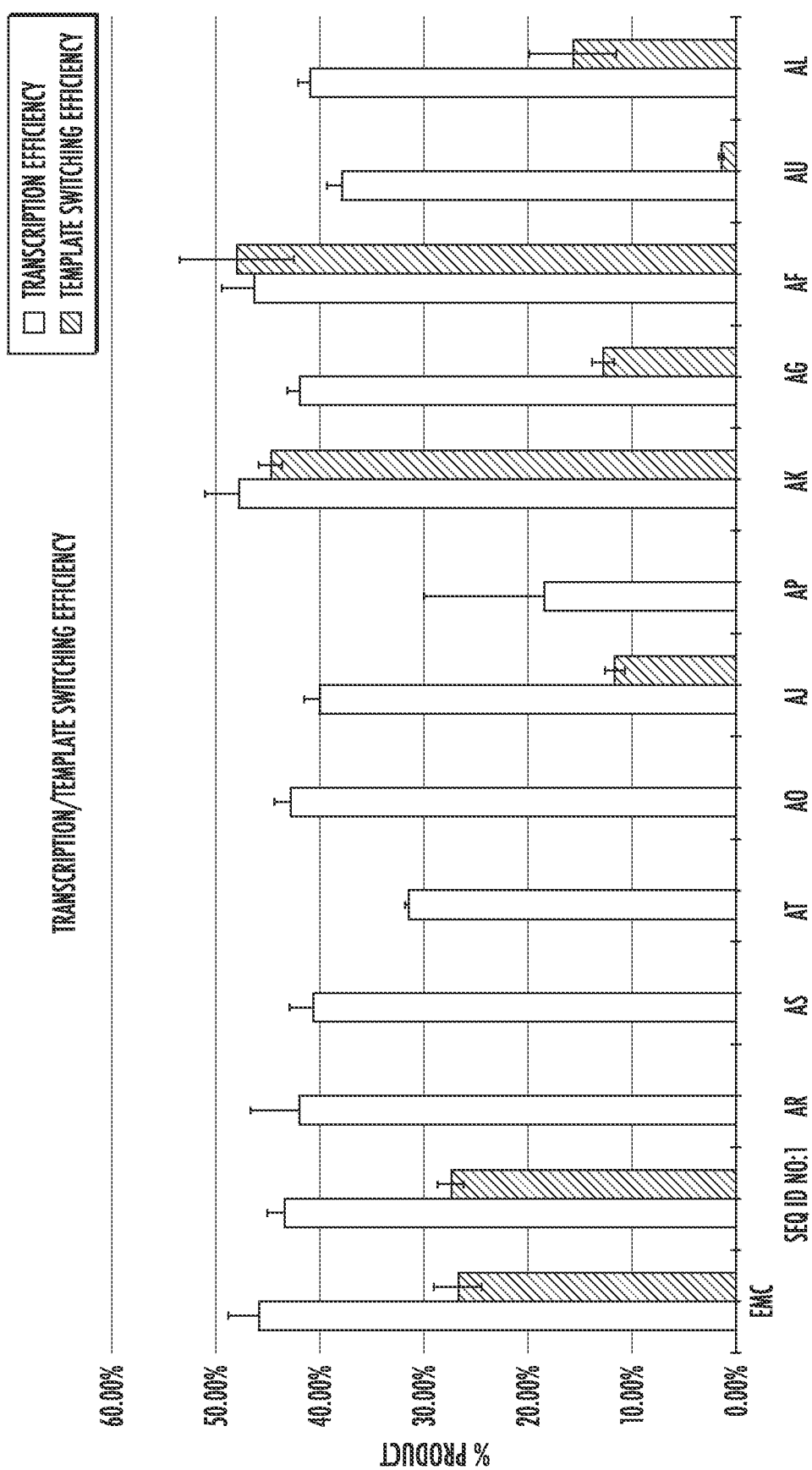
FIG. 5 provides a chart comparing the transcription efficiency and template switching efficiency of multiple engineered reverse transcriptases. Bars indicating the transcription efficiency are indicated on the left for each enzyme tested; bars indicating the template switching efficiency are indicated on the right for each enzyme tested. The percent product is indicated on the y axis; the enzyme tested is indicated on the x axis. EMC refers to enzyme master mix C, and SEQ ID NO:1 refers to an engineered reverse transcriptase having the amino acid sequence set forth in SEQ ID NO:1. Results from the indicated engineered reverse transcriptase are provided. SEQ ID NO:1 and variants AR, AS, AO, AJ, AK, AG, AF, and AL exhibit transcription efficiencies at or above about 40%. Variants AT, AP and AU exhibit transcription efficiencies below 40%. EMC and SEQ ID NO:1 exhibit template switching efficiencies below 30%. Variants AK and AF exhibit template switching efficiencies above 40%. Variants AJ, AG and AL exhibit template switching efficiencies above 10%; variant AU exhibits template switching efficiency below 10%.

Example 3. Transcription Efficiency and Template Switching Efficiency Analysis CE reactions were performed as described above herein using a variety of reverse transcriptases and engineered reverse transcriptases. The transcription efficiency and template switching efficiency as a percent product were determined. Results from one such series of experiments are shown in FIG. 5.

Example 4. Mean Read/Cell Assessment

Figure 6:
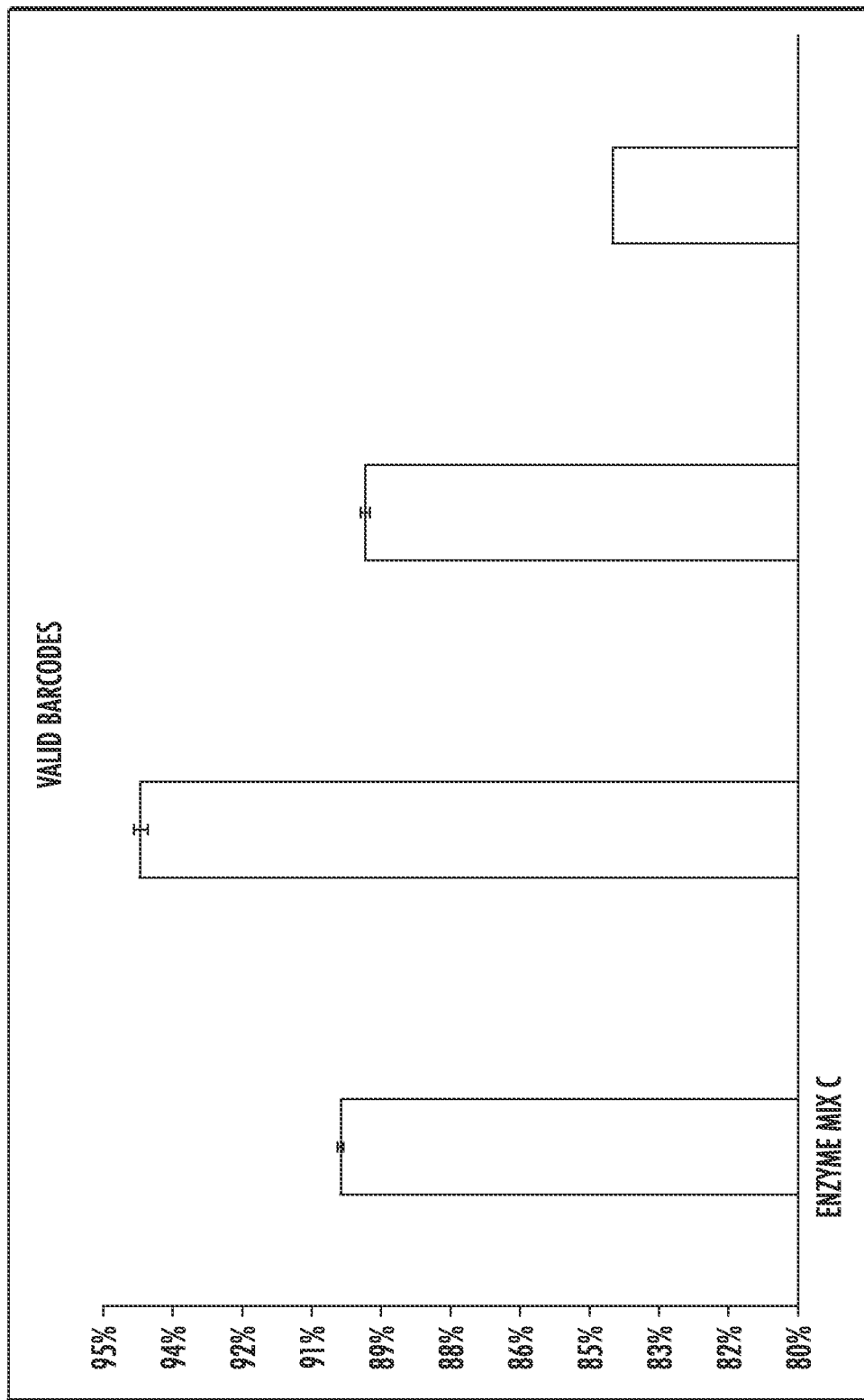
FIG. 6 provides a chart summarizing the percent of valid barcodes in reads obtained when the indicated engineered reverse transcriptases (Enzyme Mix C, SEQ ID NO:1, variant AO and variant AK) were used in a GEM-X assay.
Figure 7:
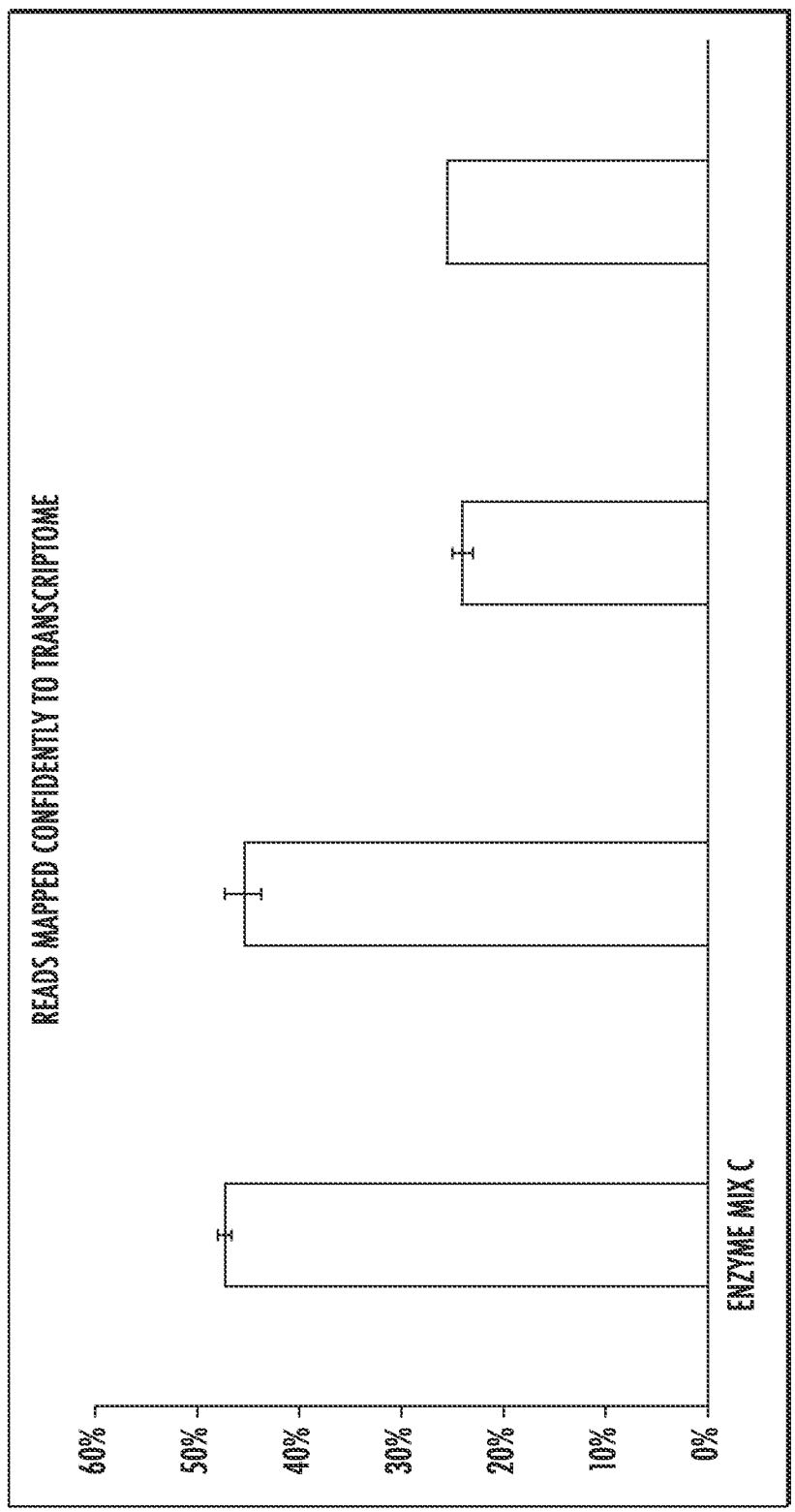
FIG. 7 provides a chart summarizing the percent of reads confidently mapped to the transcriptome when the indicated engineered reverse transcriptases (Enzyme Mix C, SEQ ID NO:1, variant AO and variant AK) were used in a GEM-X assay.
Figure 8:
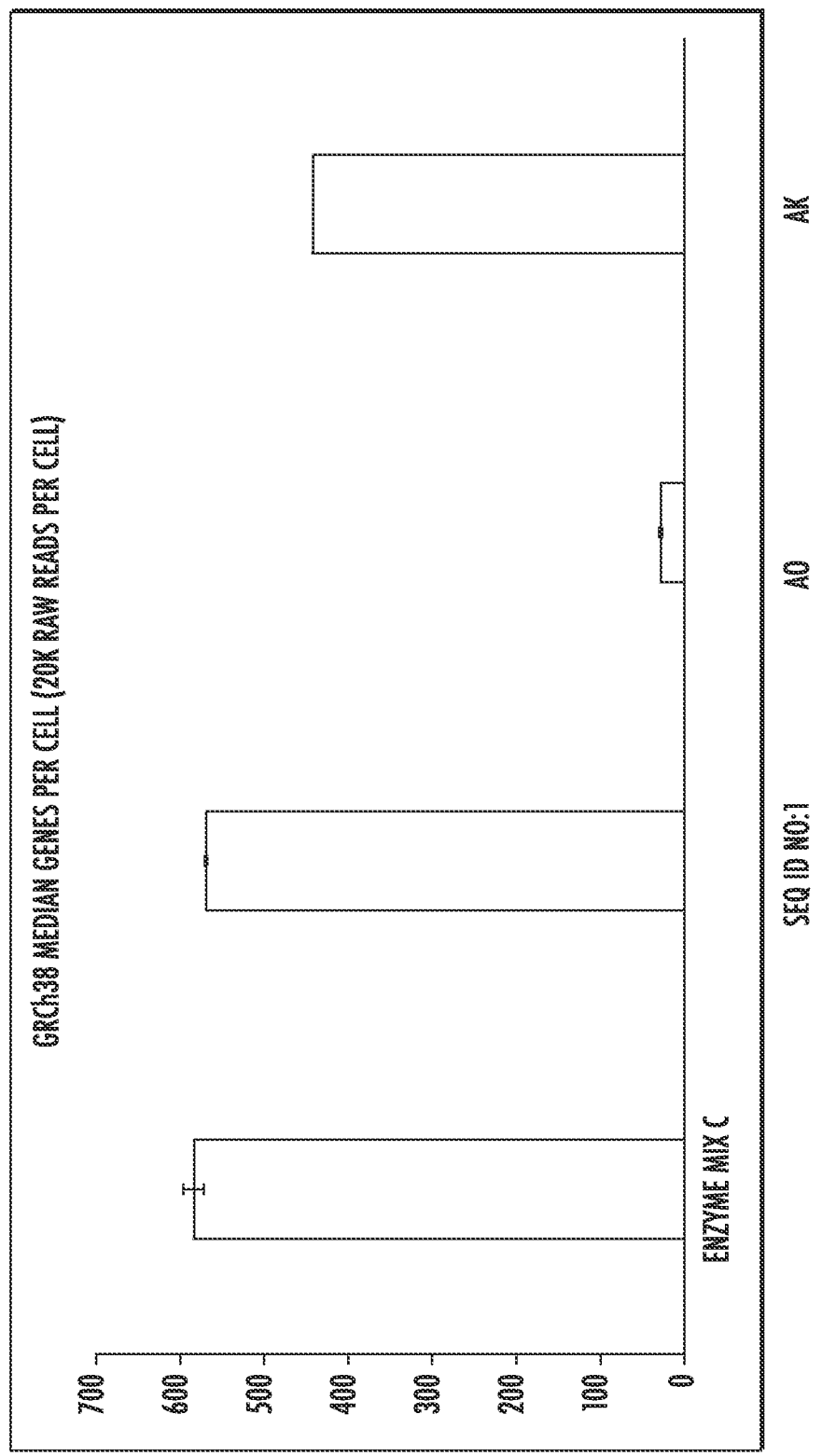
FIG. 8 provides a chart summarizing the median genes identified per cell when the indicated engineered reverse transcriptases (Enzyme Mix C, SEQ ID NO:1, variant AO and variant AK) were used in a GEM-X assay.
Figure 9:
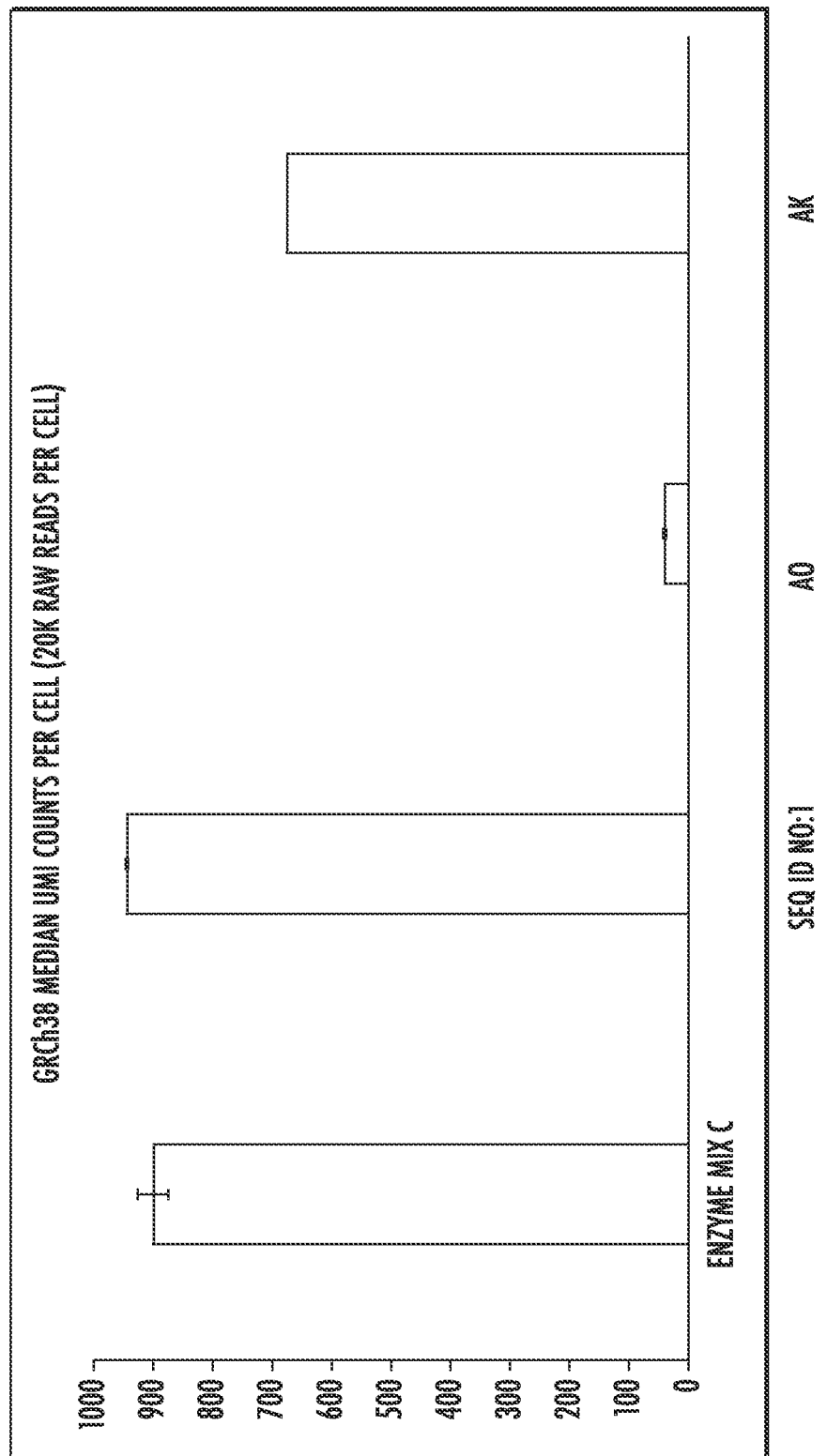
FIG. 9 provides a chart summarizing the median UMI counts per cell when the indicated engineered reverse transcriptases (Enzyme Mix C, SEQ ID NO:1, variant AO and variant AK) were used in a GEM-X assay.
Figure 10:
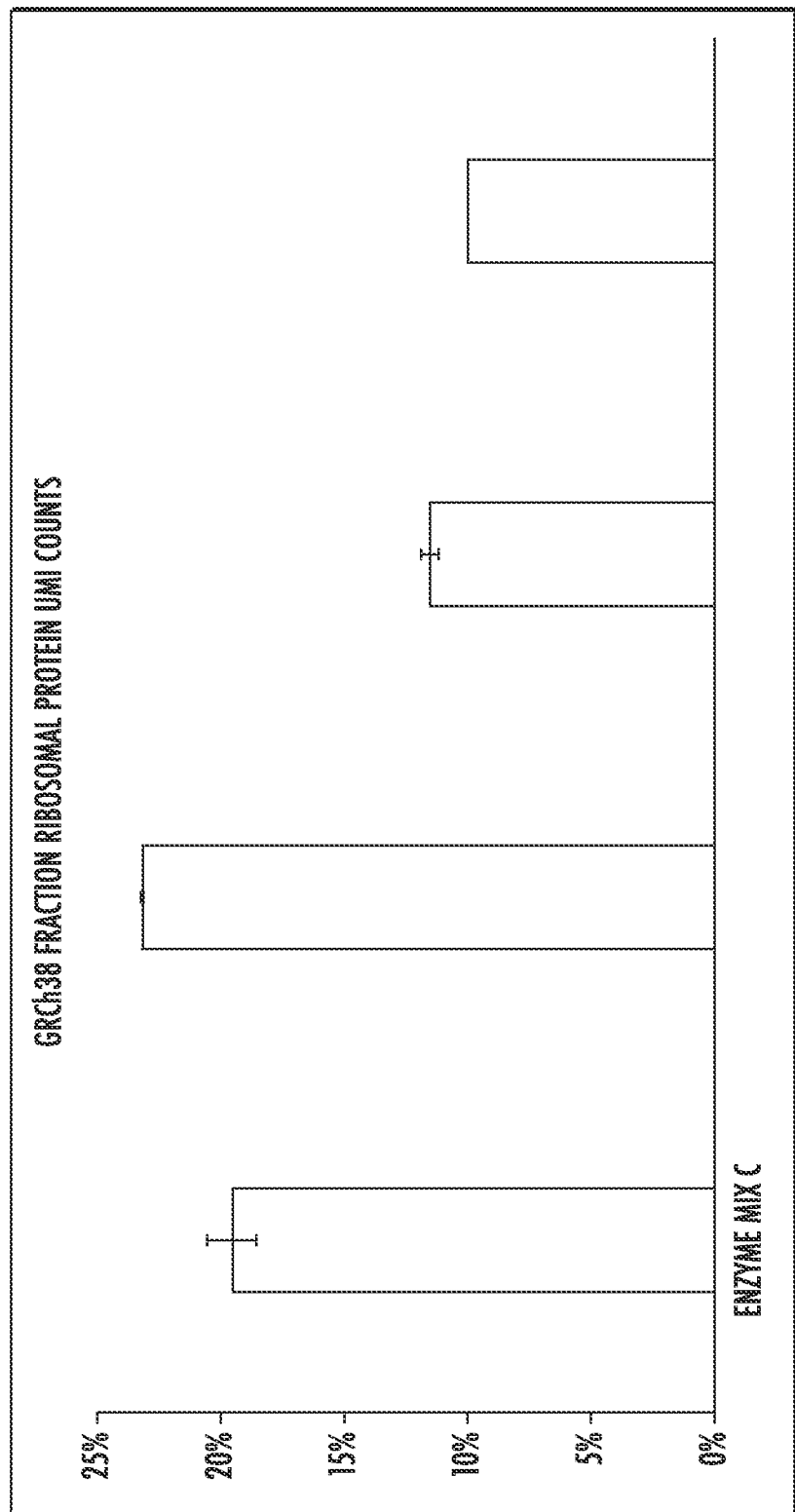
FIG. 10 provides a chart summarizing the fraction of ribosomal protein UMI counts when the indicated engineered reverse transcriptases (Enzyme Mix C, SEQ ID NO:1, variant AO and variant AK) were used in a GEM-X assay.
Figure 11:
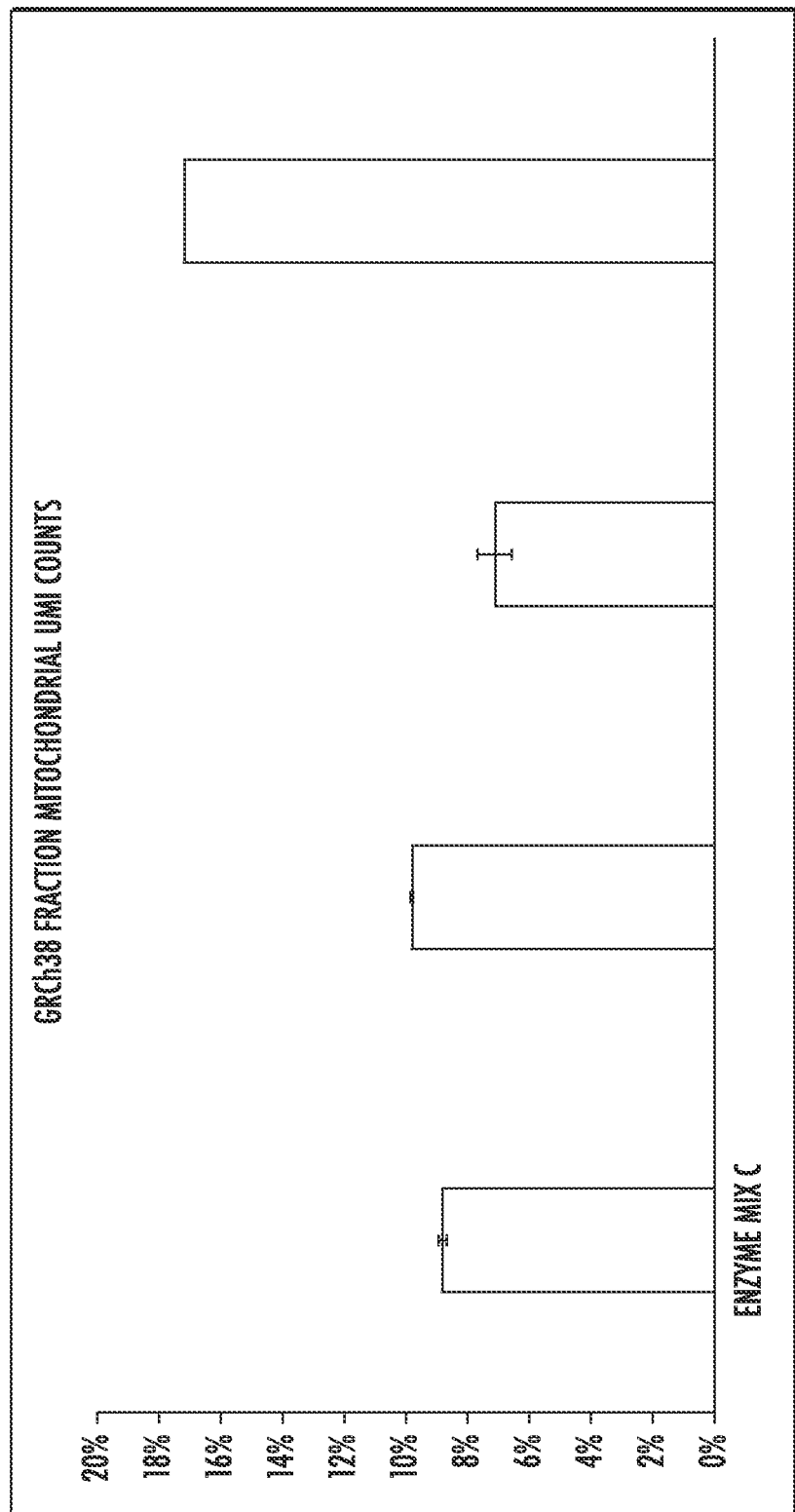
FIG. 11 provides a chart summarizing the fraction of mitochondrial protein UMI counts when the indicated engineered reverse transcriptases (Enzyme Mix C, SEQ ID NO:1, variant AO and variant AK) were used in a GEM-X assay.

GEM-x reactions were performed on peripheral blood monocytes (PBMC) cells with a variety of reverse transcriptases. The percent of valid barcodes was determined. In one experiment, Enzyme Mix C, an enzyme comprising the amino acid sequence set forth in SEQ ID NO:1, and engineered reverse transcriptases (AO) and (AK) were evaluated. Results of one such experiment are shown in FIG. 6. The percent of reads confidently mapped to the transcriptome was determined. Results of one such experiment are summarized in FIG. 7. The median number of genes detected per cell over 20,000 raw reads per cell was determined. Results of one such experiment are summarized in FIG. 8. The median UMI counts detected per cell over 20,000 raw reads per cell was determined. Results of one such experiment are summarized in FIG. 9. The fraction of ribosomal protein UMI counts was determined. Results of one such experiment are summarized in FIG. 10. The fraction of mitochondrial protein UMI counts was determined. Results of one such experiment are summarized in FIG. 11.

In another experiment SEQ ID NO:1 and engineered reverse transcriptase variants AJ, AG and AF were evaluated. The median number of genes detected per cell normalized was determined. Results of one such experiment are summarized in FIG. 12. The enzymes were tested in V(D)J 5' v1 with 1,000 peripheral blood monocytes (PBMC) cell load on the GEM-U chip (737 k diversity gel bead build).

Example 5. Median Genes Detected Per Cell Normalized

Figure 12:
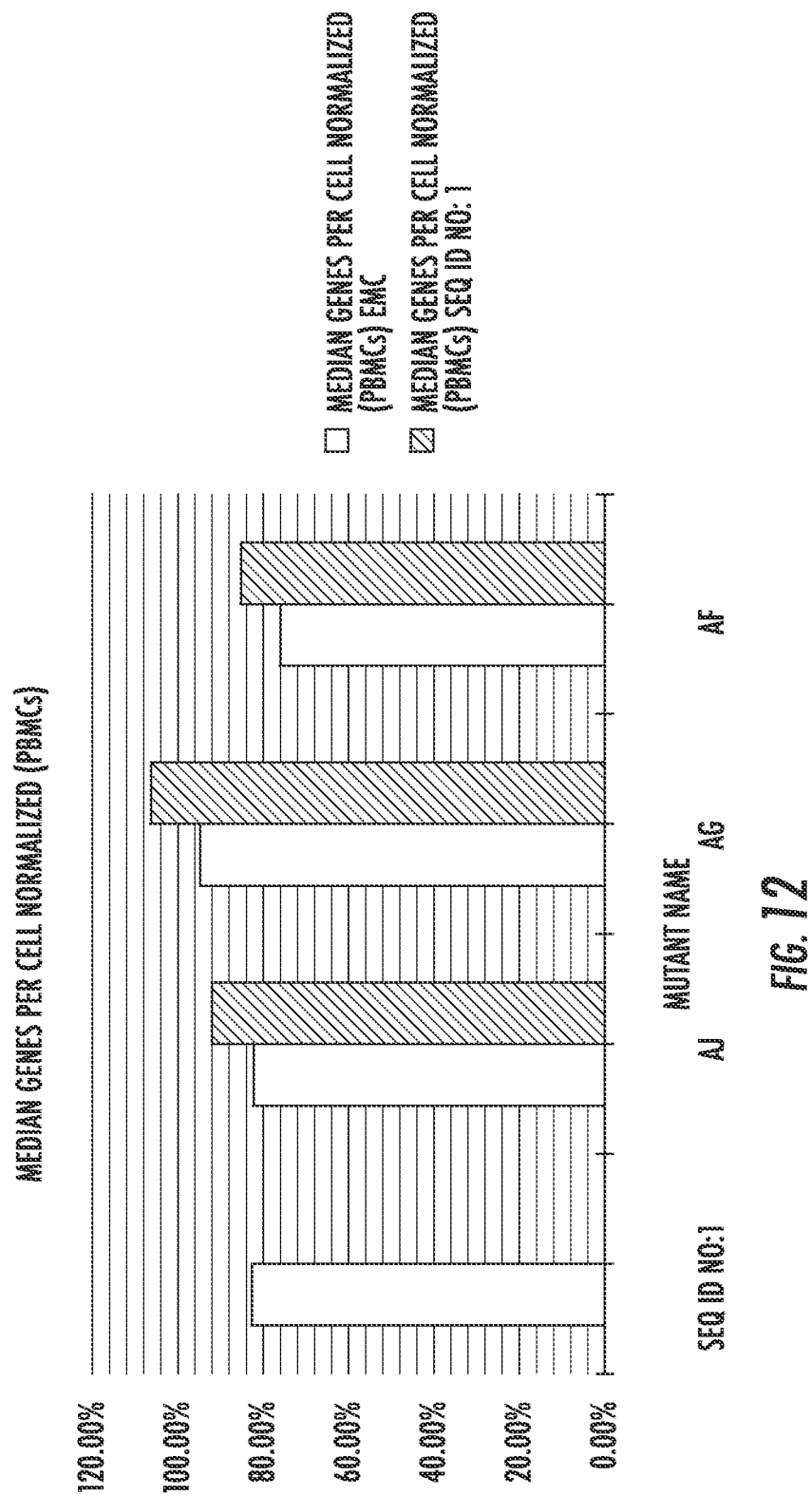
FIG. 12 provides a chart comparing the median genes per cell normalized to either SEQ ID NO:1 or Enzyme Mix C (EMC).

Variant engineered reverse transcriptases were used in GEM-X reactions with peripheral blood monocytes (PBMC) cells. The median UMI/cell was determined. The median number of genes detected per cell was determined, as described above herein. Results of one such series of experiments are shown in FIG. 12.

Example 6. Transcription Efficiency and Template Switching Efficiency Analysis

CE reactions are performed with a variety of RNA templates. The RNA templates are longer, contain more secondary structure, have more complex nucleotide sequence or a combination of the above. The reactions are performed similarly and transcription efficiency and template switching efficiency are calculated. Reactions are performed with an engineered reverse transcriptase of interest. Alternatively, the products are evaluated with gel electrophoresis.

Example 7. Mean Read/Cell Assessment

Figure 13A:
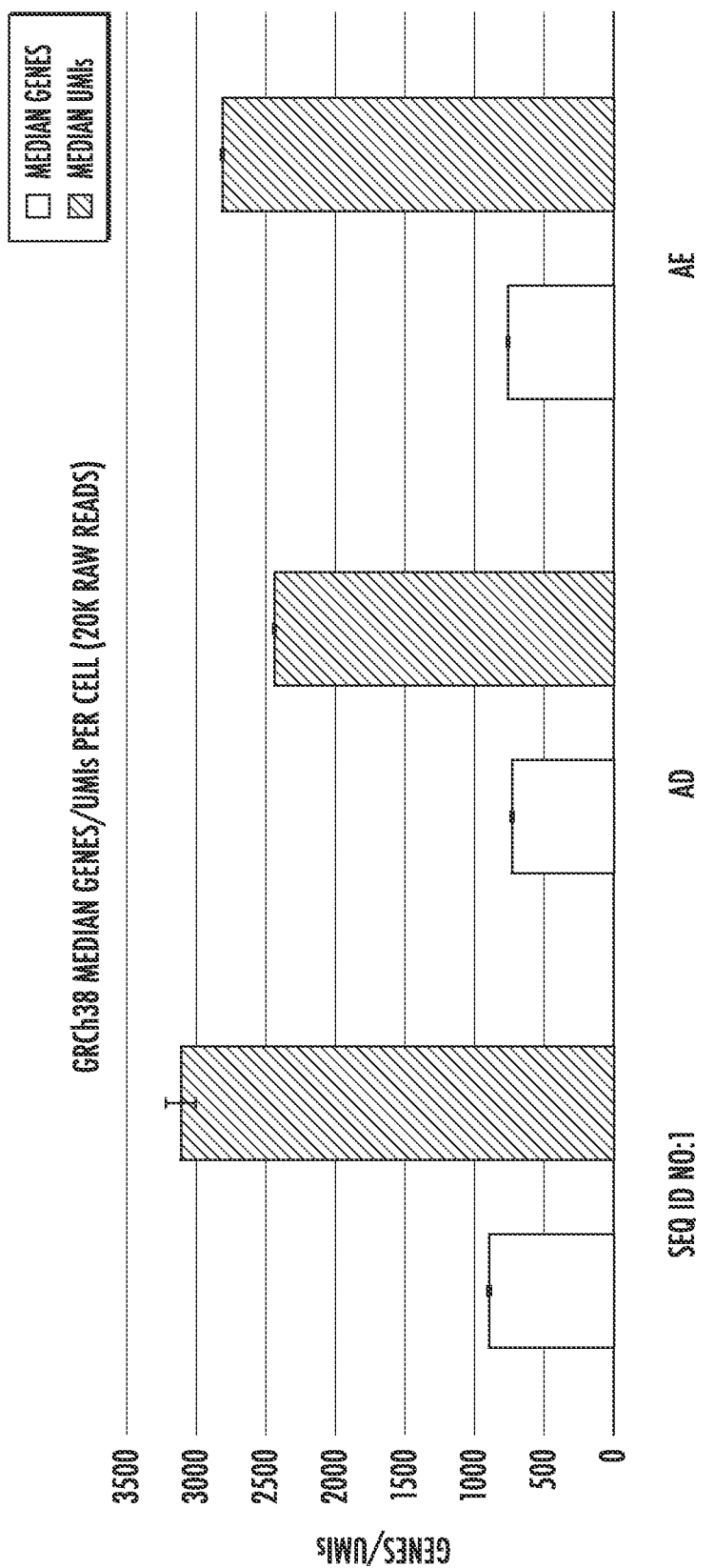
Figure 13B:
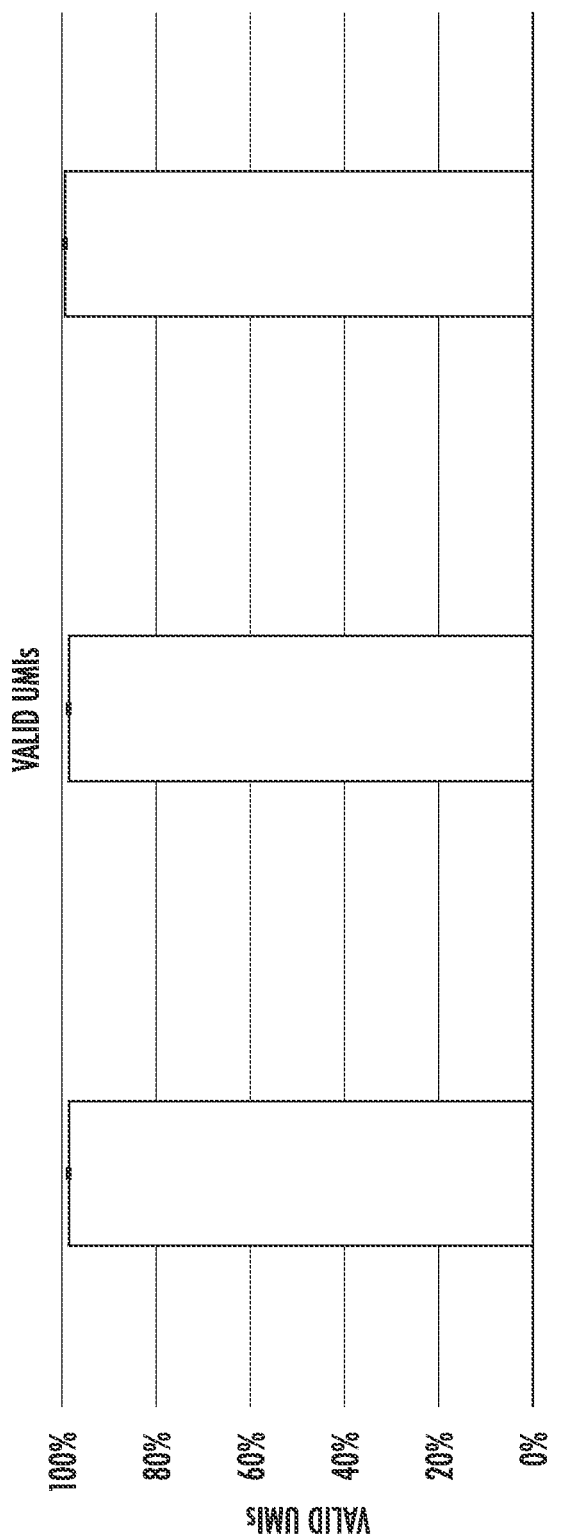
Figure 13C:
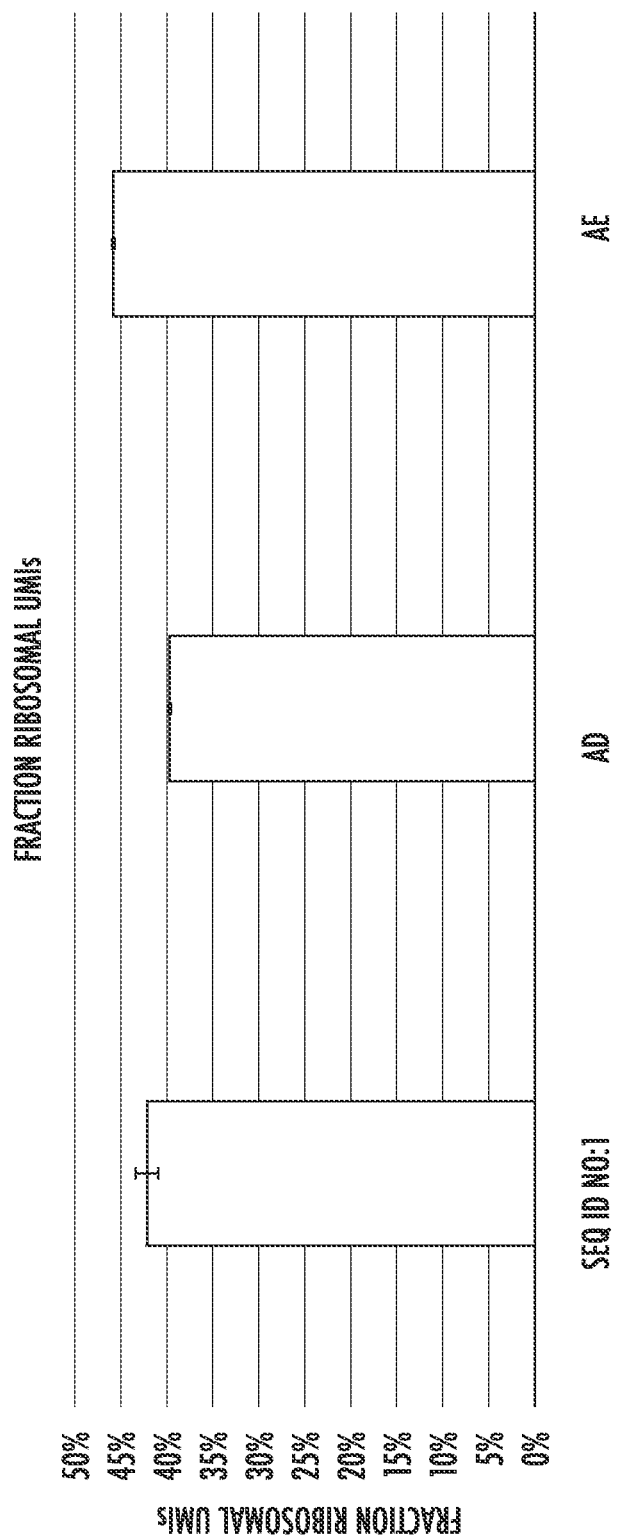
Figure 13D:
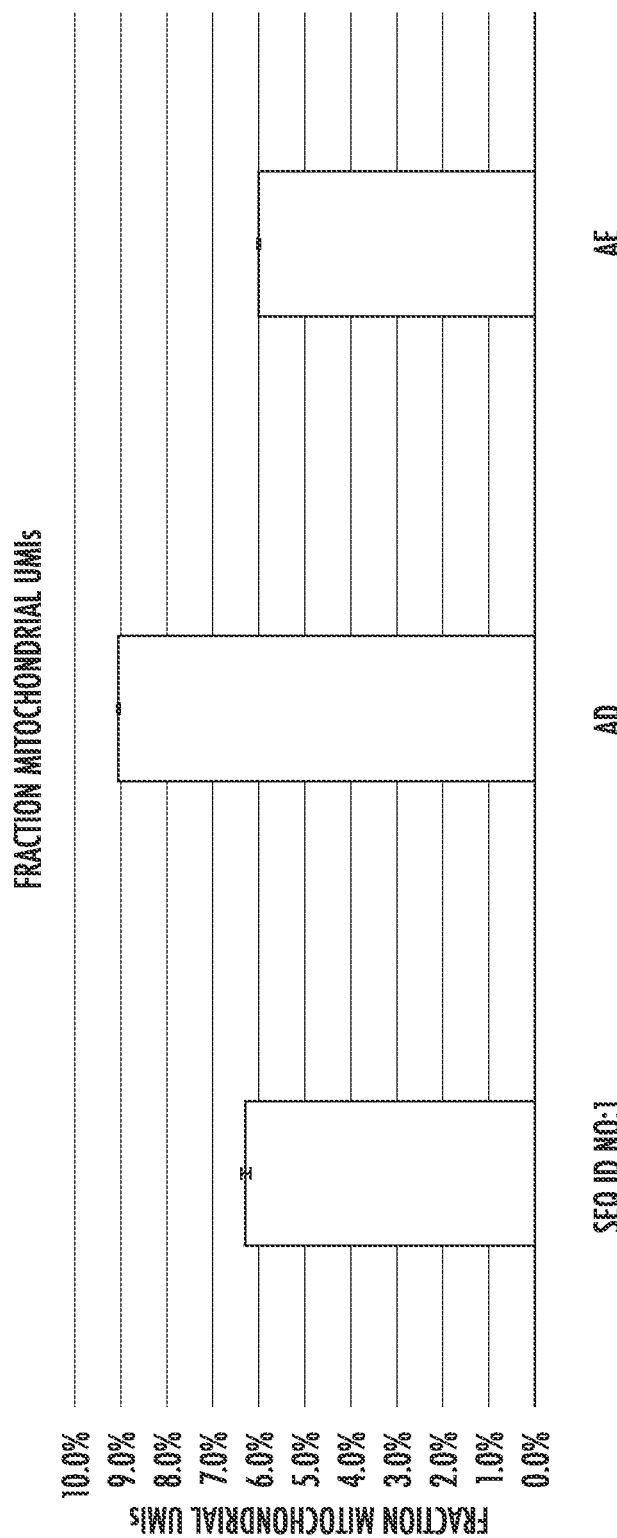

GEM-x reactions were performed on peripheral blood monocytes (PBMC) cells with a variety of reverse transcriptases. The percent of valid barcodes was determined. In one experiment, an enzyme having the amino acid sequence set forth in SEQ ID NO:1 and engineered reverse transcriptase variants AD and AE were evaluated. Results of one such experiment are shown in FIG. 13A. The median number of genes detected per cell over 20,000 raw reads per cell was determined. Results of one such experiment are summarized in FIG. 13A. The median UMI counts detected per cell over 20,000 raw reads per cell was determined. Results of one such experiment are summarized in FIG. 13B. The fraction of ribosomal protein UMI counts was determined. Results of one such experiment are summarized in FIG. 13C. The fraction of mitochondrial protein UMI counts was determined. Results of one such experiment are summarized in FIG. 13D.

Example 8. Transcription Efficiency and Template Switching Efficiency Analysis

Figure 14:
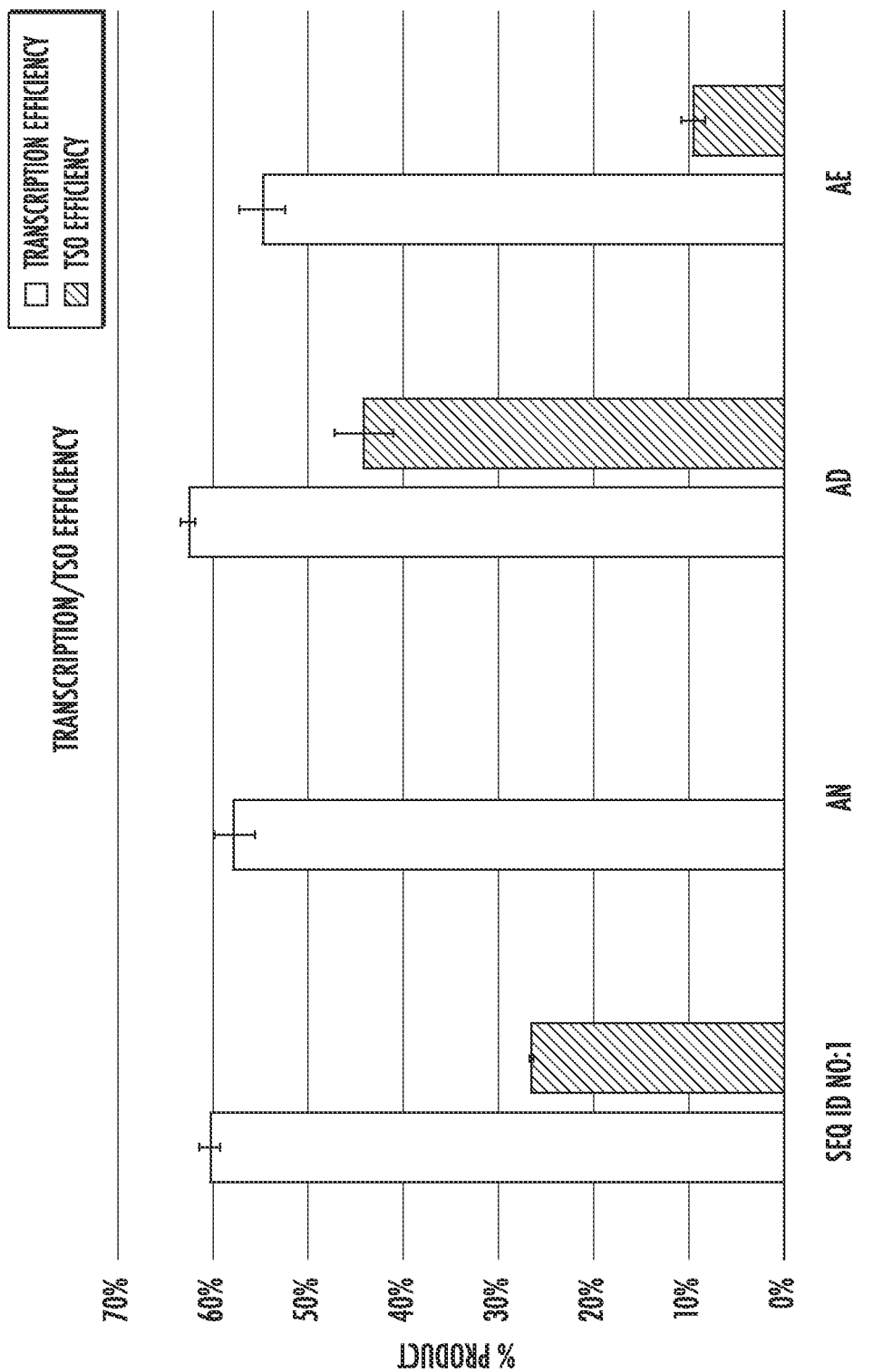
FIG. 14 provides a chart comparing the transcription efficiency and template switching efficiency of multiple engineered reverse transcriptases. Bars indicating the transcription efficiency are indicated on the left for each enzyme tested; bars indicating the template switching efficiency are indicated on the right for each enzyme tested. The percent product is indicated on the y axis; the enzyme tested is indicated on the x axis. Results from SEQ ID NO:1 and the engineered proteins: AN, AD and AE are shown. Transcription efficiency for all four enzymes exceeds 50%. Template switching efficiency for AD is higher than that of SEQ ID NO:1. Template switching efficiency for AE is lower than that of SEQ ID NO:1. Transcription efficiency for AN was substantially higher than the template switching efficiency of AN.

CE reactions were performed generally as described above herein using a variety of reverse transcriptases and engineered reverse transcriptases. The transcription efficiency and template switching efficiency as a percent product were determined. Results from one such series of experiments are shown in FIG. 14.

Example 9. Temperature Effect Analysis

Figure 15:
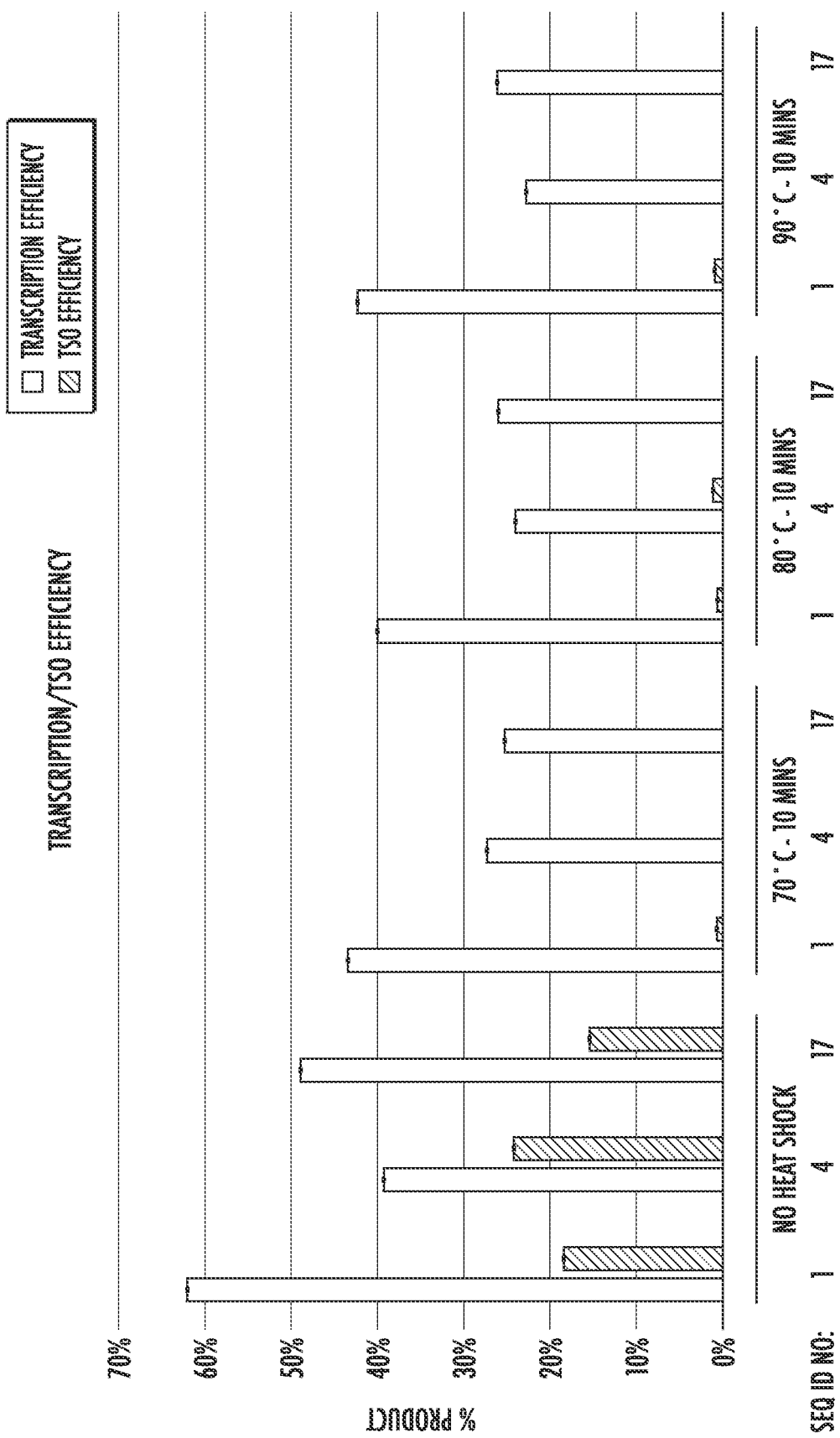
FIG. 15 provides a chart comparing the transcription efficiency and template switching efficiency of multiple engineered reverse transcriptases at standard and elevated temperatures. Bars indicating the transcription efficiency are indicated on the left for each enzyme tested; bars indicating the template switching efficiency are indicated on the right for each enzyme tested. The percent product is indicated on the y axis; the tested enzyme and the heat shock conditions are indicated on the x axis. Results from an enzyme having the amino acid sequence set forth in SEQ ID NO:1 and the engineered proteins encoded by the nucleotide sequences set forth in SEQ ID NO:4 and SEQ ID NO: 17 are shown. Template switching activity is significantly reduced when the variants are subjected to the indicated elevated temperatures. In the absence of heat shock, the variant encoded by the nucleotide sequence set forth in SEQ ID NO:4 exhibited increased template switching activity compared to SEQ ID NO:1. In the absence of heat shock, the variant encoded by the nucleotide sequence set forth in SEQ ID NO:17 exhibited slightly decreased template switching compared to an enzyme having the amino acid sequence set forth in SEQ ID NO:1. All three engineered reverse transcriptases exhibited reduced transcription efficiency when subjected to elevated temperatures.

Engineered reverse transcriptases were subjected to high temperatures (heat-shocked) for 10 minutes. The elevated temperatures were 70° C., 80° C. and 90° C. CE reactions were performed generally as described above herein using a variety of reverse transcriptases and engineered reverse transcriptases. The transcription efficiency and template switching efficiency as a percent product were determined. Results from one such series of experiments are shown in FIG. 15.

Example 10. Mean Read/Cell Assessment

Figure 16C:
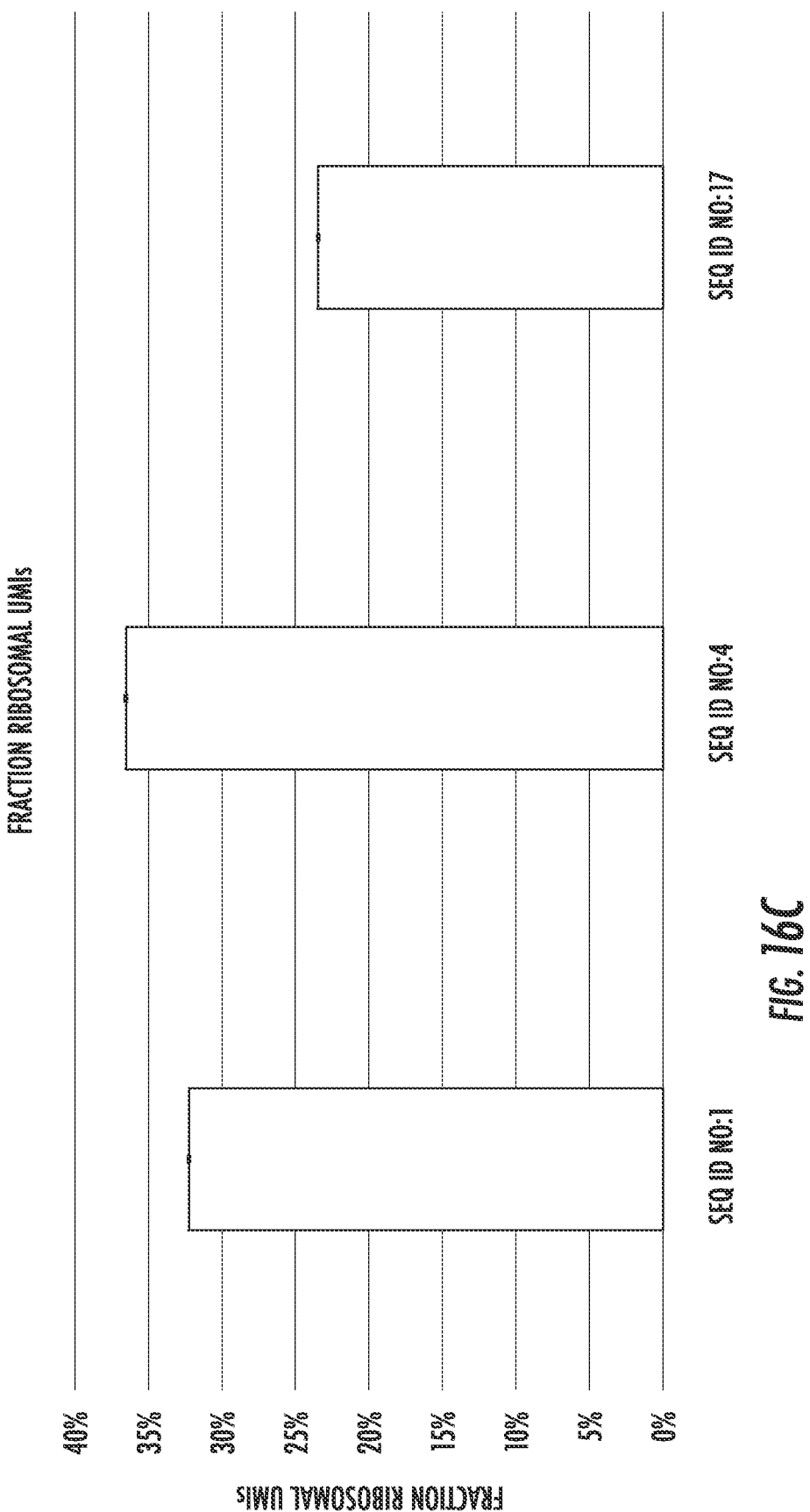
Figure 16D:
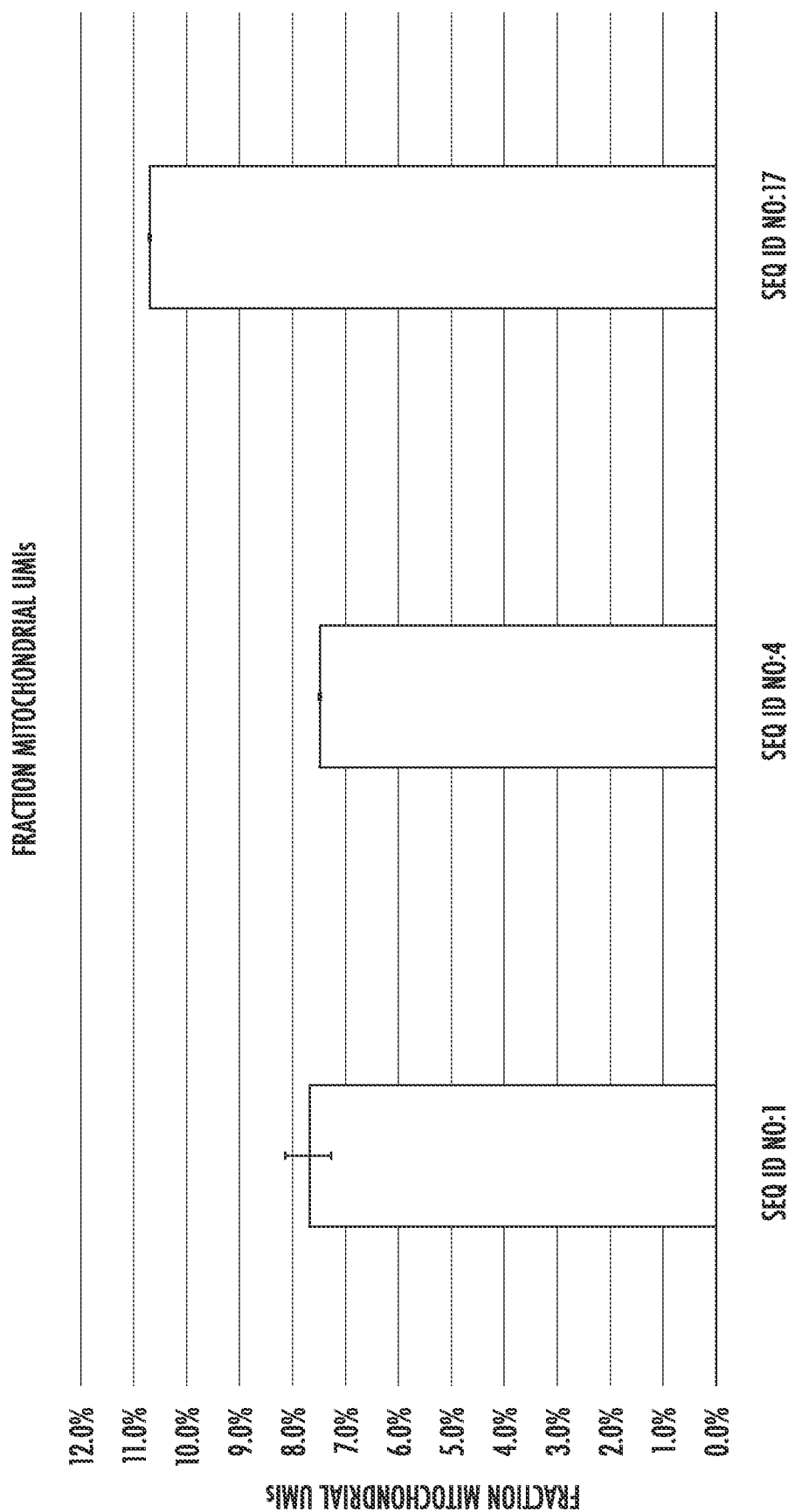

GEM-x reactions were performed with a variety of reverse transcriptases. The percent of valid barcodes was determined. In one experiment, an enzyme having the amino acid sequence set forth in SEQ ID NO:1, and engineered reverse transcriptases having the amino acid sequences encoded by a nucleotide sequence set forth in SEQ ID NO:4 and SEQ ID NO:17 were evaluated. Results of one such experiment are shown in FIG. 16A. The median number of genes detected per cell over 20,000 raw reads per cell was determined. Results of one such experiment are summarized in FIG. 16A. The median UMI counts detected per cell over 20,000 raw reads per cell was determined. Results of one such experiment are summarized in FIG. 16B. The fraction of ribosomal protein UMI counts was determined. Results of one such experiment are summarized in FIG. 16C. The fraction of mitochondrial protein UMI counts was determined. Results of one such experiment are summarized in FIG. 16D.

Example 11 CE Assay Validation v. 2

Figure 17:
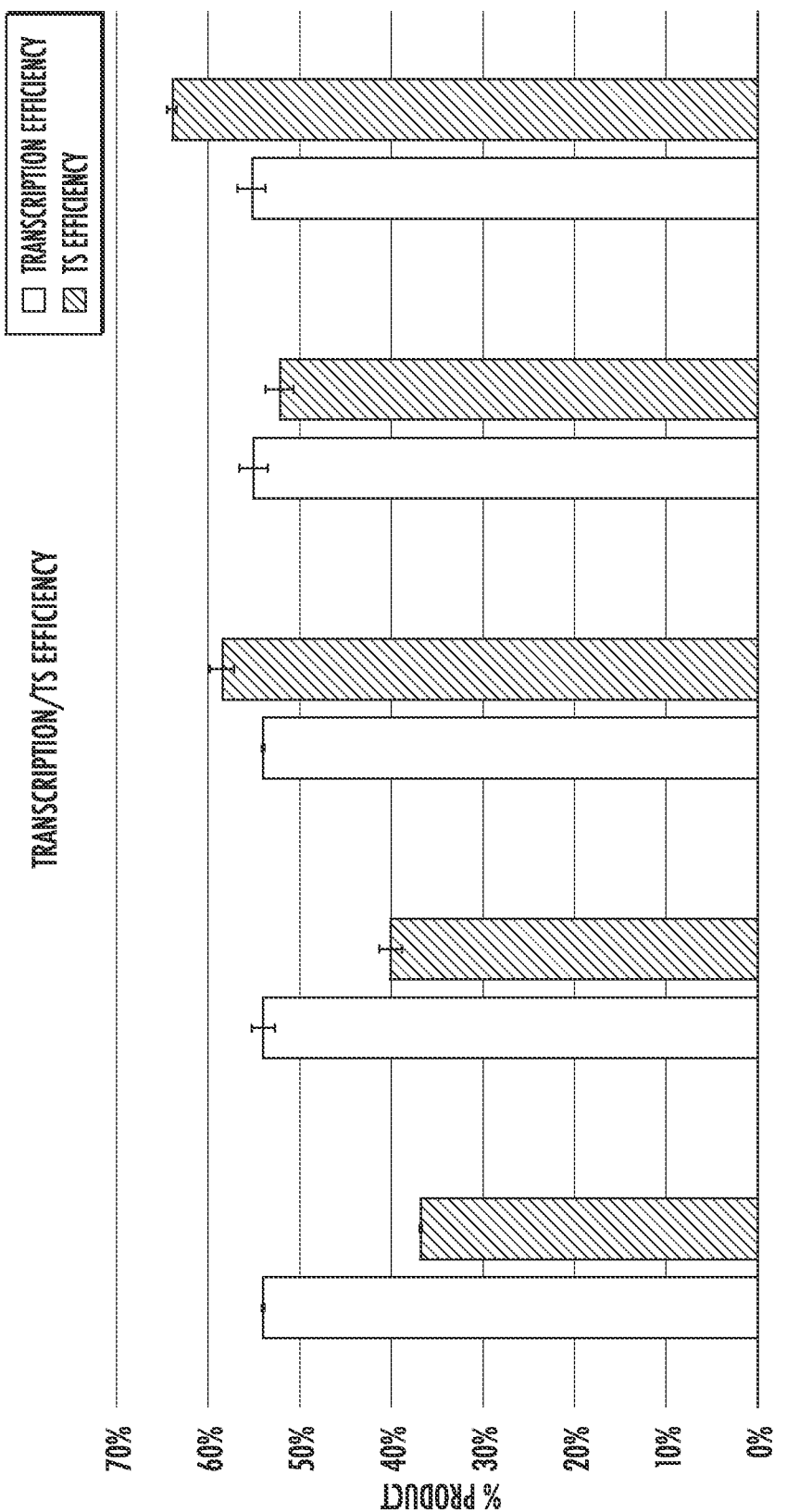
FIG. 17 provides a chart comparing the transcription efficiency and template switching efficiency of multiple engineered reverse transcriptases. Bars indicating the transcription efficiency are indicated on the left for each enzyme tested; bars indicating the template switching efficiency are indicated on the right for each enzyme tested. The percent product is indicated on the y axis; the enzyme tested is indicated on the x axis. Results from the engineered proteins: AF, AA and AB are shown. Transcription efficiency for all four enzymes exceeds 50% and are generally comparable to each other and a commercially available reverse transcriptase enzyme (EMC). EMC refers to Enzyme Mix C containing an enzyme supplied by Qiagen. Template switching efficiency for AF is higher than that of SEQ ID NO:1. Template switching efficiency for AA is lower than that of AF and higher than that of SEQ ID NO:1. Template switching efficiency for AB was substantially higher than the template switching efficiency of SEQ ID NO:1, AF and AA. Reactions were performed as described below herein.
Figure 18A:
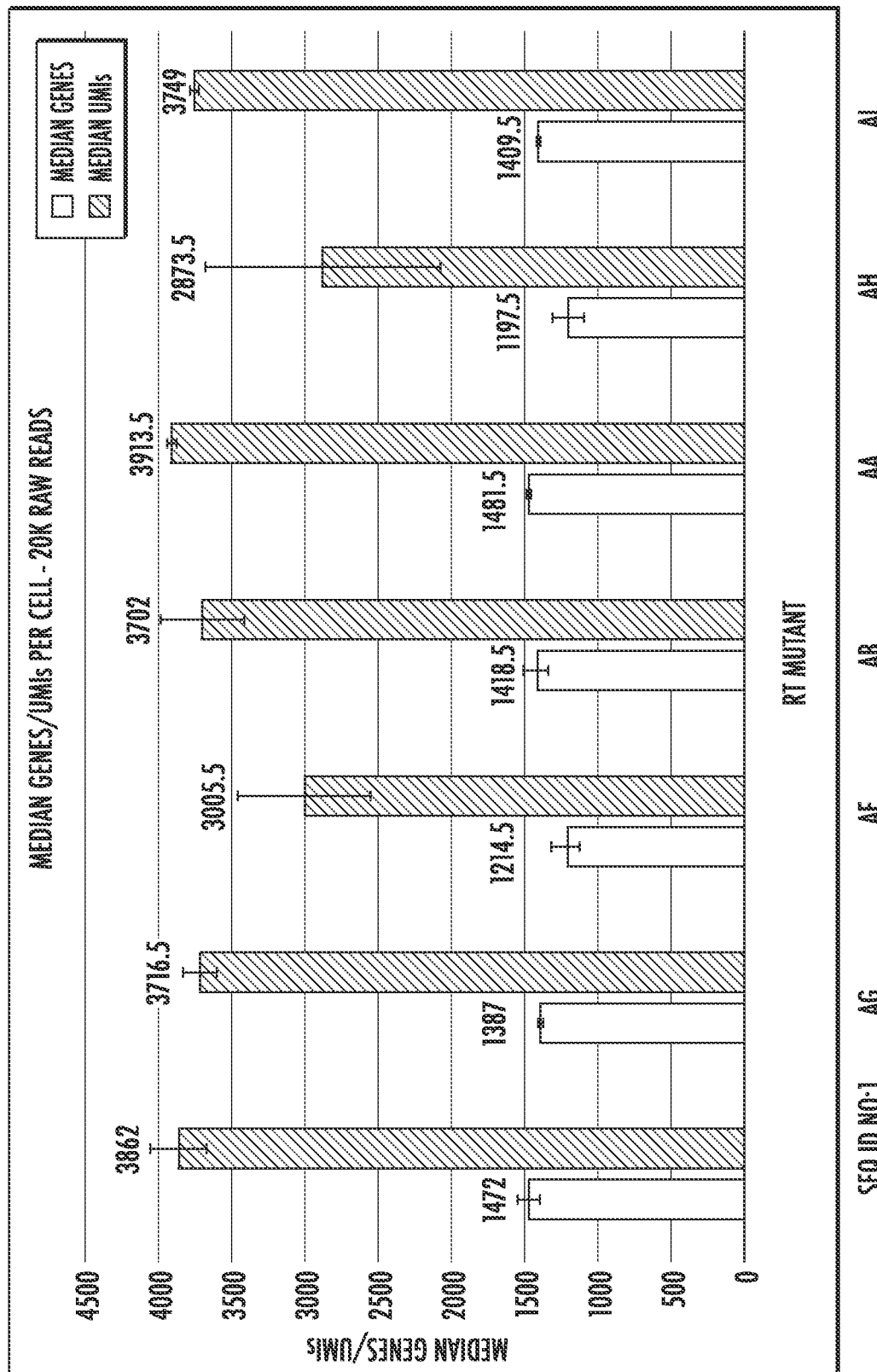
Figure 18B:
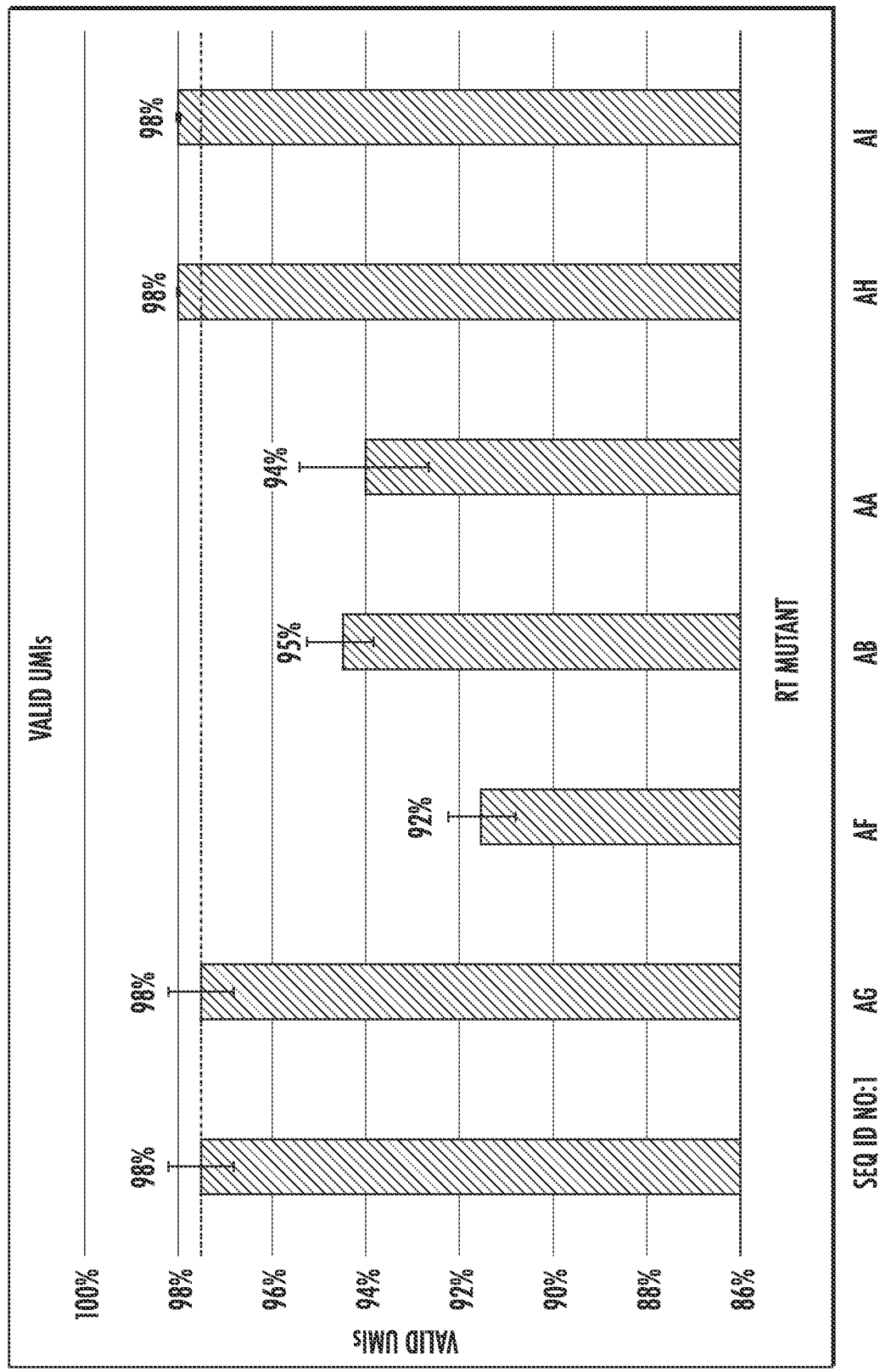
Figure 18C:
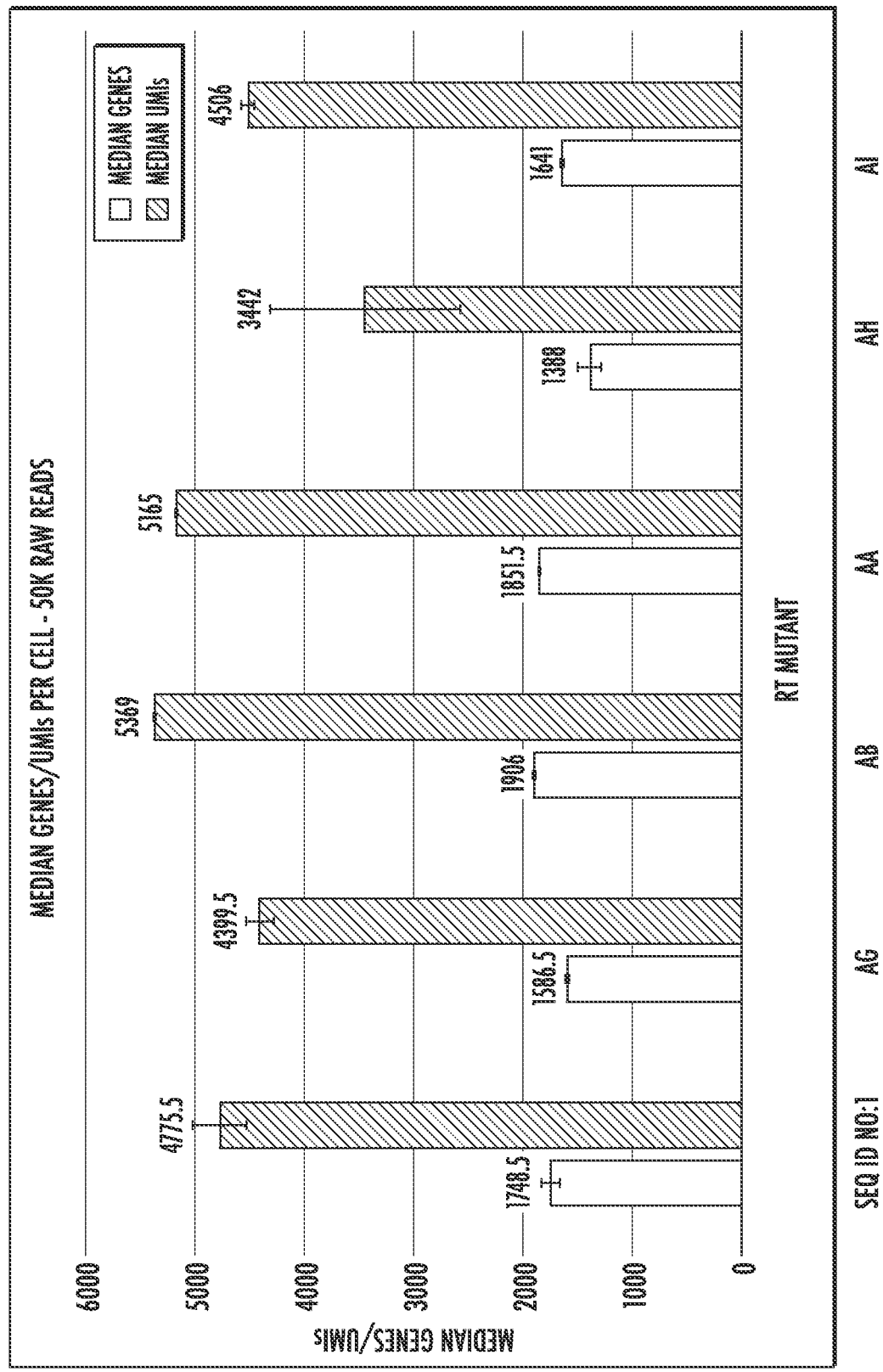
Figure 18D:
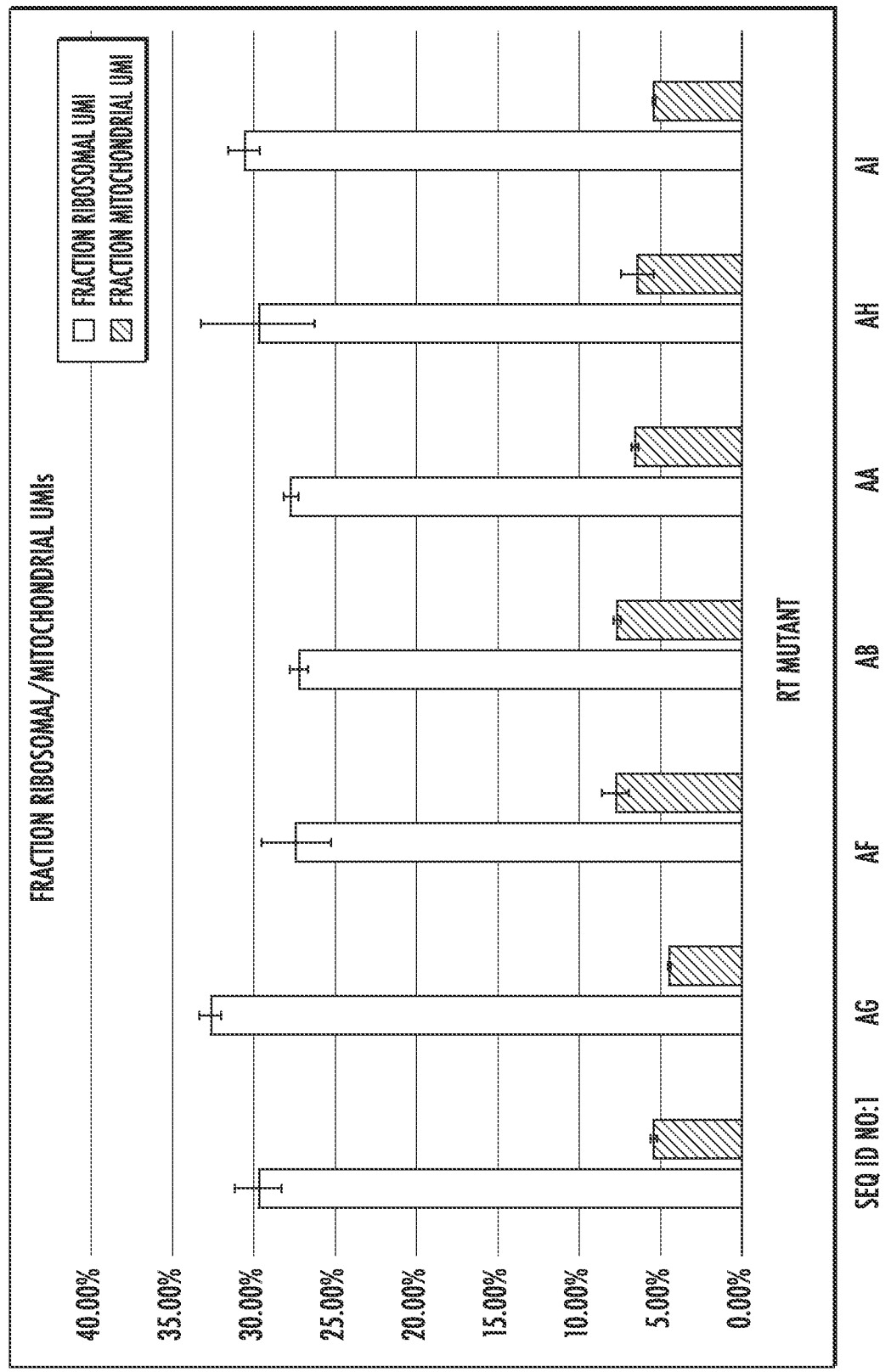
Figure 18E:
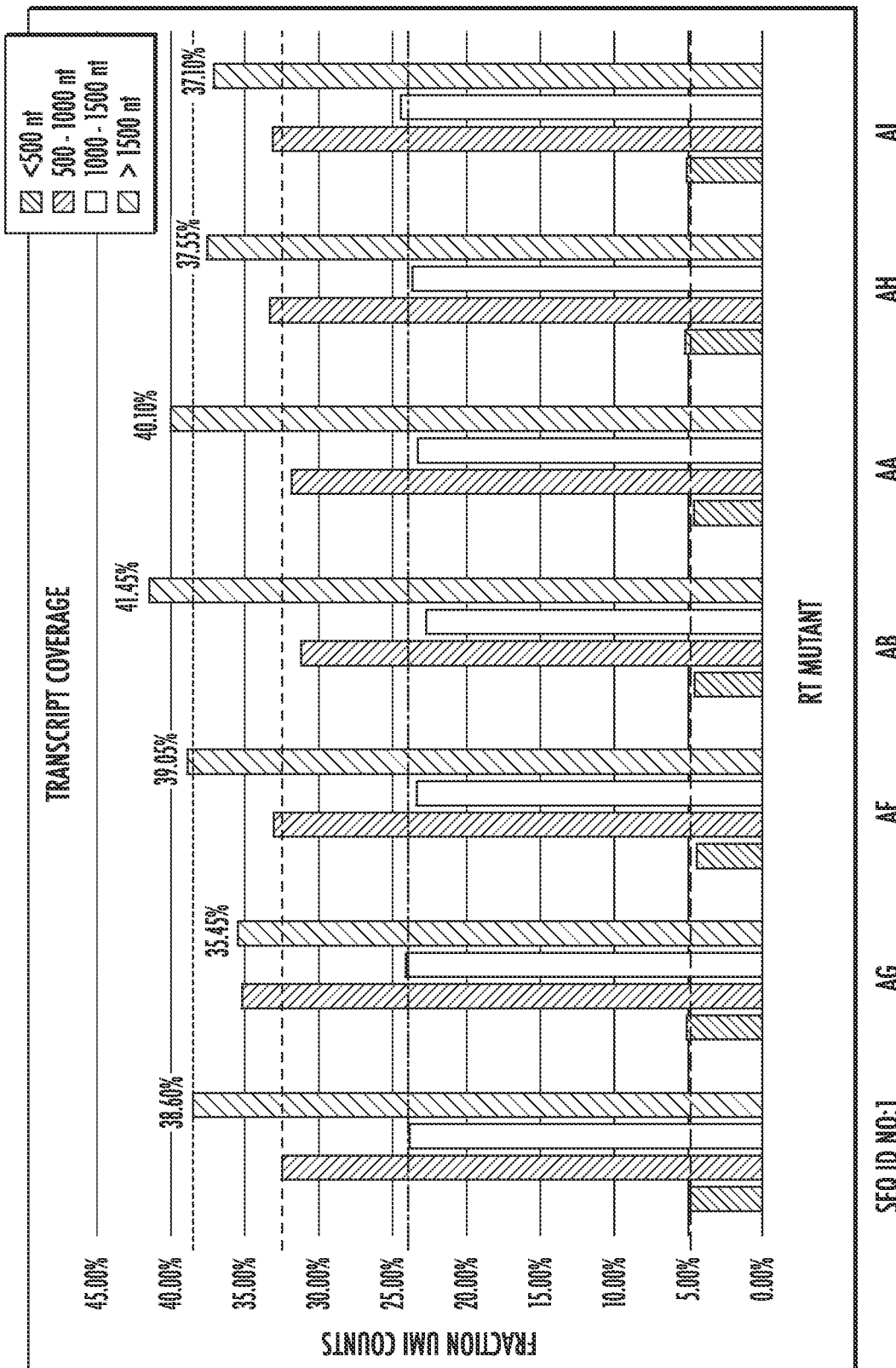
Figure 18F:
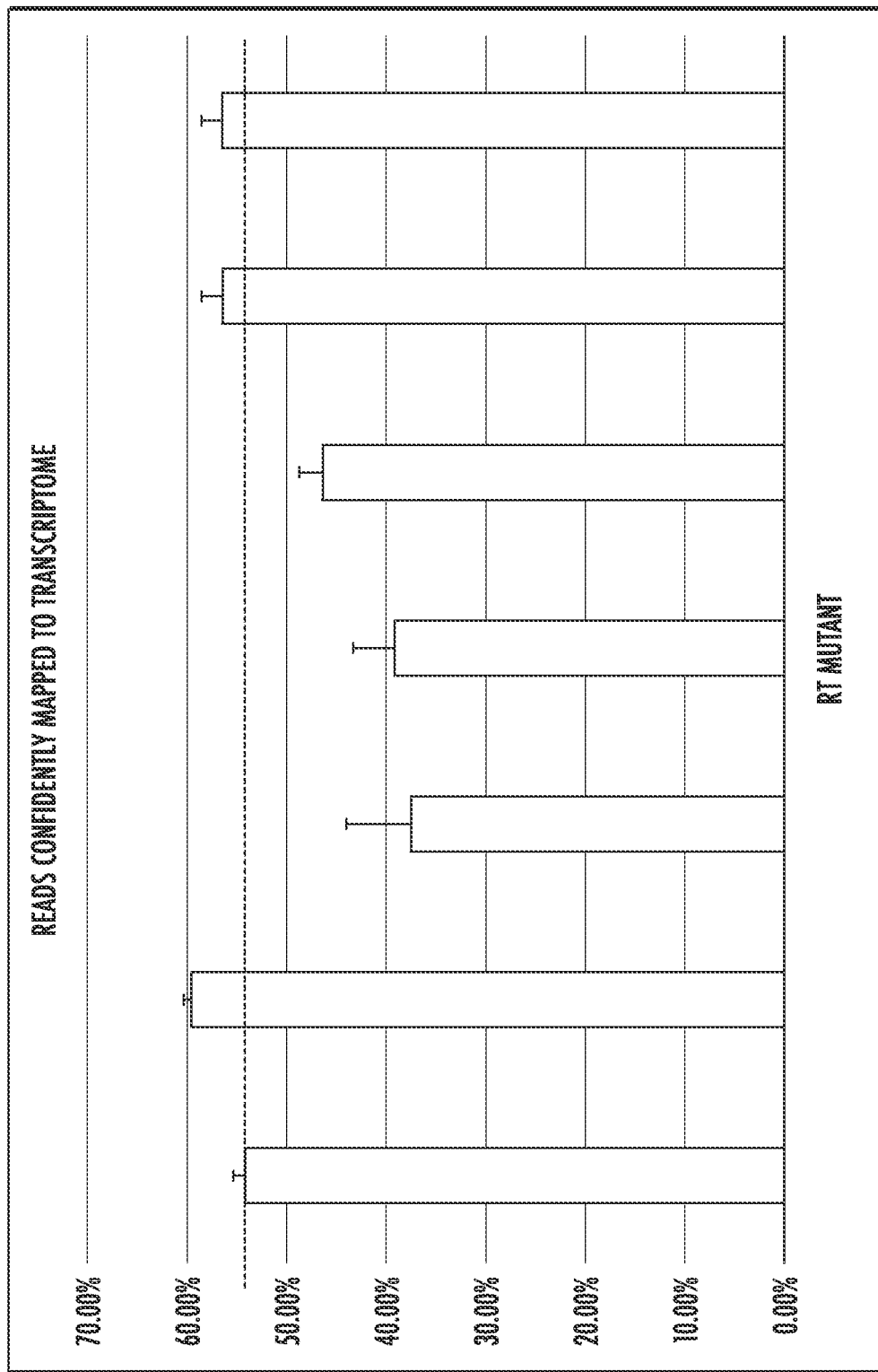
Figure 19:
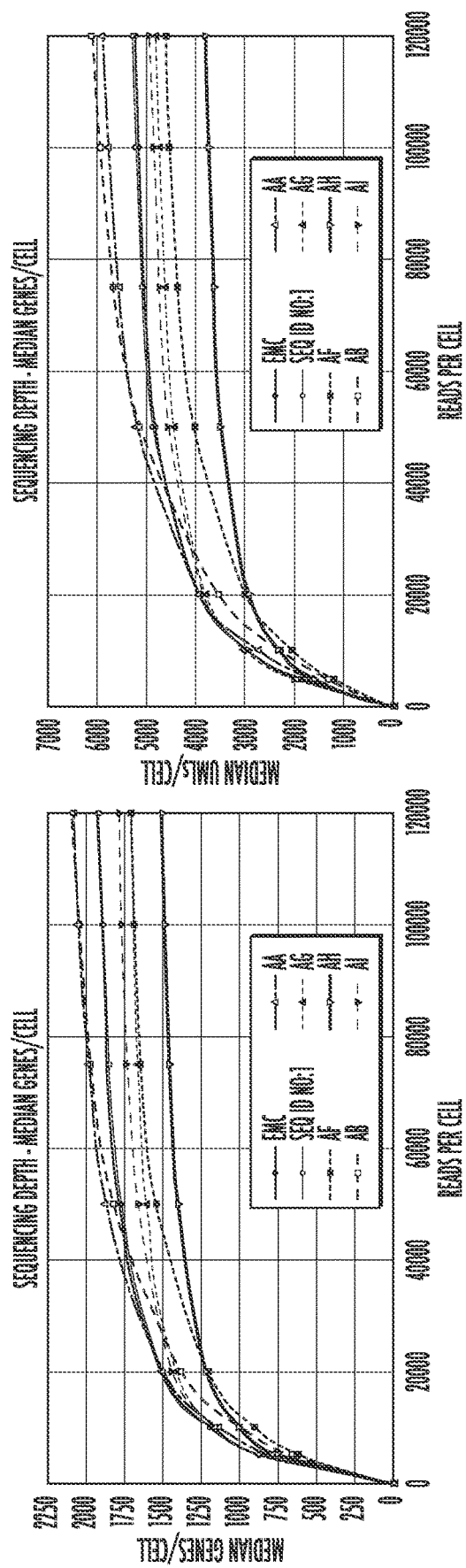
FIG. 19 provides an analysis of sequencing depth. The panel on the left summarizes the median genes/cell as a function of reads per cell for a commercial reverse transcriptase (EMC), an enzyme having the amino acid sequence set forth in SEQ ID NO:1, and variants AF, AB, AA, AG, AH and AI. The panel on the right summarizes the median UMIs/cell as a function of reads per cell for a commercial reverse transcriptase (EMC), an enzyme having the amino acid sequence set forth in SEQ ID NO:1, and variants AF, AB, AA, AG, AH and AI. Variants AA and AB show higher median genes/cell and higher median UMIs/cell than an enzyme having the amino acid sequence set forth in SEQ ID NO:1 or the commercial MMLV.
Figure 20A:
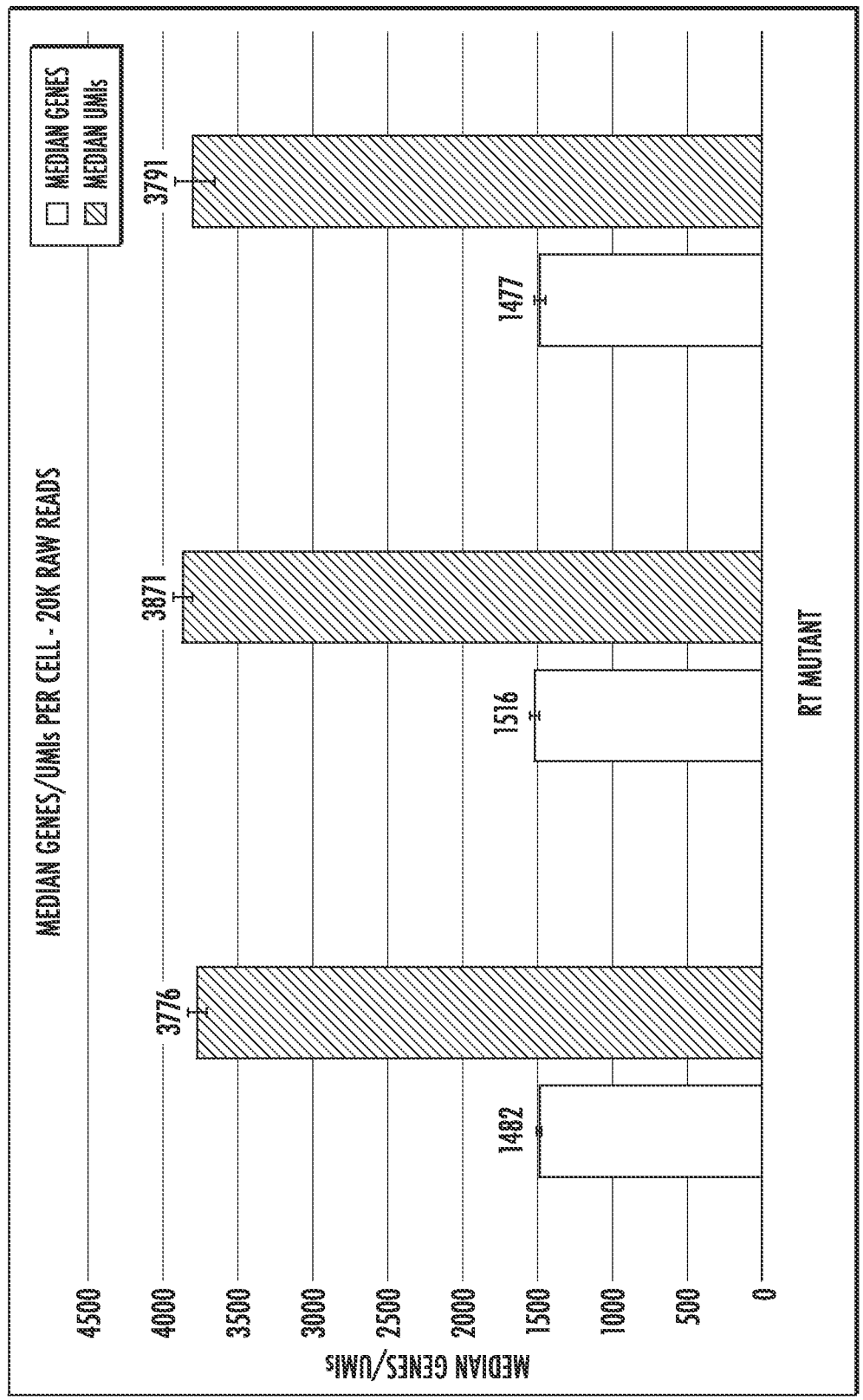
FIGS. 20A-20I provide a summary of data from a series of assays with an enzyme having the amino acid sequence set forth in SEQ ID NO:1, and variants AB and AA.
Figure 20B:
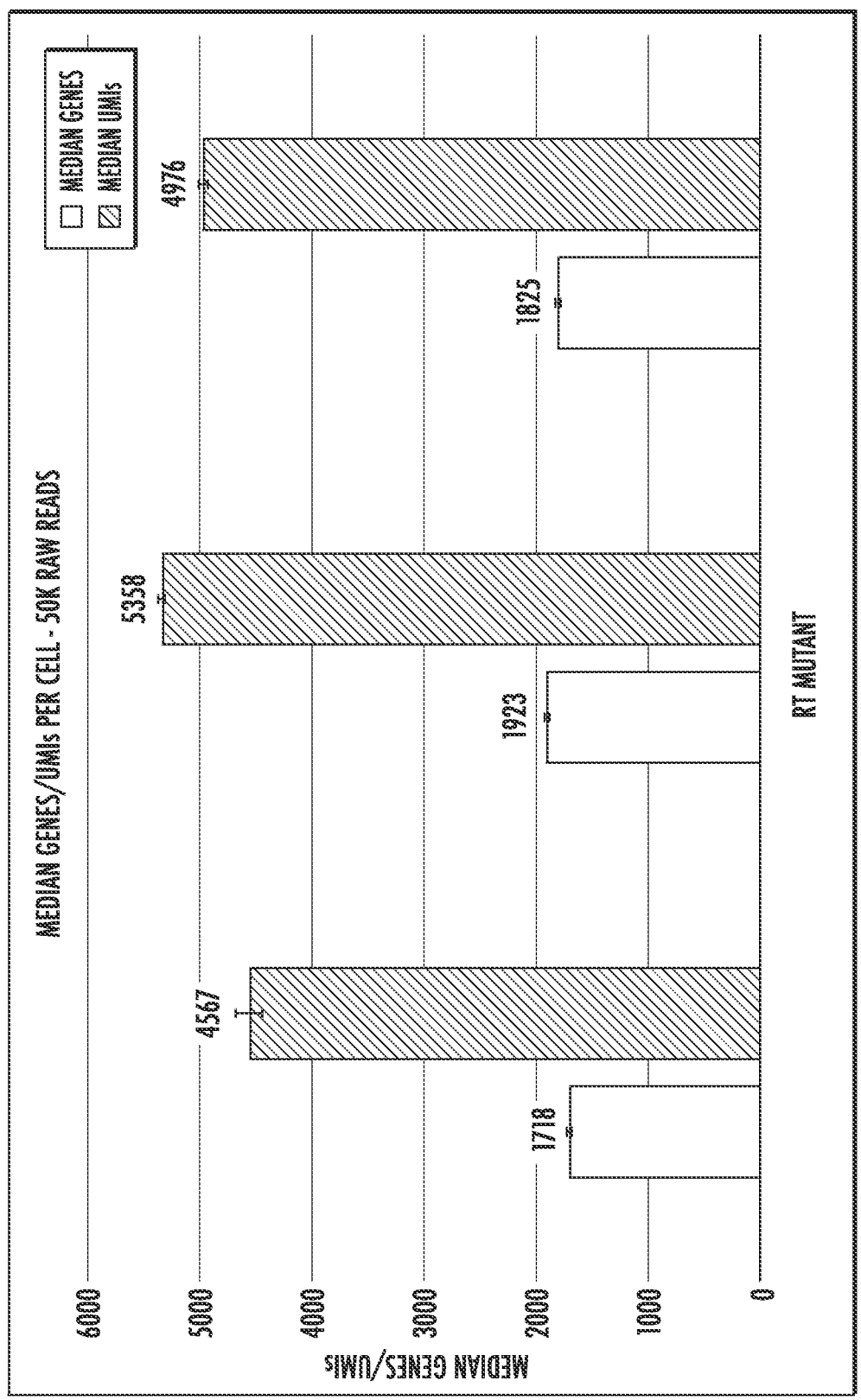
Figure 20C:
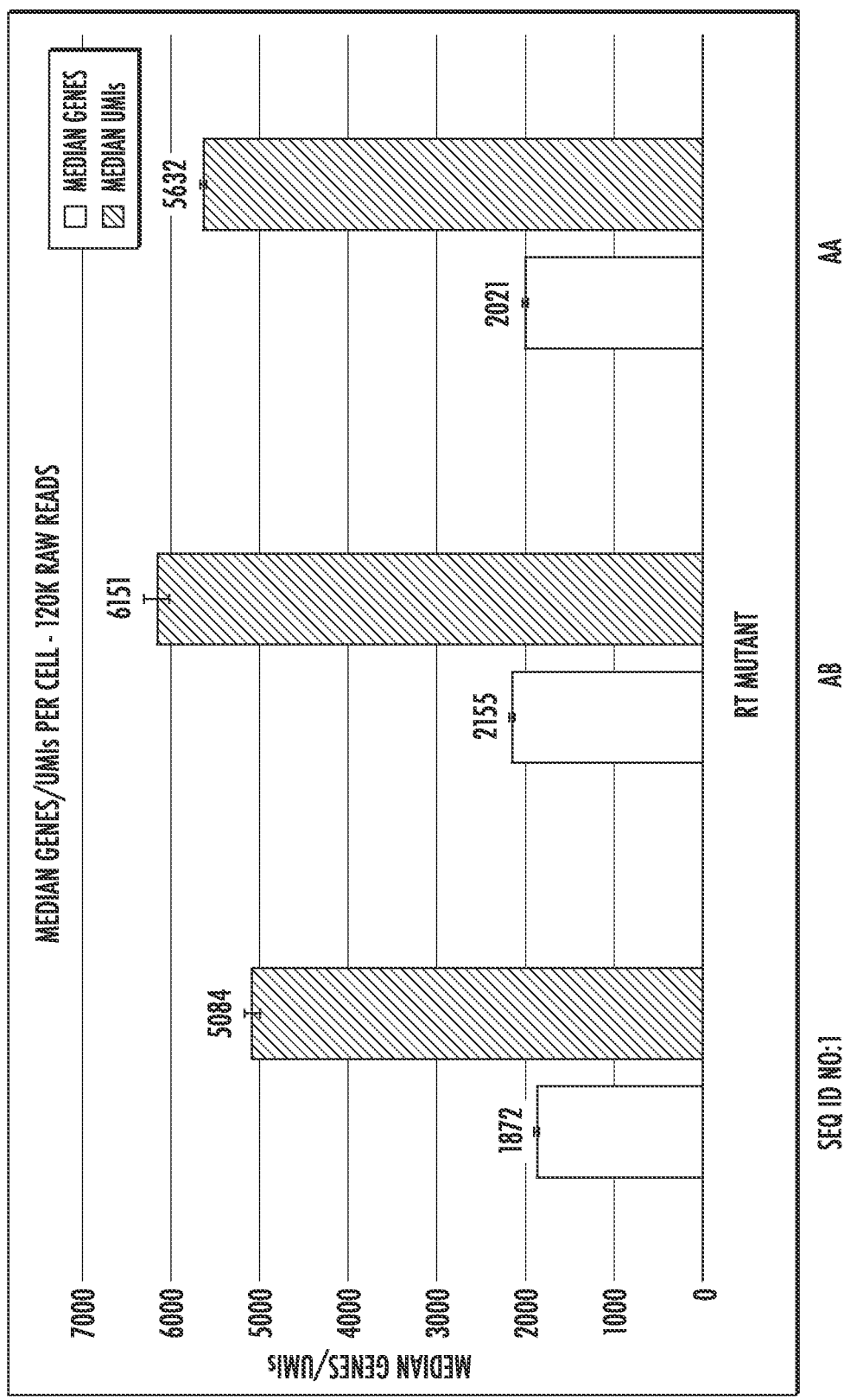
Figure 20D:
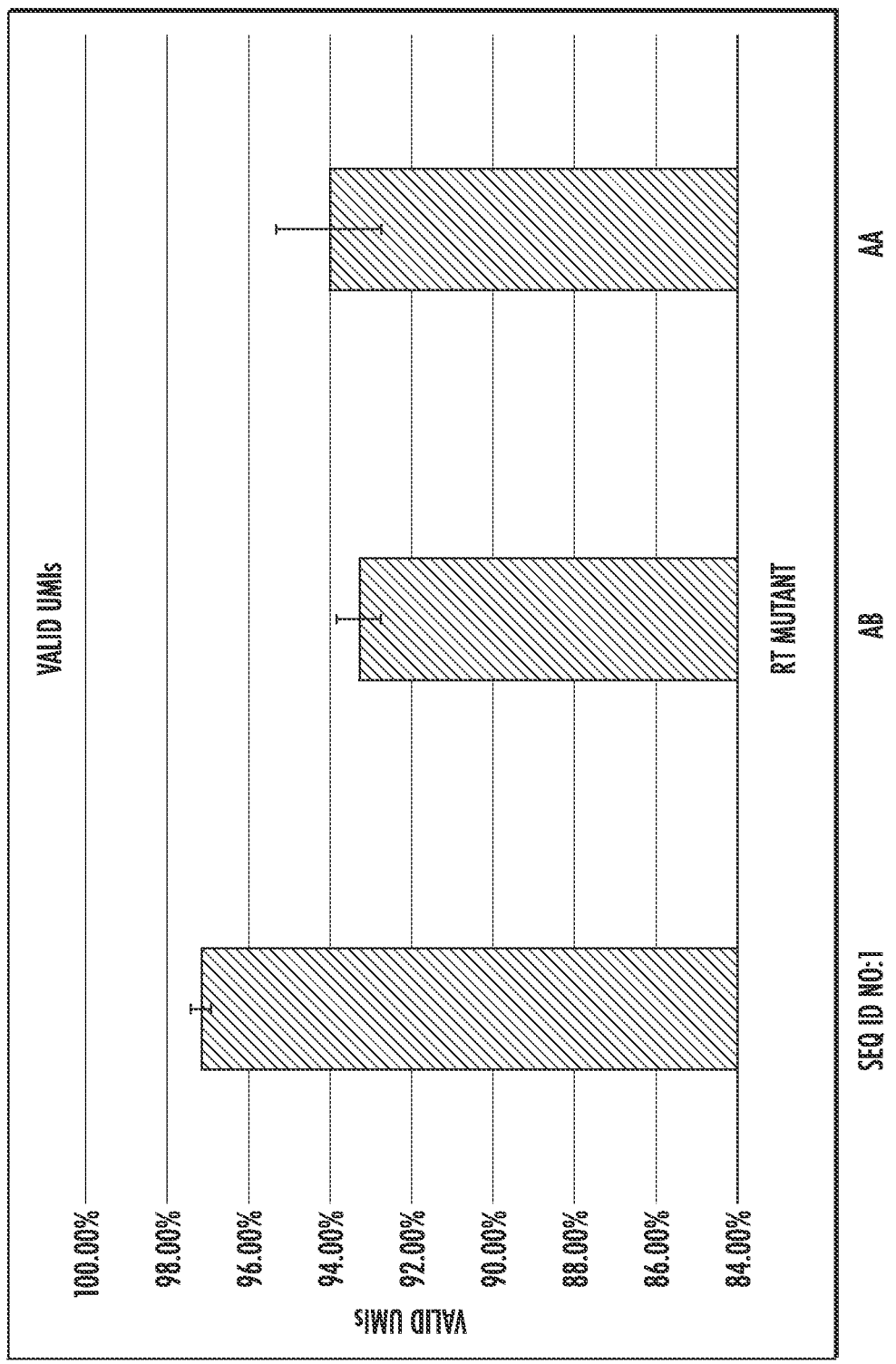
Figure 20E:
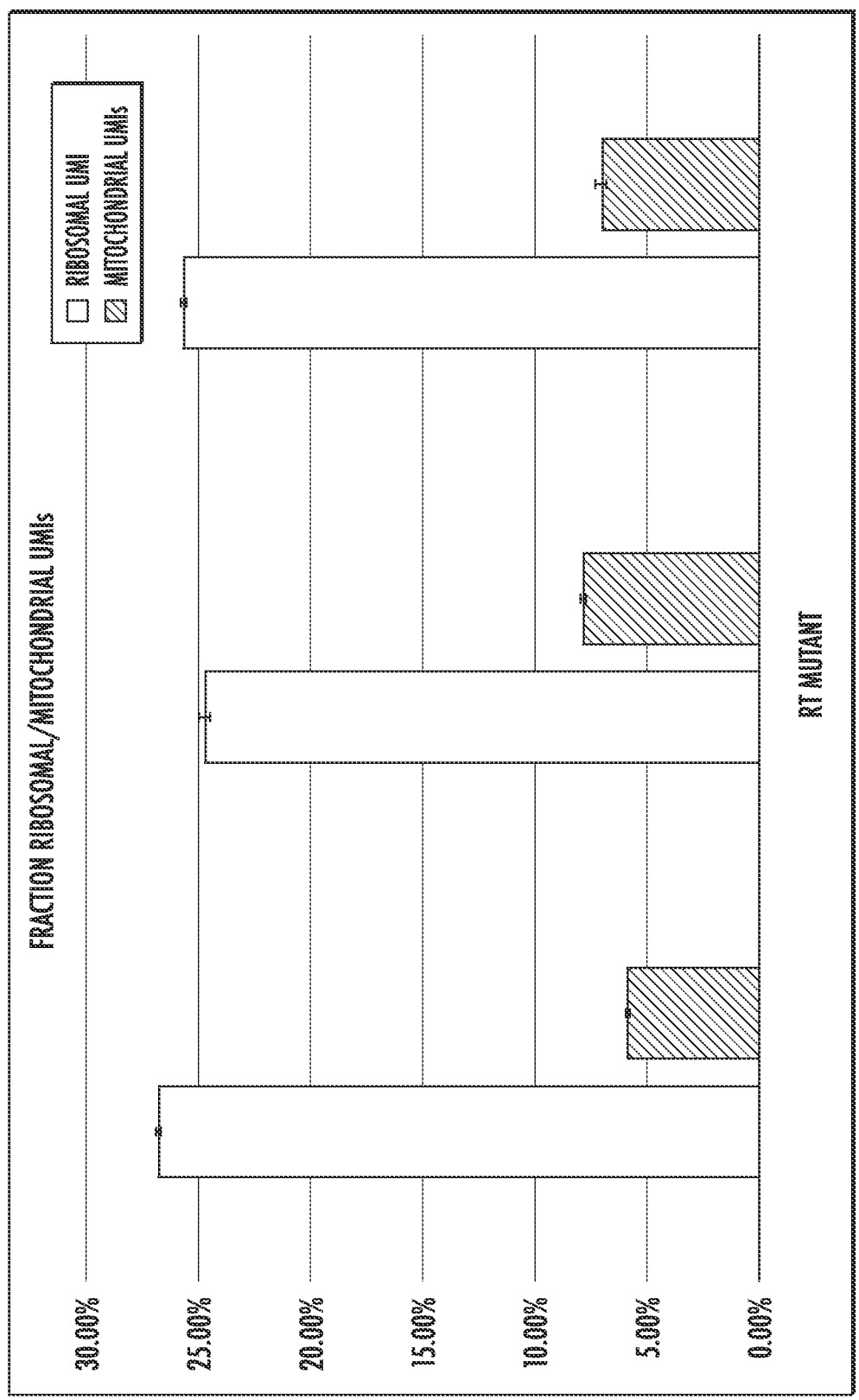
Figure 20F:
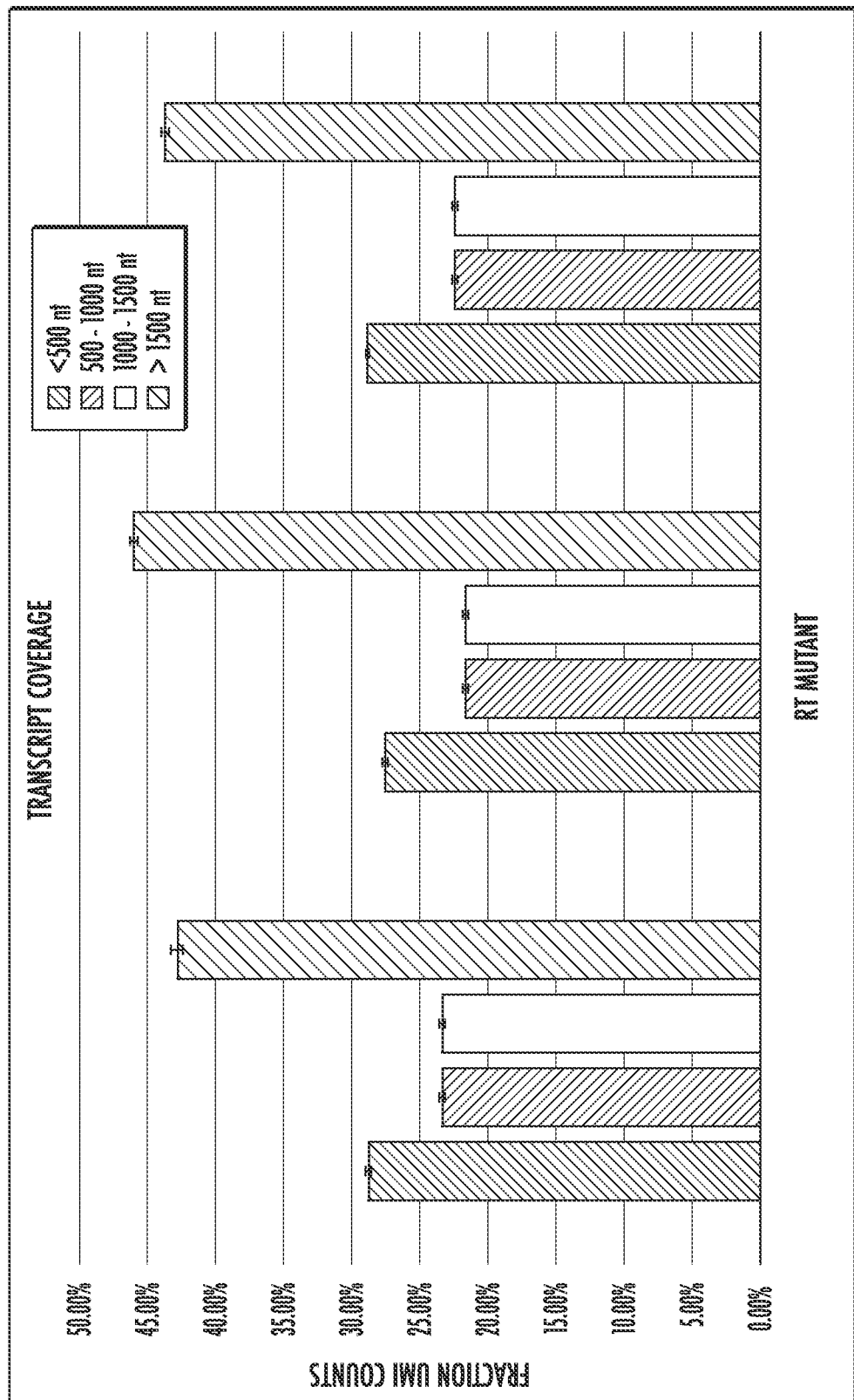
Figure 20G:
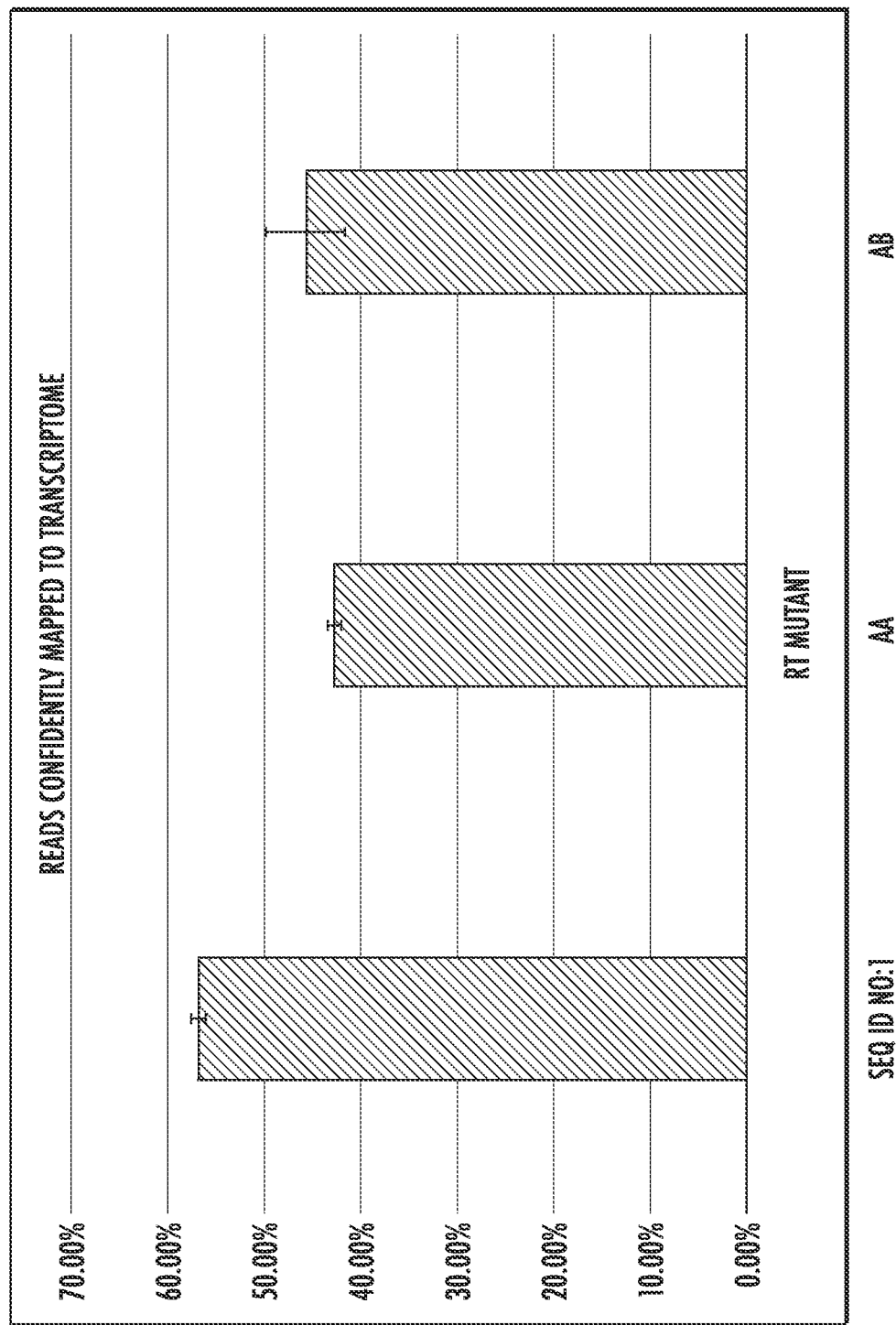
Figure 20H:
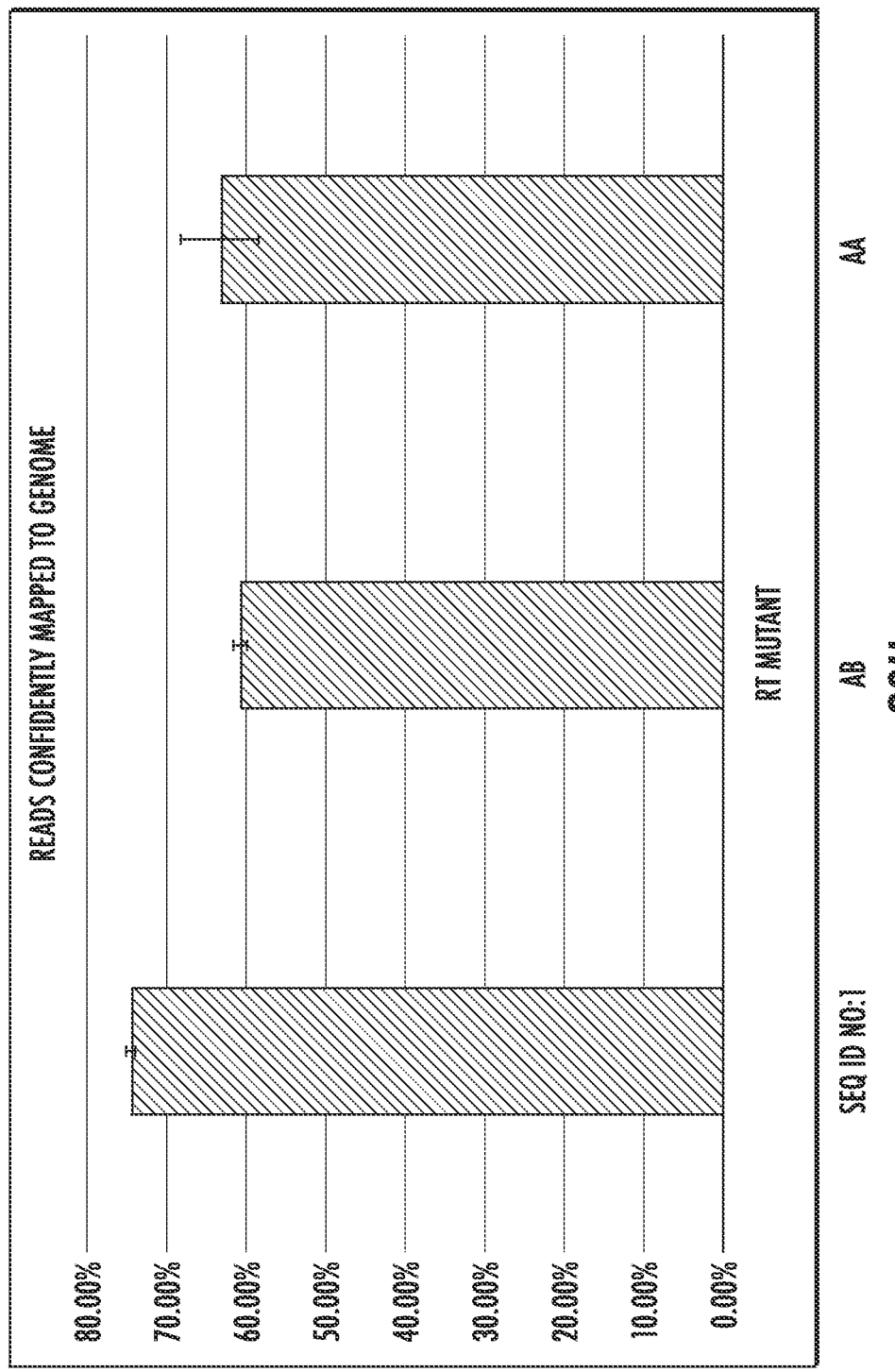
Figure 20I:
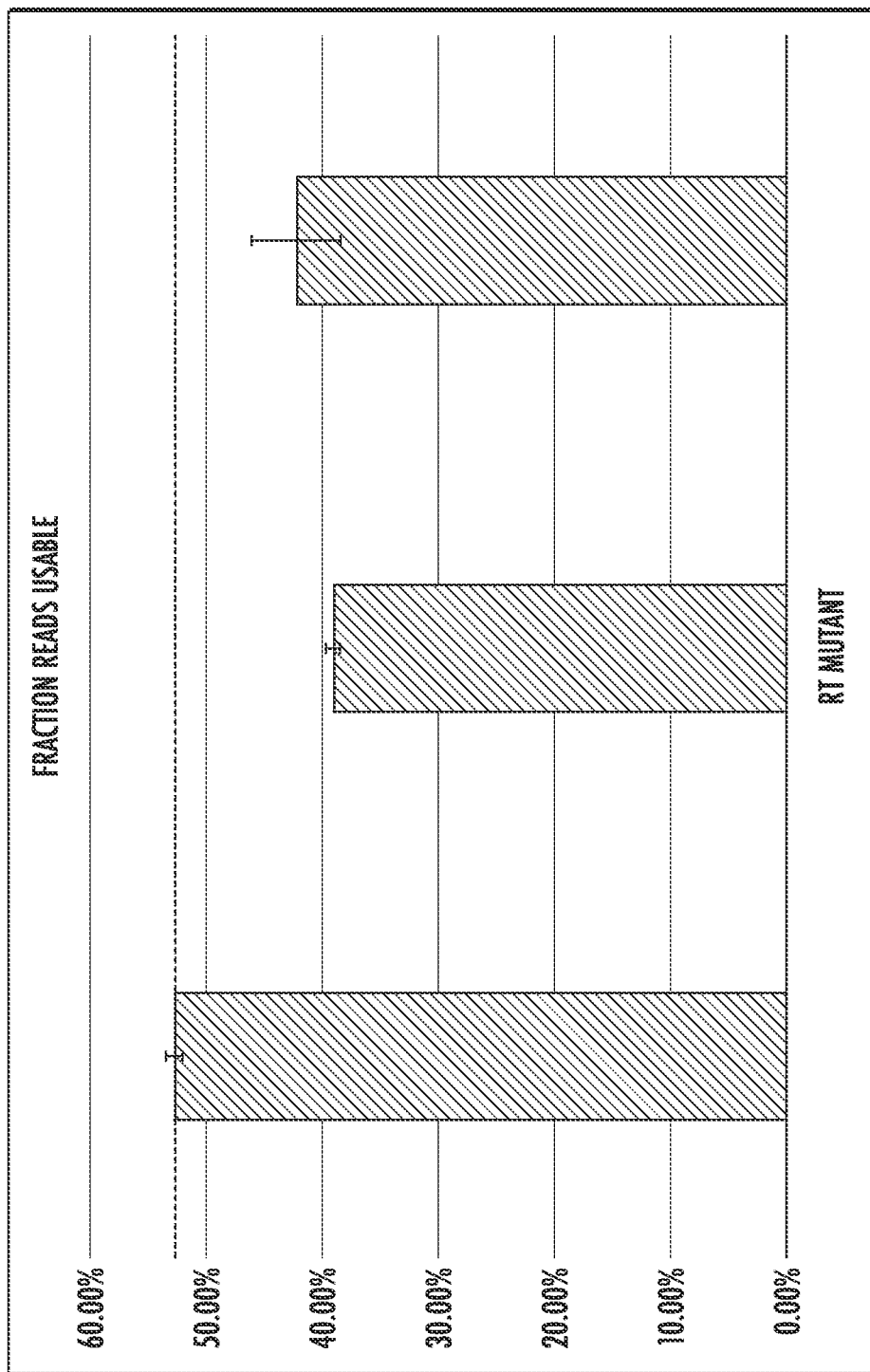

Reverse transcription and sequencing reactions were prepared. The reaction volume was 50 µl; reactions contained 5'-end labeled FAM Reverse Transcriptase primer 2, GEM-U reagent, RNA template (RNA Temp 2CE), template switching oligo 1 (TSO1), and the indicated engineered reverse transcriptase. Stock concentrations and final concentrations in the reactions are shown in Table 2. The reactions included stoichiometrically equal amounts of enzyme and template for single turnover conditions. Reactants were incubated at 53° C. for one hour, then diluted 1:40 in water and then 1:20 in HiDi formamide. The formamide mixture was heated to 95° C. for 5 mins, then chilled on ice for 2 mins. Samples were loaded on the CE, the DS-33 dye set was selected and fragment analysis (SnapShot) was performed using the GS120LIZ size standard. The assay was validated with synthetically sized oligonucleotides and with a transcription positive, template switching null engineered reverse transcriptase (AR) (data not shown) and a transcription positive, template switching positive commercially prepared reverse transcriptase (Enzyme Mix C). The GEM-U reagent approximates the formulation of the actual reagent mixture in a GEM assay when the contents of the $Z_1$ and $Z_2$ channels are mixed. Results from one such experiment are shown in FIG. 17.

TABLE 2

Capillary Electrophoresis (CE) Assay Reactants and Template, Primer and TSO sequences

|  | Initial | Final | 1x | 8x |
| --- | --- | --- | --- | --- |
| RT Reagent B (2000165) | 4.00 x | 1.00 x | 9.54 uL | 76.34 uL |
| FAM.RT.Primer2 (Variable) | 100.00 uM | 0.5000 uM | 0.250 uL | 2.000 uL |
| RNA.Temp2.CE (Variable) | 84.40 uM | 1.00 uM | 0.59 uL | 4.74 uL |
| TSO1.Oligo (Variable) | 1000.00 uM | 64.00 uM | 3.20 uL | 25.60 uL |
| DTT | 1000.00 mM | 20.00 mM | 1.00 uL | 8.00 uL |

TABLE 2-continued

Capillary Electrophoresis (CE) Assay Reactants and
Template, Primer and TSO sequences

|  | Initial | Final | 1x | 8x |
|---|---|---|---|---|
| Gel Bead Buffer (2000018) | 1.00 x | 0.24 x | 11.83 uL | 94.66 uL |
| Polyacylamide Solution (2000052) | 10% | 0.50% | 2.50 uL | 20.00 uL |
| Enzyme | 15.40 uM | 0.50 uM | 1.62 uL | 12.99 uL |
| Water | — | — | 19.46 uL | 155.68 uL |
| Total |  |  | 50.00 uL | 400.00 uL |

Example 12. Mean Read Per Cell

GEM-x reactions were performed with a variety of reverse transcriptases. The percent of valid barcodes was determined. In one experiment, an enzyme having the amino acid sequence set forth in SEQ ID NO:1 and engineered reverse transcriptases AG, AF, AB, AA, AH and AI were evaluated. Results of one such experiment are shown in FIG. 18. The median number of genes and UMIs detected per cell over 20,000 raw reads per cell was determined. Results of one such experiment are summarized in FIG. 18A. The median number of genes and UMIs detected per cell over 50,000 raw reads per cell was determined. Results of one such experiment are summarized in FIG. 18C. The fraction of ribosomal protein and mitochondrial UMI counts were determined. Results of one such experiment are summarized in FIG. 18D. The transcript coverage of different length transcripts for each variant was determined. Results from one such experiment are summarized in FIG. 18E.

Example 13. Mean Read Per Cell

GEM-x 5' reactions were performed using a backpack specific to the 5' assay, Chip K. The Chip K backpack accounts for the slightly larger gel beads. Chip K shows a slightly higher pressure in the gel bead line versus Chip G. Results from one such series of experiments are shown in FIG. 20.

Example 14. Mean Read Per Cell

Figure 21A:
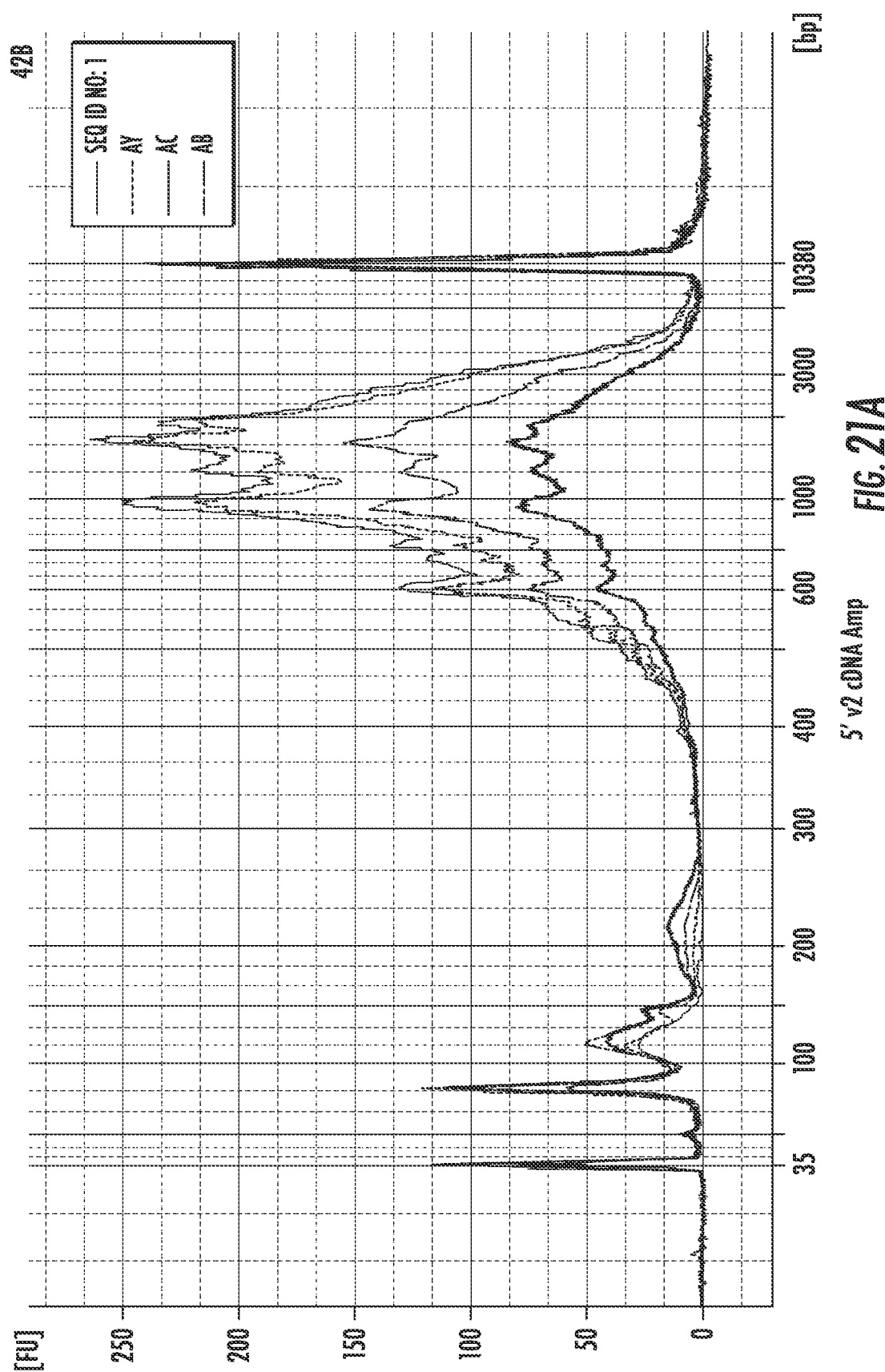
Figure 21B:
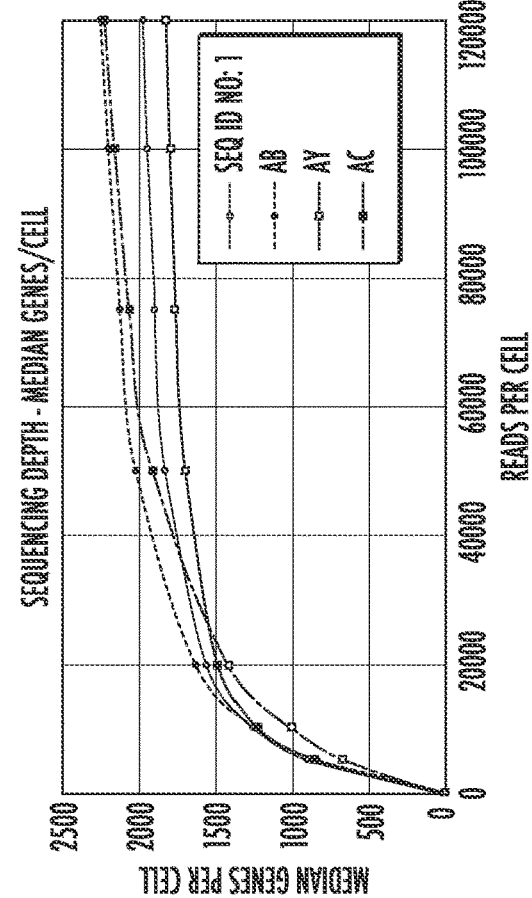

5' amplification and GEM-x reactions were performed with a variety of reverse transcriptases. The percent of valid barcodes was determined. In one experiment, an enzyme having the amino acid sequence set forth in SEQ ID NO:1 and engineered reverse transcriptases AB, AC and AY were evaluated. Results of one such experiment are shown in FIG. 21. Traces of the results obtained from the 5' amplification assay are shown in FIG. 21A. The median number of genes and UMIs detected per cell over 20,000 raw reads per cell was determined. The median number of genes and UMIs detected per cell over 50,000 raw reads per cell was determined. The median number of genes and UMIs detected per cell over 120,00 raw reads per cell was determined. Results of one such experiment are summarized in FIG. 21B. The fraction of ribosomal protein and mitochondrial UMI counts were determined. The transcript coverage of different length transcripts for each variant was determined. Results from one such experiment are summarized in FIG. 21C.

Example 15. Mean Read Per Cell

Figure 22:
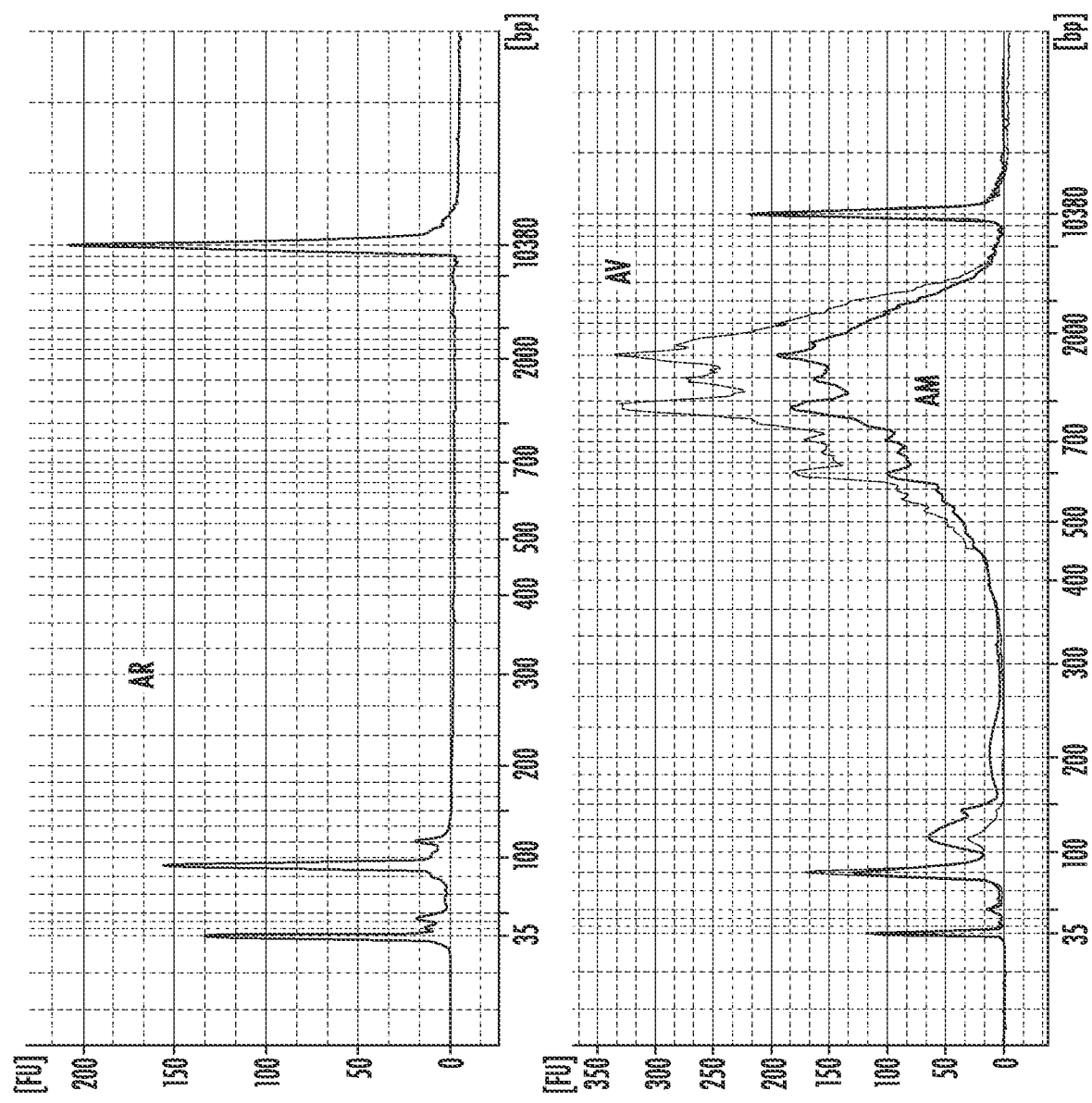
FIG. 22 provides a summary of data obtained from a series of assays with variant AR (top panel and variants AV and AM (bottom panel). The absence of peaks between about 400 and 10380 indicate the variant AR did not template-switch. The presence of peaks between about 400 and 10380 indicate variants AV and AM are capable of template switching.

5' amplification assays were performed with a variety of reverse transcriptases. The percent of valid barcodes was determined. In one experiment, engineered reverse transcriptases AR, AV and AM were evaluated. Results of one such experiment are shown in FIG. 22.

Example 16. Mean Read Per Cell

Figure 23A:
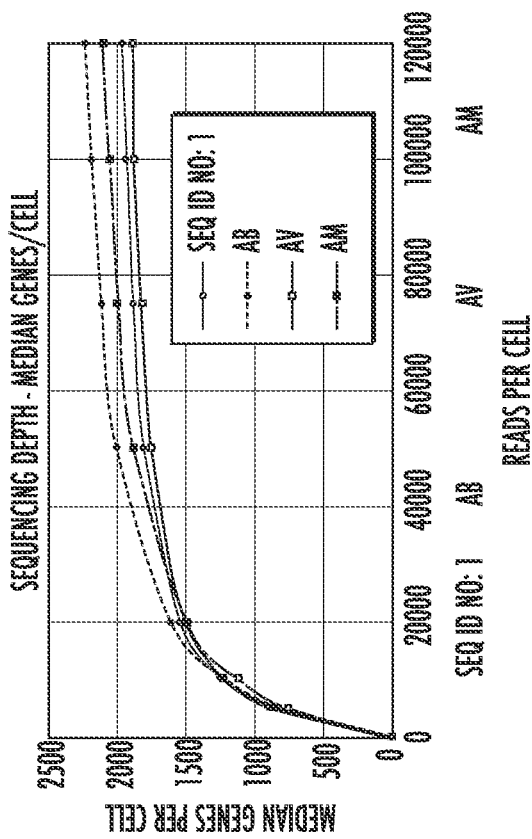

GEM-x reactions were performed with a variety of reverse transcriptases. The percent of valid barcodes was determined. In one experiment, an enzyme having the amino acid sequence set forth in SEQ ID NO:1 and engineered reverse transcriptases AB, AV and AM were evaluated. Results of one such experiment are shown in FIG. 23. The median number of genes and UMIs detected per cell over 20,000 raw reads per cell was determined. The median number of genes and UMIs detected per cell over 50,000 raw reads per cell was determined. The median number of genes and UMIs detected per cell over 120,00 raw reads per cell was determined. Results of one such experiment are summarized in FIG. 23A. The fraction of ribosomal protein and mitochondrial UMI counts were determined. The transcript coverage of different length transcripts for each variant was determined. Results from one such experiment are summarized in FIG. 23B.

Figure 24A:
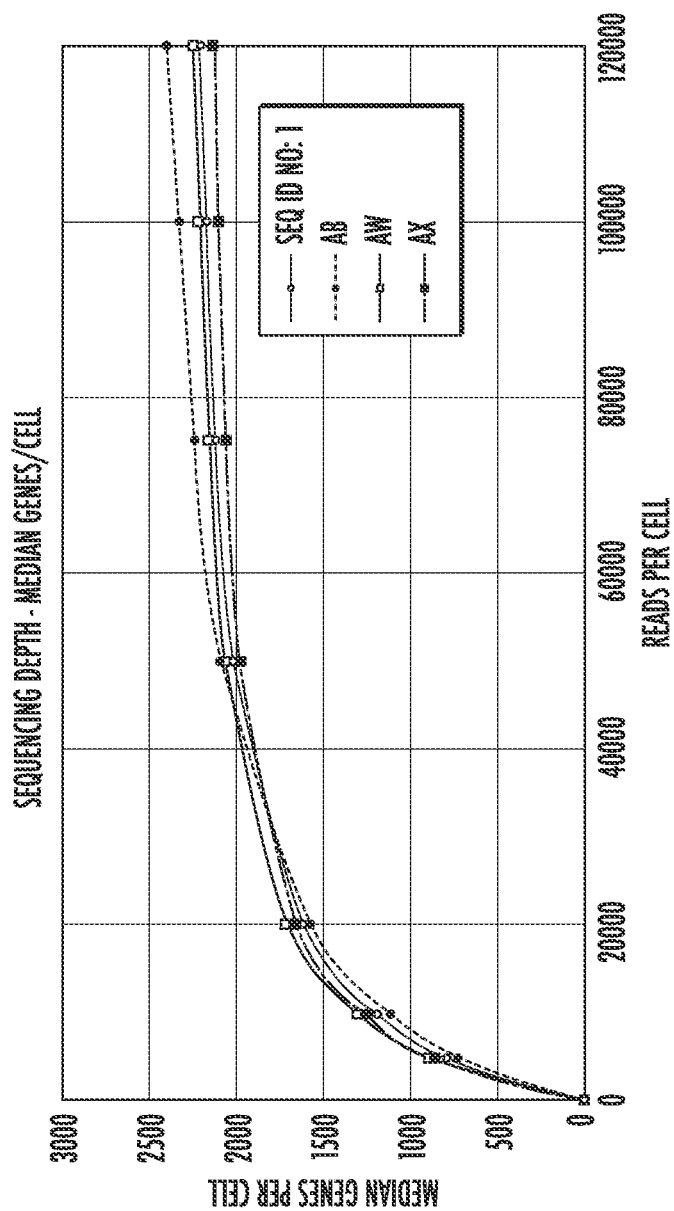
FIGS. 24A-24B provide a summary of data obtained from a series of assays with an enzyme having the amino acid sequence set forth in SEQ ID NO:1 and variants AB, AW and AX.
Figure 24B:
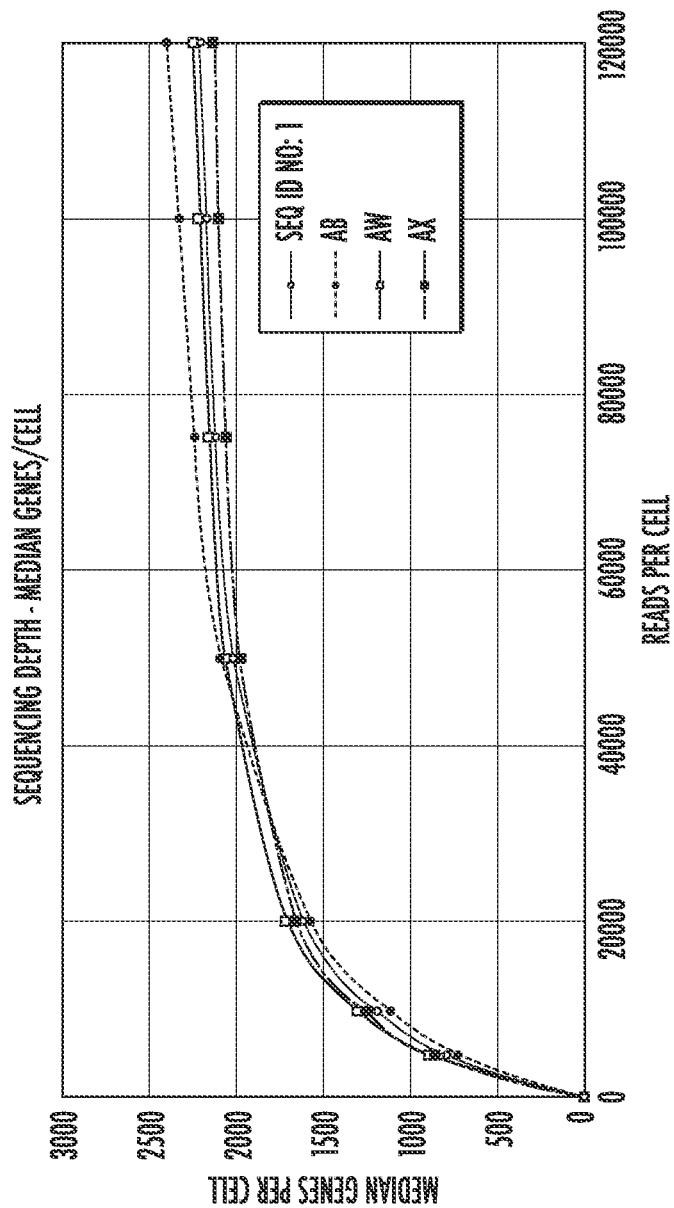

Similar experiments were performed with an enzyme having the amino acid sequence set forth in SEQ ID NO:1 and engineered reverse transcriptases AB, AW and AX were evaluated. Results of one such experiment are shown in FIG. 24.

That which is claimed:

1. An engineered reverse transcriptase comprising a combination of mutations in the amino acid sequence of SEQ ID NO: 18, wherein the combination of mutations comprises:
   (a) E69K, L139P, D200N, E302R, T306K, W313F, T330P, L435K, P448A, D449G, N454K, D524N, L603W, E607K; and
   (b) one or more of A32V, M39V, M66L, L72R, L139P, F155Y, D200C, D200E, E201Q, H204R, G248C, E286R, T287A, Y344L, I347L, W388R, R411F, K435G, H503V, D583N, H594K, H594Q, L603F, E607G, H634Y, G637R, H638G, D653H, and L671P.

2. The engineered reverse transcriptase of claim 1, wherein the engineered reverse transcriptase comprises M66L, E69K, L139P, D200N, E302R, T306K, W313F, T330P, P448A, D449G, N454K, L603W and E607K.

3. The engineered reverse transcriptase of claim 1, wherein the engineered reverse transcriptase comprises E69K, L139P, D200N, E302R, T306K, W313F, T330P, P448A, D449G, N454K, H503V, L603W and E607K.

4. The engineered reverse transcriptase of claim 1, wherein the engineered reverse transcriptase comprises E69K, L139P, D200N, E302R, T306K, W313F, T330P, P448A, D449G, N454K, L603W, E607K and H634Y.

5. The engineered reverse transcriptase of claim 2, further comprising H503V.

6. The engineered reverse transcriptase of claim 2, further comprising H634Y.

7. The engineered reverse transcriptase of claim 2, further comprising H503V and H634Y.

8. The engineered reverse transcriptase of claim 1, wherein the engineered reverse transcriptase comprises L139P, D200N, T330P, L603W, and E607K, and further comprises a second combination of mutations selected from the group consisting of:
   (a) M39V mutation, an E69K mutation, an E302R mutation, a T306K mutation, a W313F mutation, a K435G mutation, a P448A mutation, a D449G mutation, and an N454K mutation (AA);
   (b) an M66L mutation, an E69K mutation, an E302R mutation, a T306K mutation, a W313F mutation, a K435G mutation, a P448A mutation, a D449G mutation, and an N454K mutation (AB);
   (c) a M39V mutation, an M66L mutation, an E69K mutation, an E302R mutation, a T306K mutation, a W313F mutation, a K435G mutation, a P448A mutation, a D449G mutation, and an N454K mutation (AC);
   (d) a M39V mutation, an M66L mutation, an E69K mutation, an E201Q mutation, E302R mutation, a T306K mutation, a W313F mutation, a K435G mutation, a P448A mutation, a D449G mutation, an N454K mutation, an FI503V mutation, an FI594K mutation, and an FI634Y mutation (AD);
   (e) an E69K mutation, an E201Q mutation, a T287A mutation, E302R mutation, a T306K mutation, a W313F mutation, a K435G mutation, a P448A mutation, a D449G mutation, an N454K mutation, (AE);
   (f) an M39V mutation, an M66L mutation, an E69K mutation, an E201Q mutation, a T287A mutation, E302R mutation, a T306K mutation, a W313F mutation, a C409S mutation, a K435G mutation, a P448A mutation, a D449G mutation, an N454K mutation, an H503V mutation, an H594K mutation, and an H634Y mutation (AF);
   (g) an E69K mutation, an E201Q mutation, a T287A mutation, E302R mutation, a T306K mutation, a W313F mutation, a C409S mutation, a K435G mutation, a P448A mutation, a D449G mutation, an N454K mutation, and an FI634Y mutation (AG);
   (h) an E69K mutation, an E201Q mutation, an E302R mutation, a T306K mutation, a W313F mutation, a K435G mutation, a P448A mutation, a D449G mutation, and an N454K mutation, (AH);
   (i) an E69K mutation, a T287A mutation, an E302R mutation, a T306K mutation, a W313F mutation, a K435G mutation, a P448A mutation, a D449G mutation, and an N454K mutation (AI);
   (j) an E69K mutation, an E201Q mutation, a T287A mutation, an E302R mutation, a T306K mutation, a W313F mutation, a K435G mutation, a P448A mutation, a D449G mutation, an N454K mutation, and an FI634Y mutation (AJ);
   (k) an E69K mutation, an E201Q mutation, a T287A mutation, an E302R mutation, a T306K mutation, a W313F mutation, a K435G mutation, a P448A mutation, a D449G mutation, an N454K mutation, an FI503V mutation, an FI594K mutation, and an FI634Y mutation (AK);
   (l) an M39V mutation, an M66L mutation, an E69K mutation, an E201Q mutation, a T287A mutation, an E302R mutation, a T306K mutation, a W313F mutation, an R411F mutation, a K435G mutation, a P448A mutation, a D449G mutation, an N454K mutation, an FI503V mutation, an FI594K mutation, an FI634Y mutation, and a G637R mutation (AL);

(m) a M66L mutation, an E69K mutation, an E302R mutation, a T306K mutation, a W313F mutation, an N454K mutation, an FI503V mutation, and an FI634Y mutation (AM);

(n) a M39V mutation, an M66L mutation, an E201Q mutation, a P448A mutation, a D449G mutation, an FI503V mutation, an FI594K mutation, and an FI634Y mutation (AN);

(o) an M39V mutation, an M66L mutation, an E201Q mutation, a T287A mutation, P448A mutation, a D449G mutation, an FI503V mutation, an FI594K mutation, and an FI634Y mutation (AO);

(p) an M39V mutation, an M66L mutation, an E201Q mutation, a T287A mutation, a P448A mutation, a D449G mutation, an FI503V mutation, an FI594K mutation, an FI634Y mutation, a P636FI mutation (AP);

(q) an E69K mutation, an E302R mutation, a T306K mutation, a W313F mutation, an N454K mutation, and an FI503V mutation (AQ);

(r) an FI503V mutation and an FI634Y mutation (AR);

(s) an E69K mutation, an E302R mutation, a T306K mutation, a W313F mutation, a K435G mutation, and an N454K mutation (AV);

(t) an E69K mutation, an E302R mutation, a T306K mutation, a W313F mutation, a K435G mutation, a P448A mutation, a D449G mutation, an N454K mutation, and an FI638G mutation (AW);

(u) an E69K mutation, an F155Y mutation, an E302R mutation, a T306K mutation, a W313F mutation, a K435G mutation, a P448A mutation, a D449G mutation, an N454K mutation, and an FI638G mutation (AX); and (v) an E69K mutation, an E302R mutation, a T306K mutation, a W313F mutation, a K435G mutation, an N454K mutation, and an FI594K mutation (AY).

9. The engineered reverse transcriptase of claim 1, wherein said engineered reverse transcriptase exhibits an altered reverse transcriptase related activity as compared to a reverse transcriptase having the amino acid sequence set forth in SEQ ID NO:1; and wherein the altered reverse transcriptase related activity is selected from:

(a) an increased ability to yield median UMI counts per cell;
(b) an increased transcription efficiency;
(c) an increased template switching (TSO) efficiency;
(d) a decreased template switching (TSO) efficiency;
(e) an increased ability to yield UMI reads from genes of a desired length in a 3' reverse transcription assay;
(f) an increased ability to yield UMI reads from genes of a desired length in a 5' reverse transcription assay;
(g) an increased ability to yield median UM is/cell; and/or (h) an increased transcription efficiency and an increased template switching efficiency.

10. The engineered reverse transcriptase of claim 1, wherein said altered reverse transcriptase related activity is an increased template switching efficiency as compared to the template switching efficiency of a reverse transcriptase having the amino acid sequence set forth in SEQ ID NO:1.

11. The engineered reverse transcriptase of claim 1, wherein the engineered reverse transcriptase maintains reverse transcriptase activity in a low reaction volume, wherein the low reaction volume is less than 1 nanoliter, less than 750 picoliters, or less than 500 picoliters.

12. The engineered reverse transcriptase of claim 9, wherein the engineered reverse transcriptase exhibits an altered reverse transcriptase related activity in a low reaction volume; and wherein the low reaction volume is less than 1 nanoliter, less than 750 picoliters, or less than 500 picoliters.

13. An engineered reverse transcriptase encoded by a nucleic acid sequence from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

14. The engineered reverse transcriptase of claim 13, wherein the engineered reverse transciptase is encoded by the nucleic acid sequence is SEQ ID NO: 4.

15. The engineered reverse transcriptase of claim 13, wherein the engineered reverse transciptase is encoded by the nucleic acid sequence is SEQ ID NO: 17.

16. An engineered reverse transcriptase of claim 1, wherein the engineered reverse transcriptase maintains reverse transcription activity at temperatures between about 70° C. to about 90° C. when compared to SEQ ID NO: 1.

17. The engineered reverse transcriptase of claim 1, wherein said altered reverse transcriptase related activity is decreased template switching efficiency as compared to the template switching efficiency of a reverse transcriptase having the amino acid sequence set forth in SEQ ID NO:1.

18. The engineered reverse transcriptase of claim 10, wherein the engineered reverse transcriptase comprises L139P, D200N, T330P, L603W, and E607K, and further comprises a second combination of mutations selected from the group consisting of:

an M39V mutation, an M66L mutation, an E69K mutation, an E201Q mutation, a T287A mutation, E302R mutation, a T306K mutation, a W313F mutation, a C409S mutation, a K435G mutation, a P448A mutation, a D449G mutation, an N454K mutation, an H503V mutation, an H594K mutation, and an H634Y mutation (AF); or an E69K mutation, an E201Q mutation, a T287A mutation, an E302R mutation, a T306K mutation, a W313F mutation, a K435G mutation, a P448A mutation, a D449G mutation, an N454K mutation, an FI503V mutation, an FI594K mutation, and an FI634Y mutation (AK).

* * * * *